(12) United States Patent
Wu et al.

(10) Patent No.: US 8,343,968 B2
(45) Date of Patent: Jan. 1, 2013

(54) CASE OF RENIN INHIBITORS

(75) Inventors: Tom Yao-Hsiang Wu, San Diego, CA (US); Helene Juteau, Montreal (CA); Michel Gallant, Pierrefonds (CA); Daniel Dube, Saint-Lazare (CA); Patrick Roy, Dollard des Omeaux (CA); Renee Aspiotis, Kirkland (CA); Erich I. Grimm, Baie d'Urfe (CA); Sebastien Laliberte, Vaudreuil-Dorion (CA); Austin Chen, Pierrefonds (CA)

(73) Assignee: Merck Canada Inc., Kirkland, Quebec (CA)

( * ) Notice: Subject to any disclaimer, the term of this patent is extended or adjusted under 35 U.S.C. 154(b) by 233 days.

(21) Appl. No.: 12/594,905

(22) PCT Filed: May 23, 2008

(86) PCT No.: PCT/CA2008/001005
§ 371 (c)(1), (2), (4) Date: Oct. 6, 2009

(87) PCT Pub. No.: WO2008/141462
PCT Pub. Date: Nov. 27, 2008

(65) Prior Publication Data
US 2010/0120859 A1 May 13, 2010

Related U.S. Application Data

(60) Provisional application No. 60/931,520, filed on May 24, 2007.

(51) Int. Cl.
*A61K 31/535* (2006.01)
*A61K 31/445* (2006.01)
*C07D 413/12* (2006.01)
*C07D 211/60* (2006.01)

(52) U.S. Cl. ............... 514/235.5; 514/330; 544/130; 546/245

(58) Field of Classification Search .......... 544/130; 546/245; 514/235.5, 330
See application file for complete search history.

(56) References Cited

FOREIGN PATENT DOCUMENTS

| | | |
|---|---|---|
| WO | WO03093267 | 11/2003 |
| WO | WO2004002957 | 1/2004 |
| WO | WO2004096116 | 11/2004 |
| WO | WO2004096366 | 11/2004 |
| WO | WO2004096769 | 11/2004 |
| WO | WO2004096799 | 11/2004 |
| WO | WO2004096803 | 11/2004 |
| WO | WO2004096804 | 11/2004 |
| WO | WO2005040120 | 5/2005 |
| WO | WO2005040165 | 5/2005 |
| WO | WO2005040173 | 5/2005 |
| WO | WO2005054243 | 6/2005 |
| WO | WO2005054244 | 6/2005 |
| WO | WO2006131884 | 2/2006 |
| WO | WO2006021399 | 3/2006 |
| WO | WO2006021401 | 3/2006 |
| WO | WO2006021402 | 3/2006 |
| WO | WO2006021403 | 3/2006 |
| WO | WO2006061791 | 6/2006 |
| WO | WO2006063610 | 6/2006 |
| WO | WO2006064484 | 6/2006 |
| WO | WO 2006/069788 * | 7/2006 |
| WO | WO2006058546 | 8/2006 |
| WO | WO2006059304 | 8/2006 |
| WO | WO2006079988 | 8/2006 |
| WO | WO2006092268 | 9/2006 |
| WO | WO2006129237 A2 | 12/2006 |
| WO | WO2007/009250 | 1/2007 |
| WO | WO2007034445 A2 | 3/2007 |
| WO | WO2007049224 | 5/2007 |
| WO | WO2007088514 | 8/2007 |
| WO | WO2007099509 | 9/2007 |
| WO | WO2007102127 | 9/2007 |
| WO | WO2008/058387 | 5/2008 |
| WO | WO2008/141462 C2 | 11/2008 |

OTHER PUBLICATIONS

Kehoe et al. Lancet Neurol 2007: 6: 373-78.*
Pratt et al., Circulation, 1996: 93: 848-852.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrived on Sep. 23, 2003]. Retrieved from the Internet, URL; http://www.cnn.com/2003/HEALTH/conditions/09/24/alzheimers.drug.ap/index.html>.*

* cited by examiner

*Primary Examiner* — Rebecca Anderson
(74) *Attorney, Agent, or Firm* — James L. McGinnis; Catherine D. Fitch

(57) ABSTRACT

The present invention relates to piperidine-based renin inhibitor compounds having carboxylate or carboxylic acid terminal groups, and their use in treating cardiovascular events and renal insufficiency.

15 Claims, No Drawings

CASE OF RENIN INHIBITORS

CROSS REFERENCE TO RELATED APPLICATIONS

This application is a U.S. National Phase application under 35 U.S.C.§371 of PCT Application No. PCT/CA2008/001005 filed May 23, 2008, which claims priority under 35 U.S.C.§119(e) from U.S. Provisional Application No. 60/931,520 filed May 24, 2007.

The claimed invention was made as a result of activities undertaken within the scope of a joint research agreement between Merck & Co., Inc. and Actelion Pharmaceuticals Ltd. The agreement was executed on Dec. 4, 2003. The field of the invention is described below.

FIELD OF THE INVENTION

The invention relates to novel renin inhibitors of the general formula (I). The invention also concerns related aspects including processes for the preparation of the compounds, pharmaceutical compositions containing one or more compounds of formula (I) and especially their use as renin inhibitors in cardiovascular events and renal insufficiency.

BACKGROUND OF THE INVENTION

In the renin-angiotensin system (RAS) the biologically active angiotensin II (Ang II) is generated by a two-step mechanism. The highly specific enzyme renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAS represents a major advance in the treatment of cardiovascular diseases. ACE inhibitors and $AT_1$ blockers have been accepted to treat hypertension (Waeber B. et al., "The renin-angiotensin system: role in experimental and human hypertension", in Birkenhager W. H., Reid J. L. (eds): *Hypertension*, Amsterdam, Elsevier Science Publishing Co, 1986, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (*Suppl.* 3A), 83) and myocardial infarction (Pfeffer M. A. et al., *N Engl. J. Med.*, 1992, 327, 669).

The rationale to develop renin inhibitors is the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be by-passed by chymase, a serine protease (Husain A., *J. Hypertens.*, 1993, 11, 1155). In patients inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the $AT_1$ receptor (e.g. by losartan) on the other hand overexposes other AT-receptor subtypes (e.g. $AT_2$) to Ang II, whose concentration is significantly increased by the blockade of $AT_1$ receptors. In summary, renin inhibitors are expected to demonstrate a different pharmaceutical profile than ACE inhibitors and $AT_1$ blockers with regard to efficacy in blocking the RAS and in safety aspects.

Only limited clinical experience (Azizi M. et al., *J. Hypertens.*, 1994, 12, 419; Neutel J. M. et al., *Am. Heart*, 1991, 122, 1094) has been created with renin inhibitors because of their insufficient oral activity due to their peptidomimetic character (Kleinert H. D., *Cardiovasc. Drugs*, 1995, 9, 645). The clinical development of several compounds has been stopped because of this problem together with the high cost of goods. Only one compound containing four chiral centers has entered clinical trials (Rahuel J. et al., *Chem. Biol.*, 2000, 7, 493; Mealy N. E., *Drugs of the Future*, 2001, 26, 1139). Thus, renin inhibitors with good oral bioavailability and long duration of action are required. Recently, the first non-peptide renin inhibitors were described which show high in vitro activity (Oefner C. et al., *Chem. Biol.*, 1999, 6, 127; Patent Application WO97/09311; Marki H. P. et al., *Il Farmaco*, 2001, 56, 21). However, the development status of these compounds is not known.

The present invention relates to the identification of renin inhibitors of a non-peptidic nature and of low molecular weight. Described are orally active renin inhibitors of long duration of action which are active in indications beyond blood pressure regulation where the tissular renin-chymase system may be activated leading to pathophysiologically altered local functions such as renal, cardiac and vascular remodeling, atherosclerosis, and possibly restenosis. So, the present invention describes these non-peptidic renin inhibitors.

The compounds described in this invention represent a novel structural class of renin inhibitors.

SUMMARY OF THE INVENTION

The present invention is directed to certain compounds and their use in the inhibition of the renin enzyme, including treatment of conditions known to be associated with the renin system. The invention includes compounds of Formula I:

The present invention relates to compounds of the formula (I)

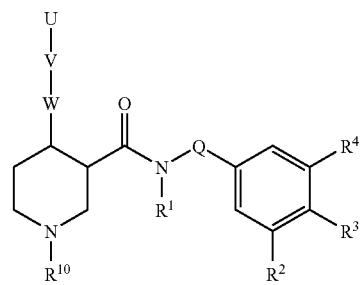

wherein $R^1$ is $C_1$-$C_6$ alkyl or $C_3$-$C_7$ cycloalkyl;

$R^2$ is —O($CH_2$)$_{1-3}$OCH$_3$ or —($CH_2$)$_{1-3}$OCH$_3$;

$R^3$ is selected from the group consisting of:
hydrogen,

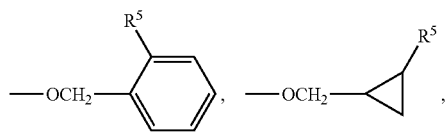

and
—O(CH$_2$)$_2$C(CH$_3$)$_2$R$^5$;

$R^4$ is selected from the group consisting of:
hydrogen,

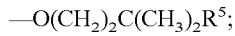

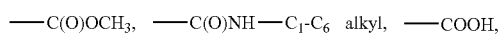

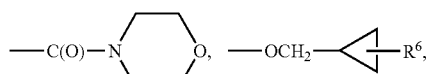

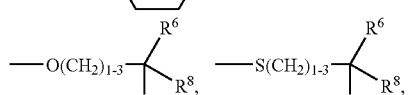

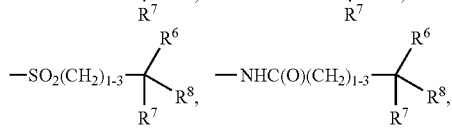

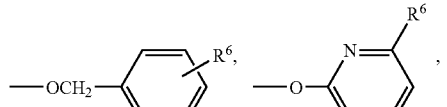

—O(CH$_2$)$_3$—NH

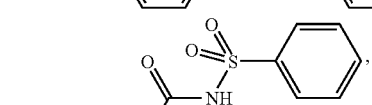

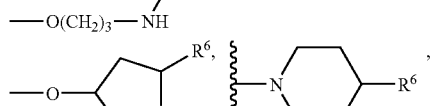

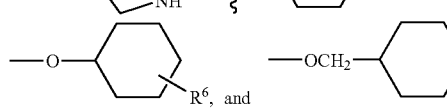

$R^5$ is selected from the group consisting of —COOH, —COOC$_1$-C$_6$ alkyl;

$R^6$ is selected from the group consisting of:
—COOR$^9$,
—CH$_2$COOR$^9$,
—CON(CH$_3$)SO$_2$CH$_3$,
—CONHSO$_2$CH$_3$,
—C(O)NH$_2$
—CH(CH$_2$CH$_3$)COOH,
—CONHSO$_2$CH$_3$,
—NH$_2$,

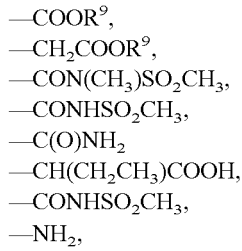

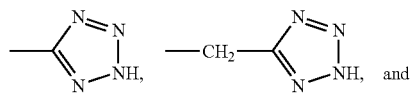

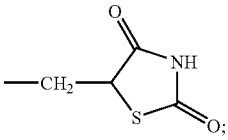

$R^7$ and $R^8$ are independently selected from the group consisting of:
-hydrogen,
—C$_{1-6}$ alkyl,
—OH,
—OCH$_3$,
—COOH,
—NH$_2$, and

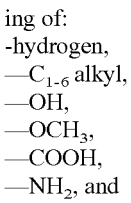

or $R^7$ and $R^8$, together with the atom to which they are attached, form a C$_{3-8}$ cycloalkyl ring;

$R^9$ is selected from the group consisting of:
-hydrogen,
—C$_1$-C$_6$alkyl,
—(CH$_2$)$_{2-4}$CH(ONO$_2$)CH$_2$ONO$_2$,
—CH$_2$C(O)N(CH$_3$)$_2$,
—CH$_2$OCOC(CH$_3$)$_3$,
—CH$_2$OCH$_2$OCOCH$_3$,
—CH(CH$_3$)OCOCH(CH$_3$)$_2$,
—CH(CH$_3$)COOCH$_2$CH$_3$,
—CH$_2$CH$_2$N(CH$_3$)$_2$,
—CH(CH$_3$)OCOOCH$_2$CH$_3$,
—CH(CH$_3$)OCOOCH(CH$_3$)$_2$,

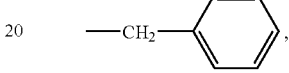

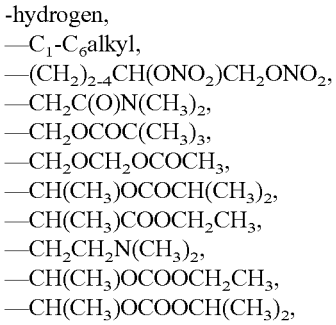

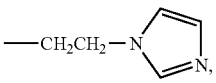

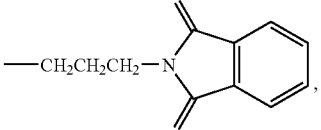

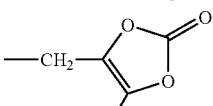 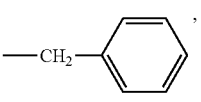

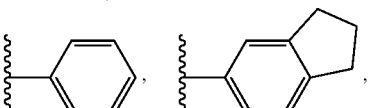

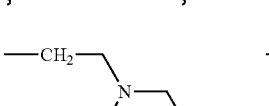 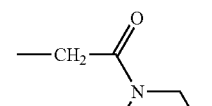

$R^{10}$ is selected from the group consisting of:
- -hydrogen,
- —COOCH$_3$,
- —COOCH(CH$_3$)OCOCH$_3$,

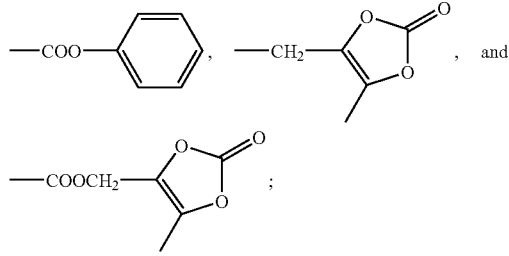

W is a phenyl ring or a six-membered, aromatic ring containing one to four nitrogen atoms, wherein said rings are substituted by V in para position;
V is a bond; —(CH$_2$)$_r$—; -A-(CH$_2$)$_s$—; —CH$_2$-A-(CH$_2$)$_t$—; —(CH$_2$)$_s$-A-; —(CH$_2$)$_2$-A-(CH$_2$)$_u$—;-A-(CH$_2$)$_v$—B—; —CH$_2$—CH$_2$—CH$_2$-A-CH$_2$—; -A-CH$_2$—CH$_2$—B—CH$_2$—; —CH$_2$-A-CH$_2$—CH$_2$—B—; —CH$_2$—CH$_2$—CH$_2$-A-CH$_2$—CH$_2$—; —CH$_2$—CH$_2$—CH$_2$—CH$_2$-A-CH$_2$—; -A-CH$_2$—CH$_2$—B—CH$_2$—CH$_2$—; —CH$_2$-A-CH$_2$—CH$_2$—CH$_2$—B—CH$_2$—; —CH$_2$-A-CH$_2$—CH$_2$—CH$_2$—B—; —CH$_2$—CH$_2$-A-CH$_2$—CH$_2$—B—; —O—CH$_2$—CH(OCH$_3$)—CH$_2$—O—; —O—CH$_2$—CH(CH$_3$)—CH$_2$—O—; —O—CH$_2$—CH(CF$_3$)—CH$_2$—O—; —O—CH$_2$—C(CH$_3$)$_2$—CH$_2$—O—; —O—CH$_2$—C(CH$_3$)$_2$—CH$_2$—O—; —O—C(CH$_3$)$_2$—CH$_2$—O—; —O—CH$_2$—CH(CH$_3$)—O—; —O—CH(CH$_3$)—CH$_2$—O—; —O—CH$_2$—C(CH$_2$CH$_3$)—O—; or —O—C(CH$_2$CH$_3$)—CH$_2$—O—;
A and B are independently selected from the group consisting of —O—. —S—, —S(O)— and —S(O)$_2$—;
U is unsubstituted aryl; mono-, di-, tri-or tetra-substituted aryl wherein the substituents are independently selected from the group consisting of halogen, alkyl, alkoxy, and —CF$_3$; or mono-, di-, or tri-substituted heteroaryl wherein the substituents are independently selected from the group consisting of halogen, alkyl, alkoxy, and —CF$_3$;
Q is methylene or ethylene;
n is the integer 0 or 1;
r is the integer 3, 4, 5, or 6;
s is the integer 2, 3, 4, or 5;
t is the integer 1, 2, 3, or 4;
u is the integer 1, 2, or 3; and
v is the integer 2, 3, or 4;
and optically pure enantiomers, mixtures of enantiomers such as racemates, diastereomers, mixtures of diastereomers, diastereomeric racemates, mixtures of diastereomeric racemates, meso-forms, tautomers, salts, solvates, and morphological forms thereof.

DETAILED DESCRIPTION OF THE DISCLOSURE

The compounds of Formula I above, and pharmaceutically acceptable salts thereof, are renin inhibitors. The compounds are useful for inhibiting renin and treating conditions such as hypertension.

Any reference to a compound of formula (I) is to be understood as referring also to optically pure enantiomers, mixtures of enantiomers such as racemates, diastereomers, mixtures of diastereomers, diastereomeric racemates, mixtures of diastereomeric racemates, meso-forms and tautomers, as well as salts (especially pharmaceutically acceptable salts) and solvates (including hydrates) of such compounds, and morphological forms, as appropriate and expedient. The present invention encompasses all these forms. Mixtures are separated in a manner known per se, e.g. by column chromatography, thin layer chromatography (TLC), high performance liquid chromatography (HPLC), or crystallization. The compounds of the present invention may have chiral centers, e.g. one chiral center (providing for two stereoisomers, (R) and (S)), or two chiral centers (providing for up to four stereoisomers, (R,R), (S,S), (R,S), and (S,R)). This invention includes all of these optical isomers and mixtures thereof. Unless specifically mentioned otherwise, reference to one isomer applies to any of the possible isomers. Whenever the isomeric composition is unspecified, all possible isomers are included.

Tautomers of compounds defined in Formula I are also included within the scope of the present invention. For example, compounds including carbonyl —CH$_2$C(O)— groups (keto forms) may undergo tautomerism to form hydroxyl —CH=C(OH)— groups (enol forms). Both keto and enol forms are included within the scope of the present invention.

In addition, compounds with carbon-carbon double bonds may occur in Z-and E-forms with all isomeric forms of the compounds being included in the present invention.

Compounds of the invention also include nitrosated compounds of formula (I) that have been nitrosated through one or more sites such as oxygen (hydroxyl condensation), sulfur (sulfhydryl condensation) and/or nitrogen. The nitrosated compounds of the present invention can be prepared using conventional methods known to one skilled in the art. For example, known methods for nitrosating compounds are described in U.S. Pat. Nos. 5,380,758, 5,703,073, 5,994,294, 6,242,432 and 6,218,417; WO 98/19672; and Oae et al., Org. Prep. Proc. Int., 15(3): 165-198 (1983).

Salts are preferably the pharmaceutically acceptable salts of the compounds of formula (I). The expression "pharmaceutically acceptable salts" encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, palmoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or, in case the compound of formula (I) is acidic in nature, with an inorganic base like an alkali or earth alkali base, e.g. sodium hydroxide, potassium hydroxide, calcium hydroxide and the like. For other examples of pharmaceutically acceptable salts, reference can be made notably to "Salt selection for basic drugs", *Int. J. Pharm.* (1986), 33, 201-217.

The invention also includes derivatives of the compound of Formula I, acting as prodrugs. These prodrugs, following administration to the patient, are converted in the body by normal metabolic processes to the compound of Formula 1. Such prodrugs include those that demonstrate enhanced bioavailability (see Table 4 below), tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The general terms used hereinbefore in formula I and hereinafter preferably have, within this disclosure, the following meanings, unless otherwise indicated. Where the plural form is used for compounds, salts, pharmaceutical compositions, diseases and the like, this is intended to mean also a single compound, salt, or the like.

The term "alkyl", alone or in combination with other groups, means saturated, straight and branched chain groups with one to six carbon atoms, i.e., $C_{1-6}$ alkyl. Examples of alkyl groups are methyl, ethyl, n-propyl, iso-propyl, n-butyl, iso-butyl, sec-butyl, tert-butyl, pentyl, hexyl and heptyl. The methyl, ethyl and isopropyl groups are preferred. Structural depictions of compounds may show a terminal methyl group as "—CH$_3$", "Me", or "$\xi$" i.e., these have equivalent meanings.

The term "alkoxy", alone or in combination with other groups, refers to an R—O— group, wherein R is an alkyl group. Examples of alkoxy groups are methoxy, ethoxy, propoxy, iso-propoxy, iso-butoxy, sec-butoxy and tert-butoxy.

The term "hydroxy-alkyl", alone or in combination with other groups, refers to an HO—R— group, wherein R is an alkyl group. Examples of hydroxy-alkyl groups are HO—CH$_2$—, HO—CH$_2$CH$_2$—, HO—CH$_2$CH$_2$CH$_2$— and CH$_3$CH(OH)—.

The term "halogen" means fluorine, chlorine, bromine or iodine, preferably fluorine, chlorine or bromine, especially fluorine or chlorine.

The term "cycloalkyl", alone or in combination, means a saturated cyclic hydrocarbon ring system with 3 to 8 carbon atoms, e.g. cyclopropyl, cyclobutyl, cyclopentyl, cyclohexyl, cycloheptyl and cyclooctyl.

The term "aryl", alone or in combination, relates to a phenyl, naphthyl or indanyl group, preferably a phenyl group.

The term "heteroaryl", alone or in combination, means six-membered aromatic rings containing one to four nitrogen atoms; benzofused six-membered aromatic rings containing one to three nitrogen atoms; five-membered aromatic rings containing one oxygen, one nitrogen or one sulfur atom; benzofused five-membered aromatic rings containing one oxygen, one nitrogen or one sulfur atom; five-membered aromatic rings containing two heteroatoms independently selected from oxygen, nitrogen and sulfur and benzofused derivatives of such rings; five-membered aromatic rings containing three nitrogen atoms and benzofused derivatives thereof; a tetrazolyl ring; a thiazinyl ring; or coumarinyl. Examples of such ring systems are furanyl, thienyl, pyrrolyl, pyridinyl, pyrimidinyl, indolyl, quinolinyl, isoquinolinyl, imidazolyl, triazinyl, thiazolyl, isothiazolyl, pyridazinyl, pyrazolyl, oxazolyl, isoxazolyl, benzothienyl, quinazolinyl and quinoxalinyl.

In one embodiment of the invention, Q is methylene, and all other variables are as previously defined.

In another embodiment of the invention, $R^1$ is cyclopropyl, and all other variables are as previously defined.

In another embodiment of the invention, W is phenyl substituted by V in the para position, and all other variables are as previously defined.

In another embodiment of the invention, V is —CH$_2$CH$_2$O—, —CH$_2$CH$_2$CH$_2$O—, or —OCH$_2$CH$_2$O—, wherein the bivalent radical is linked to the group U of formula (I) via an oxygen atom. In a preferred group of this embodiment, V is —OCH$_2$CH$_2$O—, and all other variables are as previously defined.

In another embodiment of the invention, U is a mono-, di-, tri-or tetra-substituted aryl. In a preferred group of this embodiment, U is a mono-, di-, or tri-substituted phenyl wherein the substituents are independently selected from the group consisting of halogen, $C_1$-$C_6$ alkyl, $C_1$-$C_6$ alkoxy, and —CF$_3$. In a more preferred group of this embodiment, the substituents are independently selected from the group consisting of halogen and $C_1$-$C_6$ alkyl. In an even more preferred embodiment, U represents 2,6-dichloro-4-methyl-phenyl, and all other variables are as previously defined.

In another embodiment of the invention, $R^2$ is —O(CH$_2$)$_2$OCH$_3$ or —(CH$_2$)$_3$OCH$_3$, and all other variables are as previously defined.

In another embodiment of the invention, $R^3$ is selected from the group consisting of:

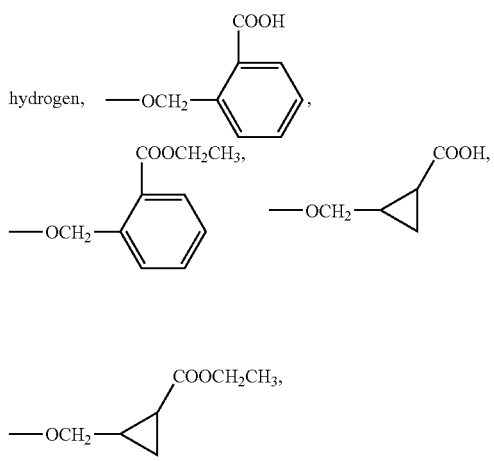

—OCH$_2$CH$_2$C(CH$_3$)$_2$C(O)OCH$_3$, and —OCH$_2$CH$_2$C(CH$_3$)$_2$C(O)OH, and all other variables are as previously defined In another embodiment of the invention, $R^7$ and $R^8$ are independently selected from the group consisting of:
hydrogen,
—CH$_3$,
—CH$_2$CH$_3$,
—OH,
—OCH$_3$,
—COOH,
—NH$_2$, and

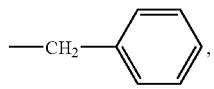

or $R^7$ and $R^8$, together with the atom to which they are attached, form a cycloalkyl ring selected from the group consisting of cyclopropyl, cyclobutyl, cyclopentyl, and cyclohexyl, and all other variables are as previously defined.

In another embodiment of the invention, $R^4$ is selected from the group consisting of:
hydrogen,
—C(O)OCH$_3$,
—COOH,

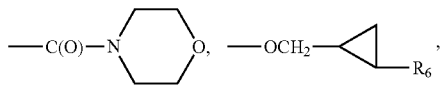

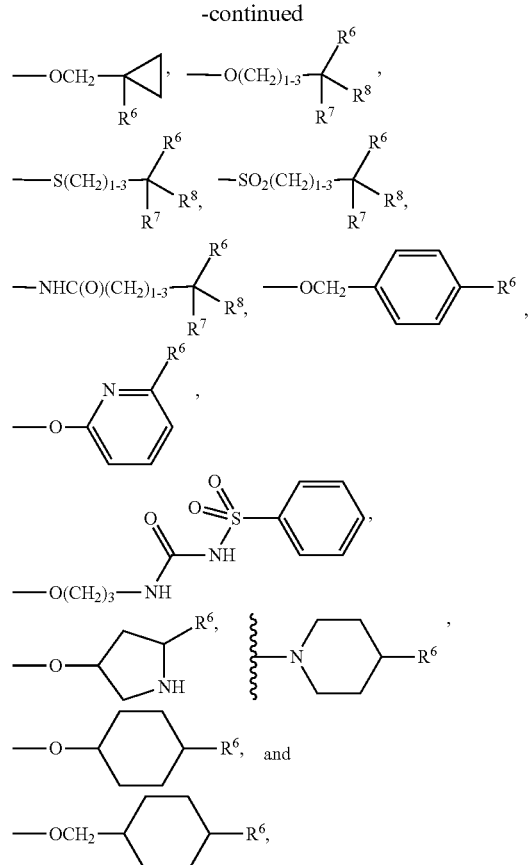
and all other variables are as previously defined.
Specific examples of compounds of formula I, and pharmaceutically acceptable salts thereof, include those listed in the following tables:
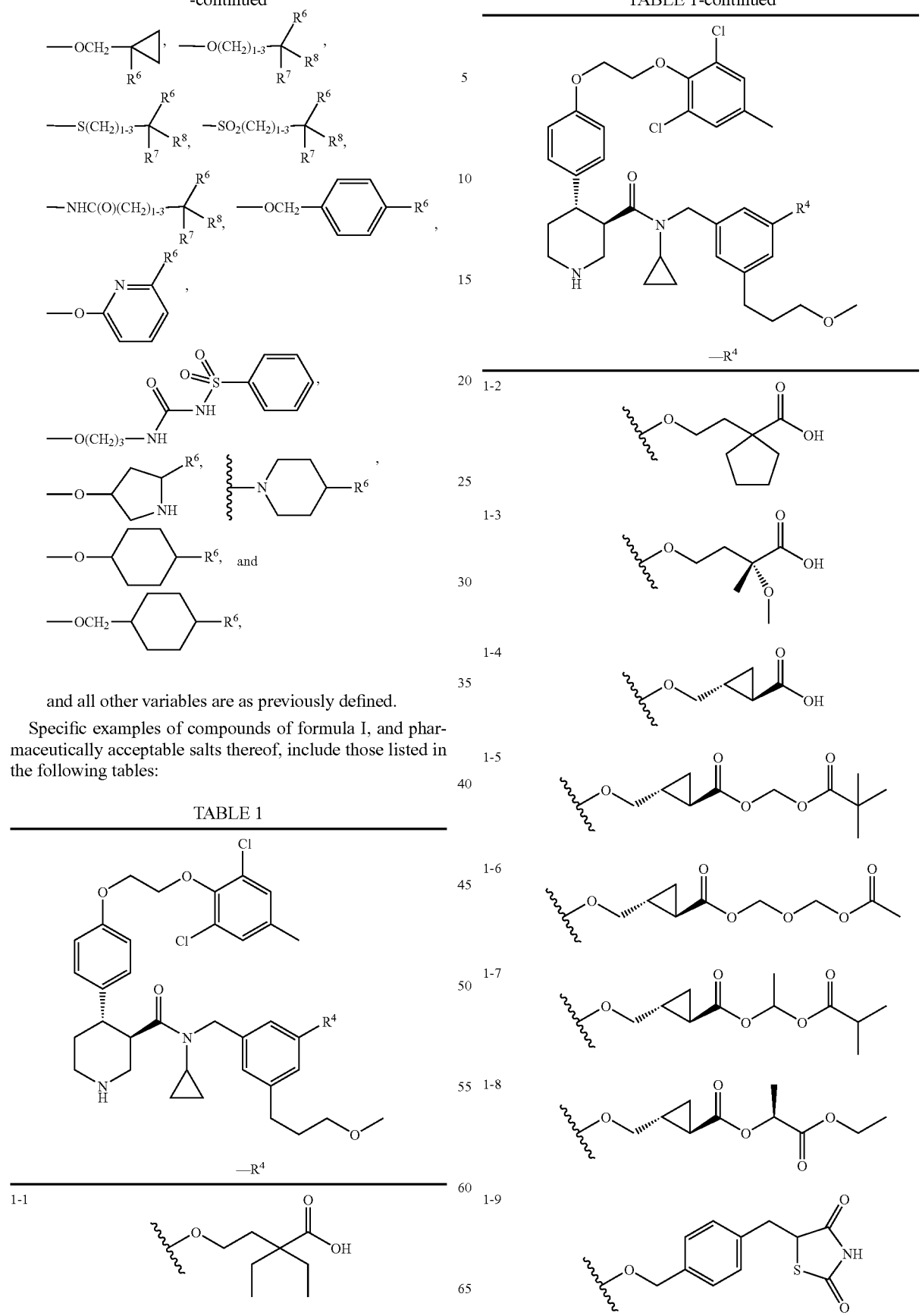

TABLE 1-continued
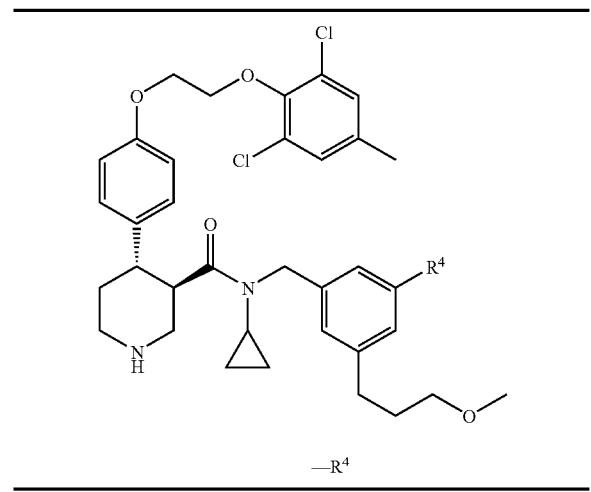
—R⁴
1-10 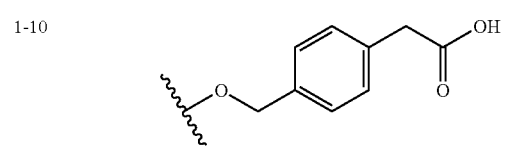
1-11 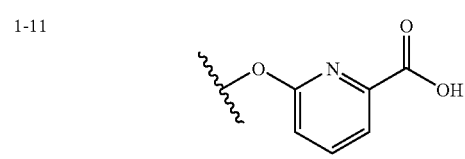
1-12 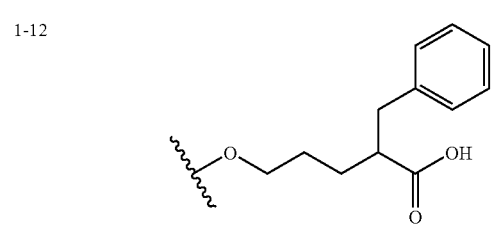
1-13 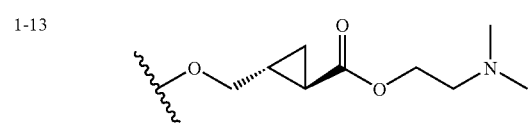
1-14 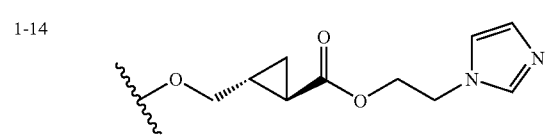
1-15 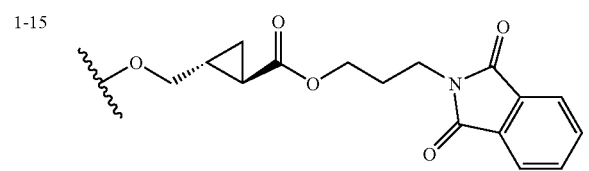
1-16 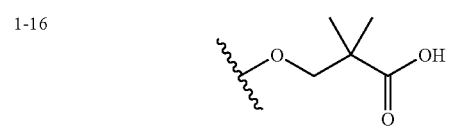
TABLE 1-continued
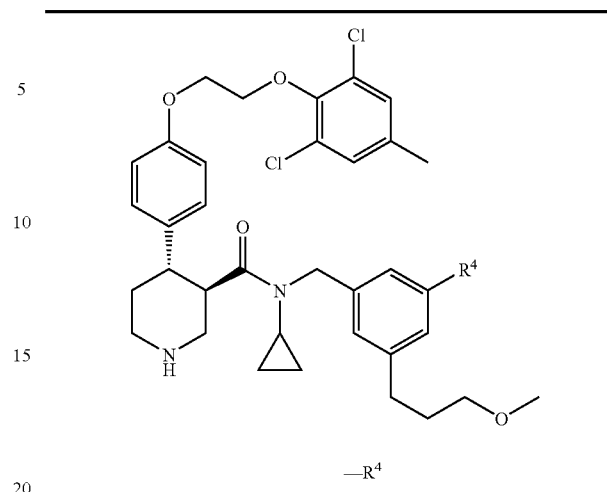
—R⁴
1-17 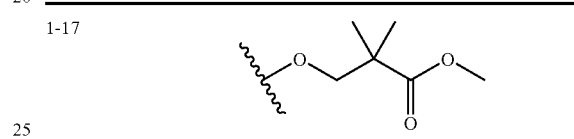
1-18 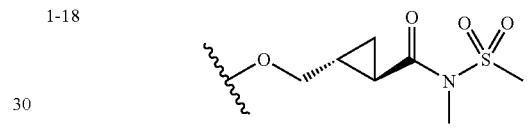
1-19 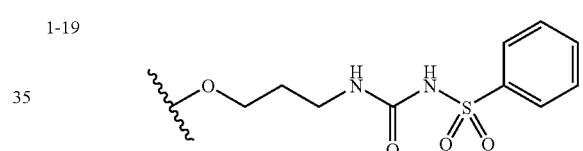
1-20 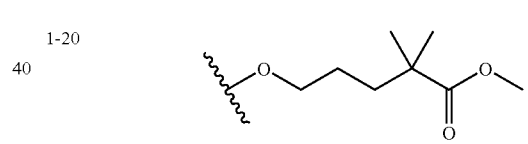
1-21 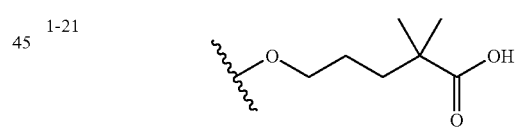
1-22 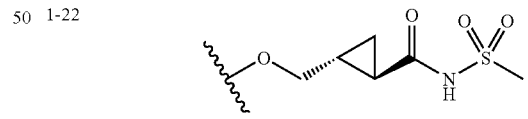
1-23 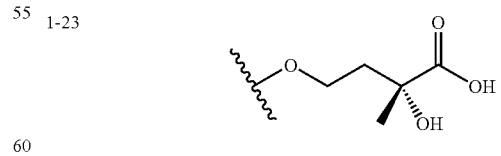
1-24 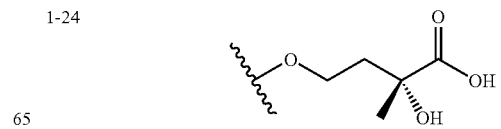

TABLE 1-continued
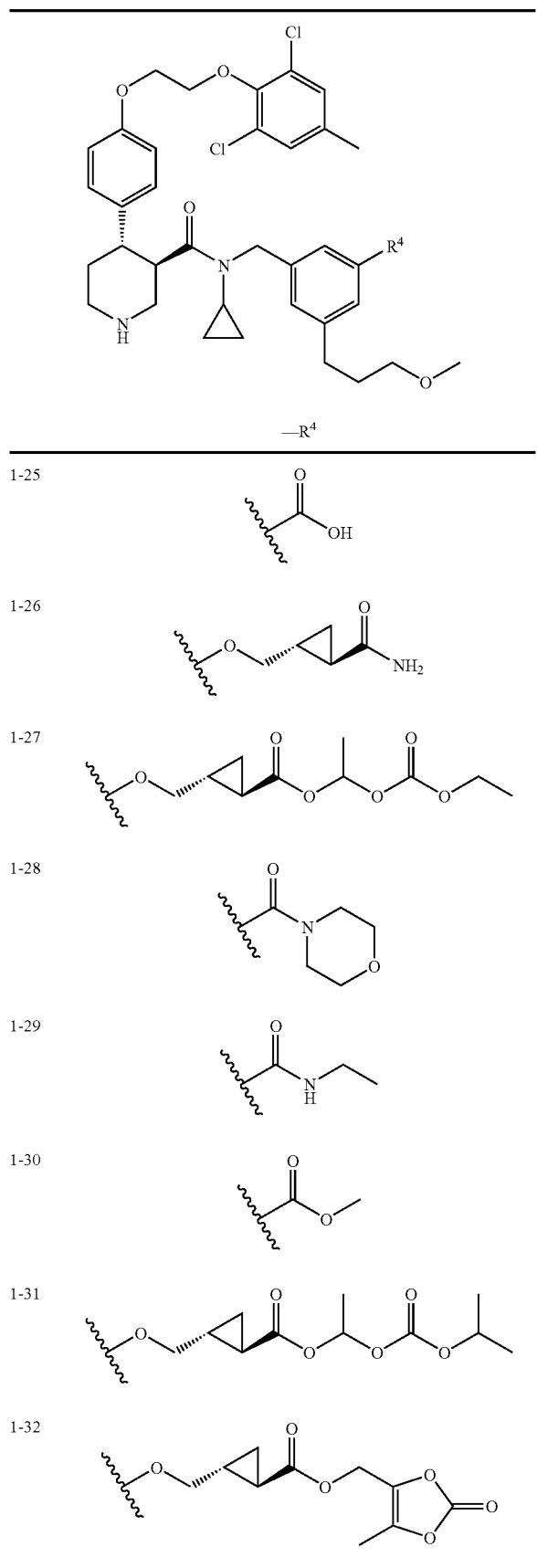
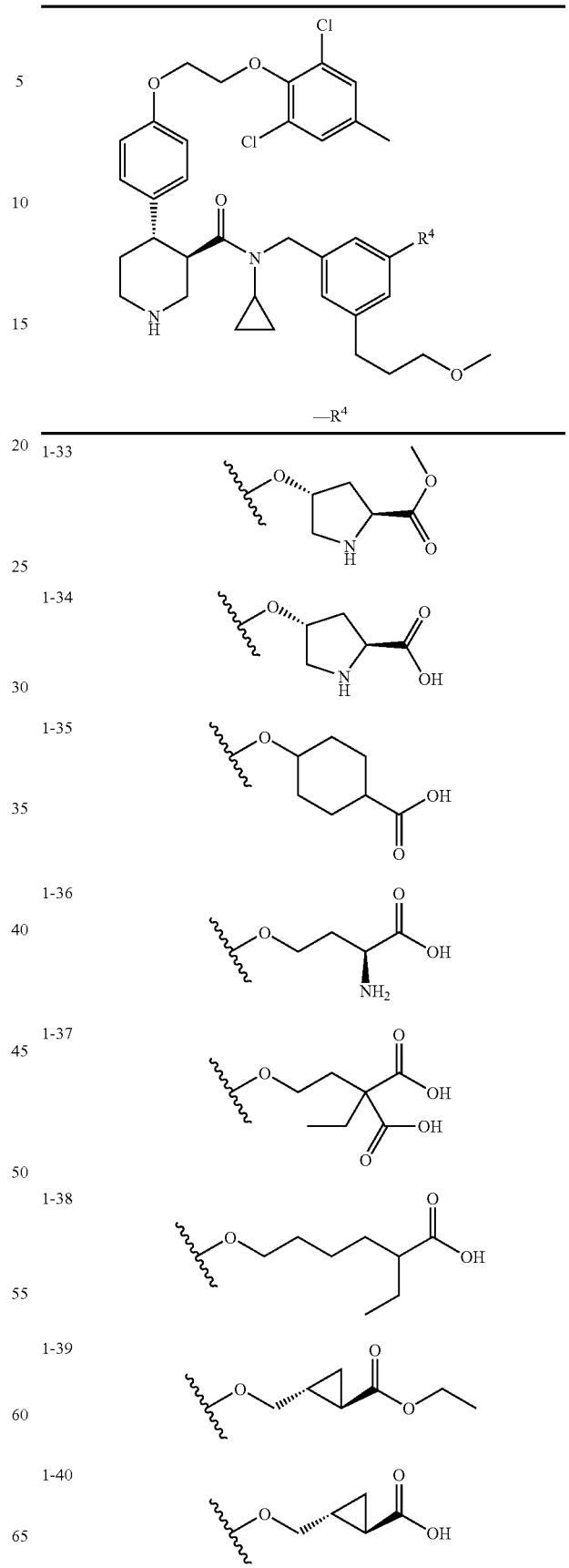

TABLE 1-continued
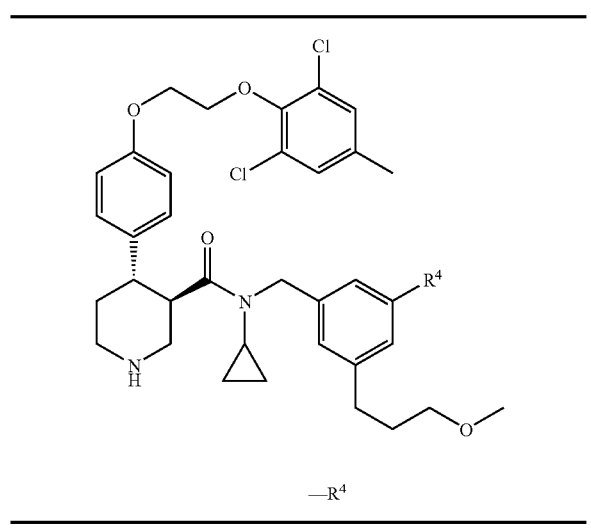
—R⁴
| | |
|---|---|
| 1-41 | 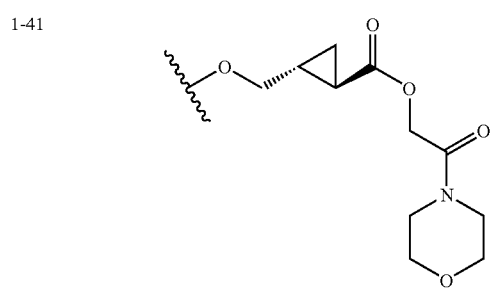 |
| 1-42 | 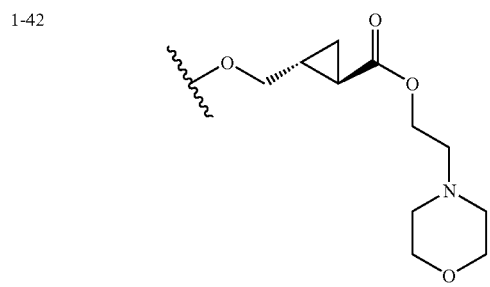 |
| 1-43 | 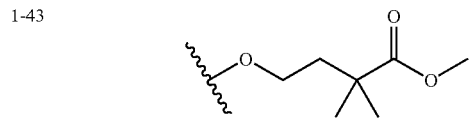 |
| 1-44 | 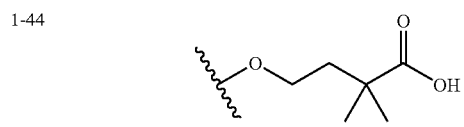 |
| 1-45 | 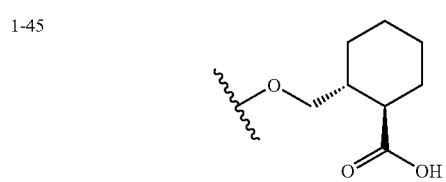 |
TABLE 1-continued
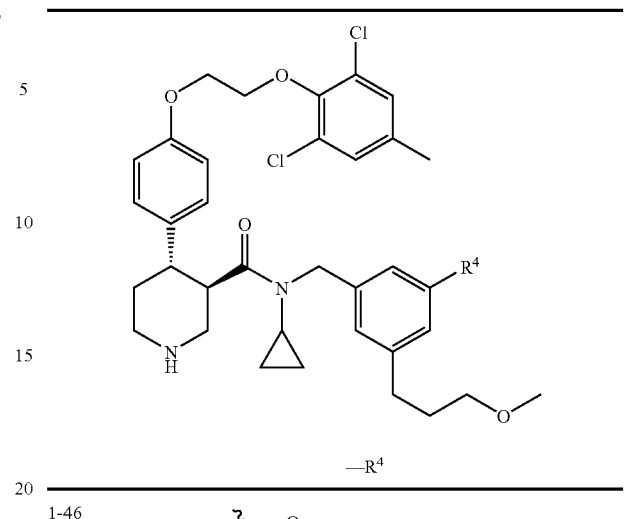
—R⁴
| | |
|---|---|
| 1-46 | 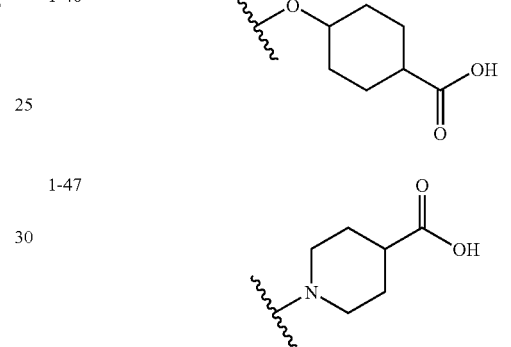 |
| 1-47 | |
| 1-48 | |
| 1-49 | |
| 1-50 | |
| 1-51 | |
| 1-52 | |

TABLE 1-continued
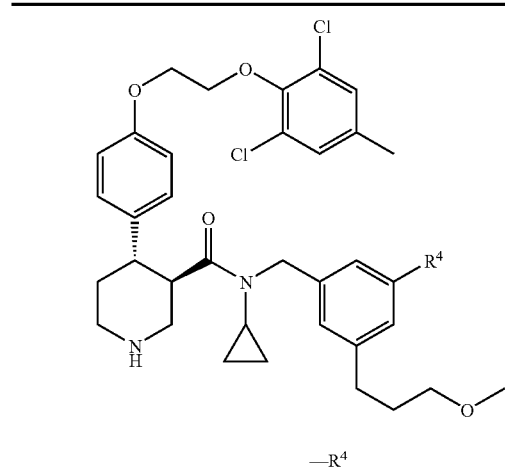
—R⁴
1-53 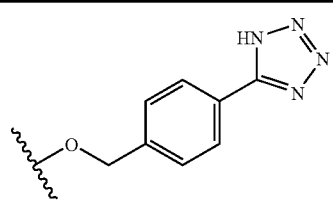
1-54 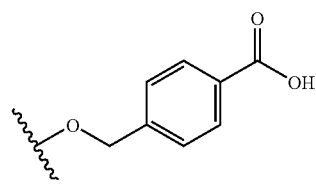 [SMILES: *OCc1ccc(C(=O)O)cc1]
1-55 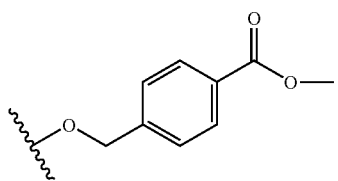 [SMILES: *OCc1ccc(C(=O)OC)cc1]
1-56 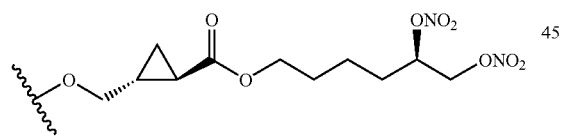
1-57 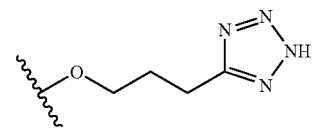 [SMILES: *OCCCc1nn[nH]n1]
1-58 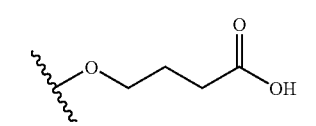 [SMILES: *OCCCC(=O)O]
1-59 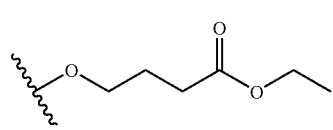 [SMILES: *OCCCC(=O)OCC]
TABLE 1-continued
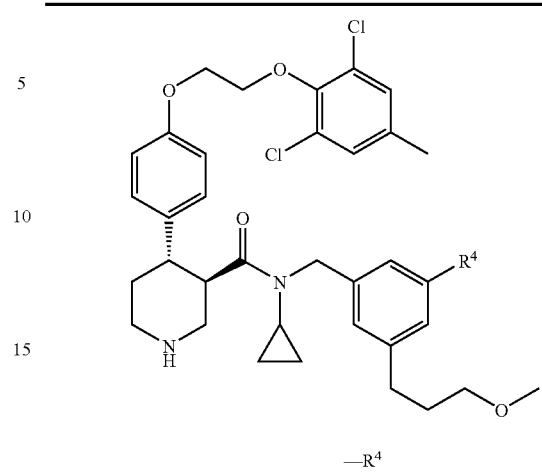
—R⁴
1-60 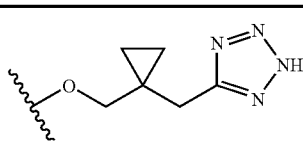
1-61 
1-62 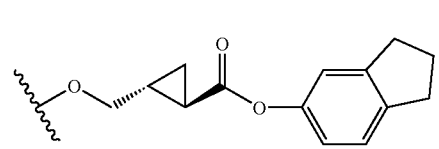 [SMILES: *OC[C@@H]1C[C@H]1C(=O)Oc1ccc2c(c1)CCC2]
1-63 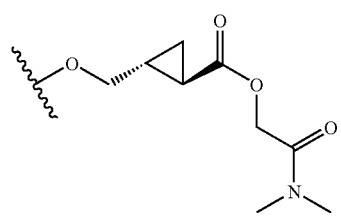 [SMILES: *OC[C@@H]1C[C@H]1C(=O)OCC(=O)N(C)C]
1-64 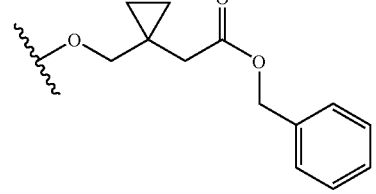
1-65 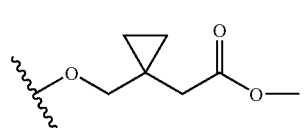 [SMILES: *OCC1(CC(=O)OC)CC1]
1-66 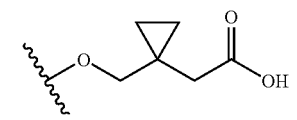 [SMILES: *OCC1(CC(=O)O)CC1]

TABLE 2
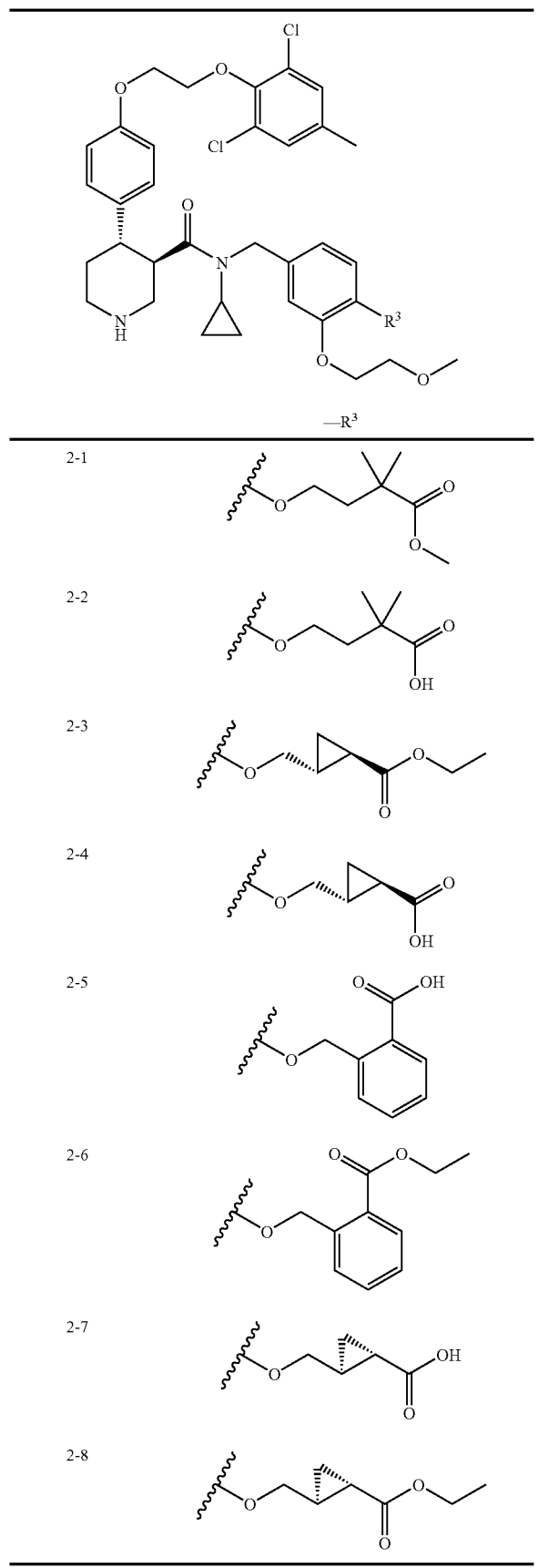
TABLE 3
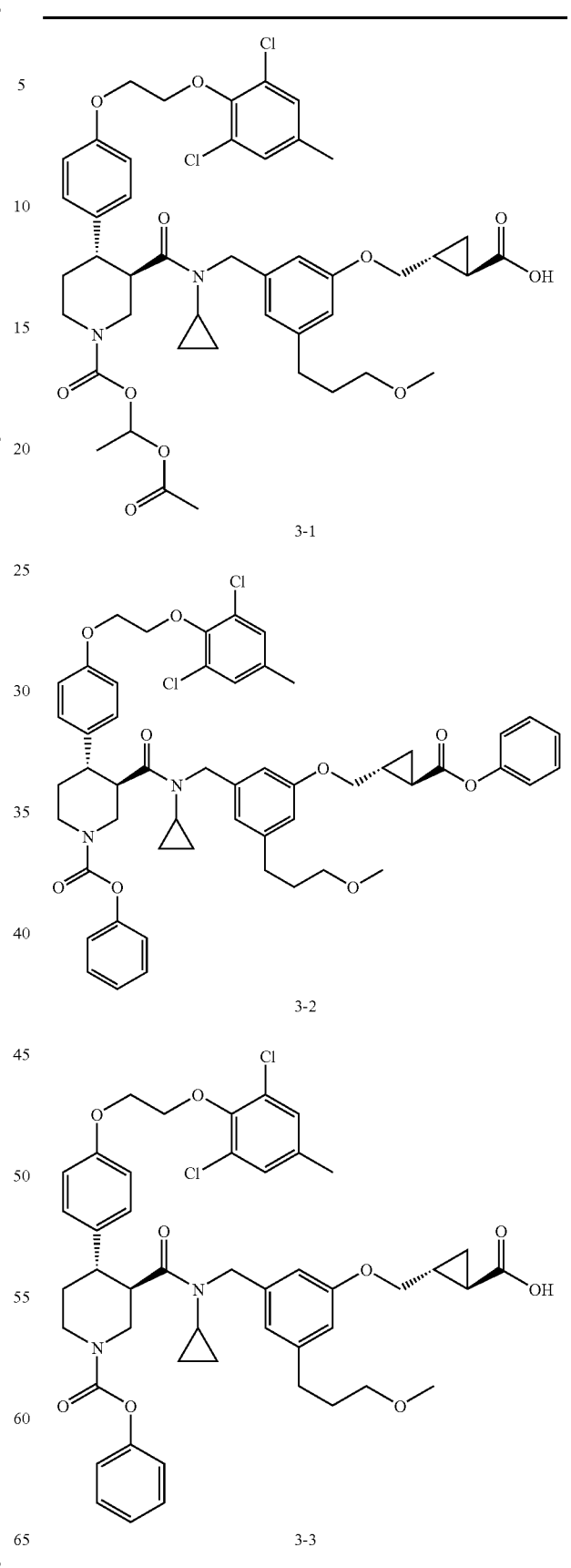

TABLE 3-continued
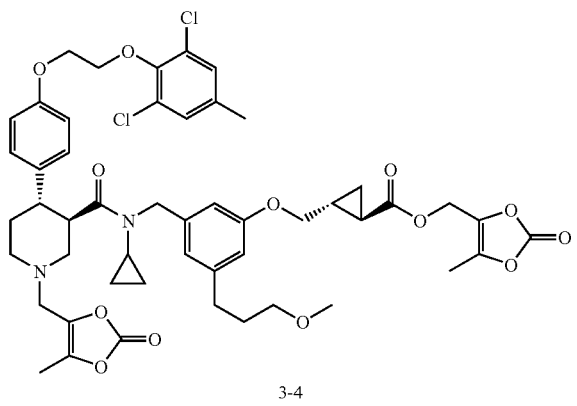
3-4
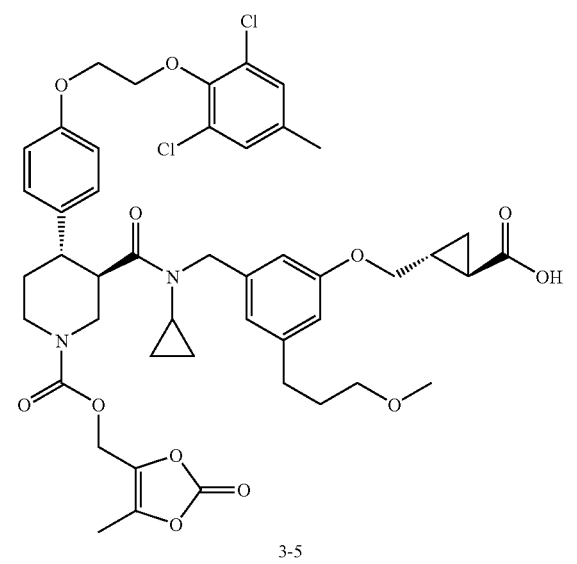
3-5
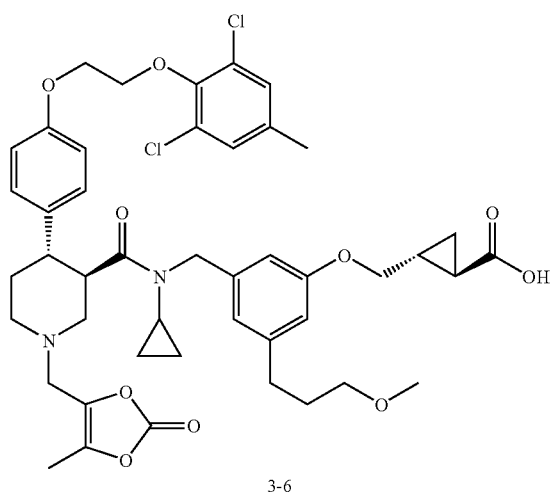
3-6
TABLE 3-continued
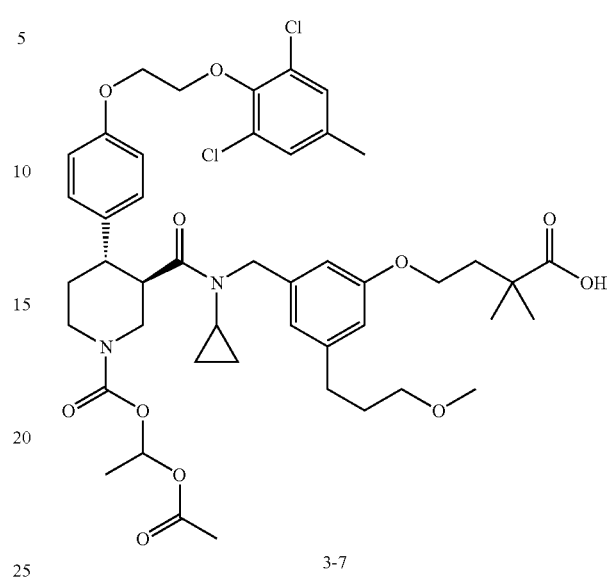
3-7
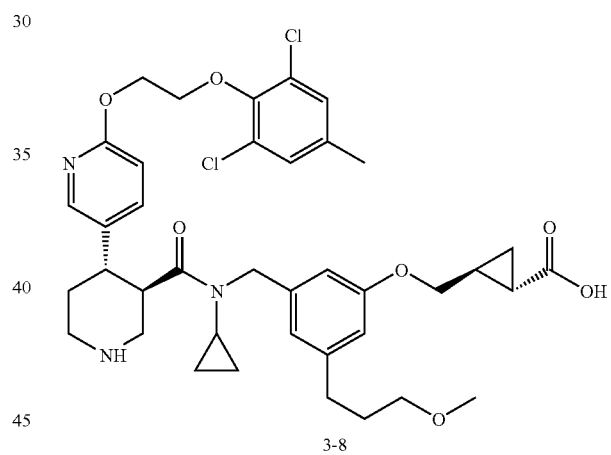
3-8
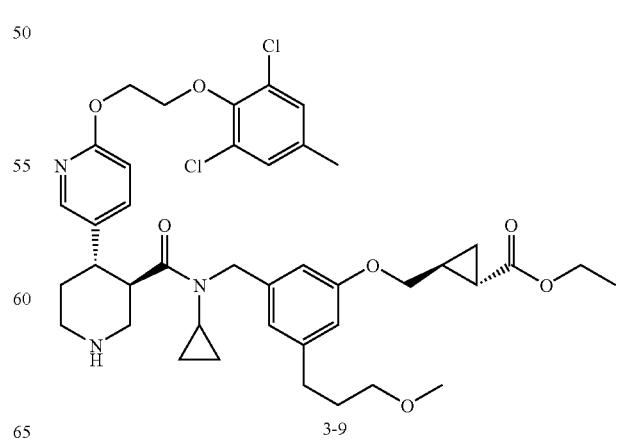
3-9

TABLE 3-continued

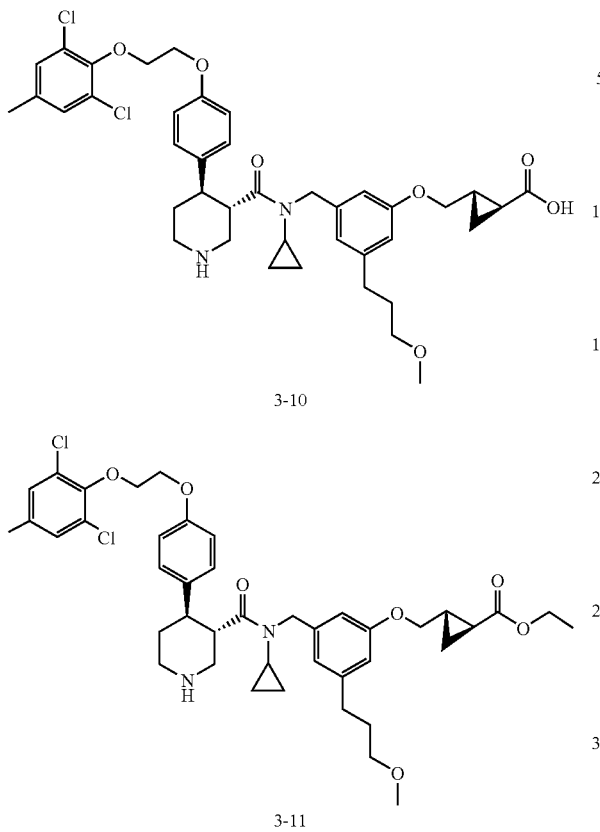

3-10

3-11

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

LIST OF ABBREVIATIONS

ABTS  2,2'-Azino-bis(3-ethylbenzthiazoline-6-sulfonic Acid).2NH$_3$
Boc t-butyloxycarbonyl
BSA bovine serum albumin
DCM dichloromethane
DME dimethoxyethane
DMF dimethylformamide
DMSO dimethylsulfoxide
EDTA ethylenediaminetetraacetic acid
EIA enzyme immunoassay
HATU O-(7-azabenzotriazol-1-yl)-N,N,N',N'-tetramethyluronium hexafluorophosphate
PBS phosphate-buffered saline
TBS tert-butyldimethylsilyl
TBSO tert-butyldimethylsilyloxy
TFA trifluoroacetic acid
THF tetrahydrofuran Unless expressly stated to the contrary, all ranges cited herein are inclusive. For example, an alkyl group described as C$_1$-C$_6$ alkyl means the alkyl group can contain 1, 2, 3, 4, 5 or 6 carbon atoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono-and poly-substitution by a named substituent to the extent such single and multiple substitution (including multiple substitution at the same site) is chemically allowed.

In compounds of the invention having pyridyl N-oxide moieties, the pyridyl-N-oxide portion is structurally depicted using conventional representations such as

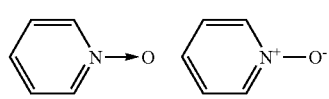

which have equivalent meanings.

The invention relates to a method for the treatment and/or prophylaxis of diseases which are related to hypertension, congestive heart failure, pulmonary hypertension, systolic hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, which method comprises administrating a compound as defined above to a human being or animal.

In another embodiment, the invention relates to a method for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In another embodiment, the invention relates to a method for the treatment and/or prophylaxis of diseases, which are associated with a dysregulation of the renin-angiotensin system as well as for the treatment of the above-mentioned diseases.

The invention also relates to the use of compounds of formula (I) for the preparation of a medicament for the treatment and/or prophylaxis of the above-mentioned diseases.

Compounds of formula (I) or the above-mentioned pharmaceutical compositions are also of use in combination with other pharmacologically active compounds comprising ACE-inhibitors, neutral endopeptidase inhibitors, angiotensin II receptor antagonists, endothelin receptors antagonists, vasodilators, calcium antagonists, potassium activators, diuretics, sympatholytics, beta-adrenergic antagonists, alpha-adrenergic antagonists or with other drugs beneficial for the prevention or the treatment of the above-mentioned diseases.

The term "administration" and variants thereof (e.g., "administering" a compound) in reference to a compound of Formula I mean providing the compound or a prodrug of the compound to the individual in need of treatment or prophylaxis. When a compound of the invention or a prodrug thereof is provided in combination with one or more other active agents (e.g., an agent such as anangiotensin II receptor antagonist, ACE inhibitor, or other active agent which is known to reduce blood pressure), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit renin and thereby elicit the response being sought (i.e., an "inhibition effective amount"). When the active compound (i.e., active ingredient) is administered as the salt, references to the amount of active ingredient are to the free form (i.e., the non-salt form) of the compound.

In a preferred embodiment, this amount is comprised between 1 mg and 1000 mg per day. In a particularly preferred embodiment, this amount is comprised between 1 mg and 500 mg per day. In a more particularly preferred embodiment, this amount is comprised between 1 mg and 200 mg per day.

In the method of the present invention (i.e., inhibiting renin), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990.

Assays Demonstrating Biological Activity

Inhibition of Human Recombinant Renin

The enzymatic in vitro assay was performed in 384-well polypropylene plates (Nunc). The assay buffer consisted of PBS (Gibco BRL) including 1 mM EDTA and 0.1% BSA. The reaction mixture were composed of 47.5 µL per well of an enzyme mix and 2.5 µL of renin inhibitors in DMSO. The enzyme mix was premixed at 4° C. and consists of the following components:
human recombinant renin (40 pM)
synthetic human angiotensin(1-14) (0.5 µM)
hydroxyquinoline sulfate (1 mM)

The mixtures were then incubated at 37° C. for 3 h. The enzyme reaction was stopped by placing the reaction plate on wet ice.

To determine the enzymatic activity and its inhibition, the accumulated Ang I was detected by an enzyme immunoassay (EIA) in 384-well plates (Nunc). 5 µL of the reaction mixture or standards were transferred to immuno plates which were previously coated with a covalent complex of Ang I and bovine serum albumin (Ang I-BSA). 75 µL of Ang I-antibodies in assay buffer above including 0.01% Tween 20 were added and the plates were incubated at 4° C. overnight.

An alternative protocol could be used by stopping the enzymatic reaction with 0.02N final concentration of HCl. 5 µL of the reaction mixture or standards were transferred to immuno plates and 75 µL of Ang I-antibodies in assay buffer above including 0.01% Tween 20 were added and the plates were incubate at RT for 4 h.

The plates were washed 3 times with PBS including 0.01% Tween 20, and then incubated for 2 h at RT with an anti rabbit-peroxidase coupled antibody (WA 934, Amersham). After washing the plates 3 times, the peroxidase substrate ABTS ((2,2'-Azino-bis(3-ethylbenzthiazoline-6-sulfonic Acid).2NH$_3$) was added and the plates incubated for 60 min at RT. The plate was evaluated in a microplate reader at 405 nm. The percentage of inhibition was calculated for each concentration point and the concentration of renin inhibition was determined that inhibited the enzyme activity by 50% (IC$_{50}$). The IC$_{50}$-values of all compounds tested were below 1 µM.

Inhibition of Renin in Human Plasma

The enzymatic in vitro assay was performed in 384-well polypropylene plates (Nunc). The assay buffer consisted of PBS (Gibco BRL) including 1 mM EDTA and 0.1% BSA. The reaction mixture was composed of 80 µL per well of human plasma, enzyme, Ang I-antibodies mix and 5 µL of renin inhibitors in DMSO. The human plasma mix was premixed at 4° C. and consists of
human plasma from 10 normal donors
human recombinant renin (3 pM)
Ang I-antibodies.

The mixtures were then incubated at 37° C. for 2 h.

To determine the enzymatic activity and its inhibition, the accumulated Ang I was detected by an enzyme immunoassay (EIA) in 384-well plates (Nunc). 10 μL of the reaction mixture or standards were transferred to immuno plates which were previously coated with a covalent complex of Ang I and bovine serum albumin (Ang I-BSA). 70 μL assay buffer were added and the plates were incubated at 4° C. overnight. The plates were washed 3 times with PBS including 0.01% Tween 20, and then incubated for 2 h at RT with an anti rabbit-peroxidase coupled antibody (WA 934, Amersham). After washing the plates 3 times, the peroxidase substrate ABTS ((2,2'-Azino-bis(3-ethylbenzthiazoline-6-sulfonic Acid).2NH$_3$) was added and the plates incubated for 60 min at RT. The plate was evaluated in a microplate reader at 405 nm. The percentage of inhibition was calculated of each concentration point and the concentration of renin inhibition was determined that inhibited the enzyme activity by 50% (IC$_{50}$). The IC$_{50}$-values of all compounds tested were below 10 μM.

In vivo animal model—Female double transgenic rats were purchased from RCC Ltd, Füllingsdorf, Switzerland. All animals were maintained under identical conditions and had free access to normal pelleted rat chow and water. Rats were initially treated with enalapril (1 mg/kg/day) during 2 months. After approximately two weeks following cessation of enalapril treatment the double transgenic rats become hypertensive and reach mean arterial pressures in the range of 160-170 mmHg Transmitter implantation—The rats were anaesthetised with a mixture of 90 mg/kg Ketamin-HCl (Ketavet, Parke-Davis, Berlin FRG) and 10 mg/kg xylazin (Rompun, Bayer, Leverkusen, FRG) i.p. The pressure transmitter was implanted under aseptic conditions into the peritoneal cavity with the sensing catheter placed in the descending aorta below the renal arteries pointing upstream. The transmitter was sutured to the abdominal musculature and the skin closed.

Telemetry-System—Telemetry units were obtained from Data Sciences (St. Paul, Minn.). The implanted sensor consisted of a fluid-filled catheter (0.7 mm diameter, 8 cm long; model TA11PA-C40) connected to a highly stable low-conductance strain-gauge pressure transducer, which measured the absolute arterial pressure relative to a vacuum, and a radio-frequency transmitter. The tip of the catheter was filled with a viscous gel that prevents blood reflux and was coated with an antithrombogenic film to inhibit thrombus formation. The implants (length=2.5 cm, diameter=1.2 cm) weighted 9 g and have a typical battery life of 6 months. A receiver platform (RPC-1, Data Sciences) connected the radio signal to digitized input that was sent to a dedicated personal computer (Compaq, deskpro). Arterial pressures were calibrated by using an input from an ambient-pressure reference (APR-1, Data Sciences). Systolic, mean and diastolic blood pressure was expressed in millimeter of mercury (mmHg).

Hemodynamic measurements —Double transgenic rats with implanted pressure transmitters were dosed by oral gavage with vehicle or 10 mg/kg of the test substance (n=6 per group) and the mean arterial blood pressure was continuously monitored. The effect of the test substance is expressed as maximal decrease of mean arterial pressure (MAP) in the treated group versus the control group.

Methods of Synthesis

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2.sup.nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes and examples are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specifically stated otherwise, the experimental procedures were performed under the following conditions. Evaporation of solvent was carried out using a rotary evaporator under reduced pressure (600-4000 pascals: 4.5-30 mm Hg) with a bath temperature of up to 60° C. Reactions are typically run under nitrogen atmosphere at ambient temperature if not otherwise mentioned. Anhydrous solvent such as THF, DMF, Et$_2$O, DME and Toluene are commercial grade. Reagents are commercial grade and were used without further purification. Flash chromatography is run on silica gel (230-400 mesh). The course of the reaction was followed by either thin layer chromatography (TLC) or nuclear magnetic resonance (NMR) spectrometry and reaction times given are for illustration only. The structure and purity of all final products were ascertained by TLC, mass spectrometry, $^1$H NMR and high-pressure liquid chromatography (HPLC). Chemical symbols have their usual meanings. The following abbreviations have also been used: v (volume), w (weight), b.p. (boiling point), m.p. (melting point), L (liter(s)), mL (milliliter(s)), g (gram(s)), mg (milligram(s)), mol (mole(s)), mmol (millimole(s)), eq. (equivalent(s)). Unless otherwise specified, all variables mentioned below have the meanings as provided above.

Compounds of the present invention can be prepared according to the following general methods as exemplified in Scheme 1. For example, palladium-medium Suzuki coupling between triflate II and boronic acid III can provide α,β-unsaturated ester IV. Reduction of the alkene group in IV can be accomplished using reducing agents such as magnesium. The resulting saturated piperidine V are obtained as a mixture of cis-and trans-diastereomers, which can be equilibrated to the trans-diastereomer VI by refluxing in ethanol in presence of sodium ethoxide. Saponification of ester VI and coupling of the resulting acid VII with amine VIII will provide piperidine IX. Removal of the TBS group, followed by introduction of R$^4$ appendage on aminoamide IX affords piperidine XI. Finally, removal of the protecting group can provide the desired piperidine XII.

Scheme 1
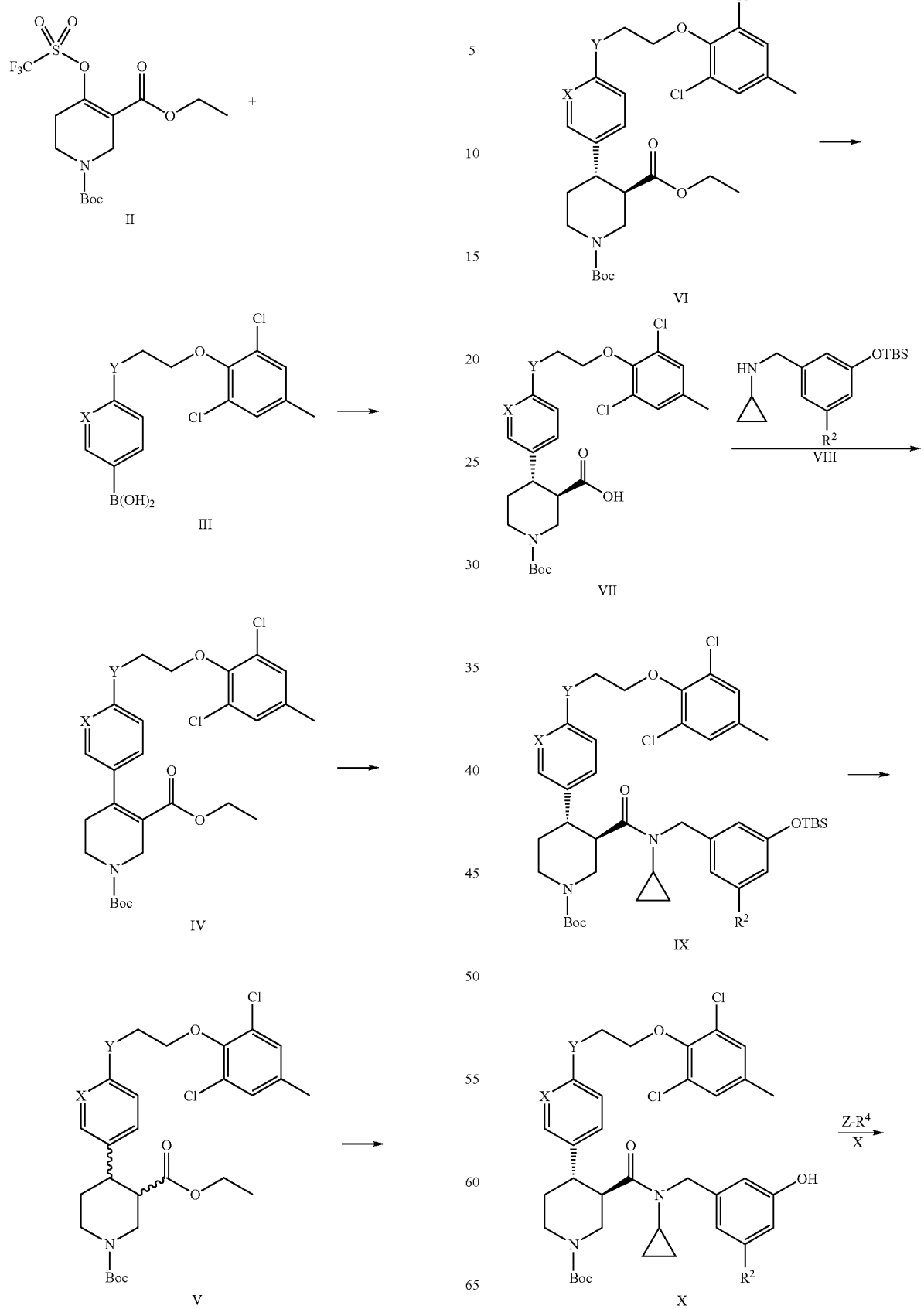

-continued

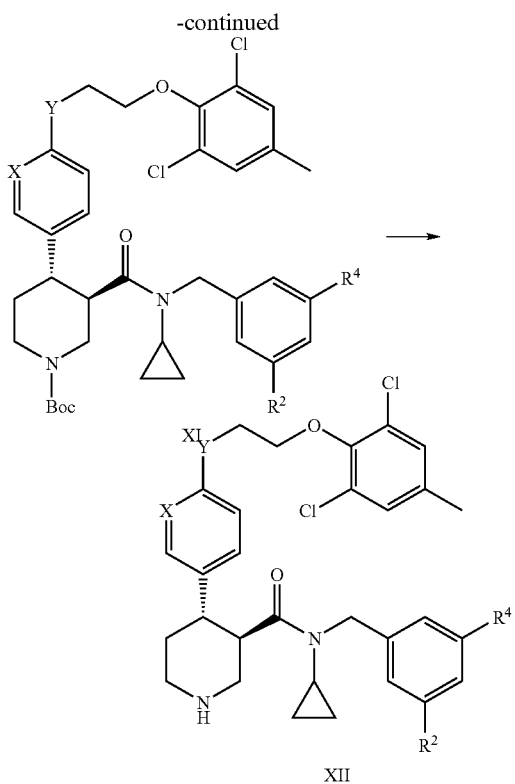

X is CH or N; Y is O or $CH_2$, $R^2$ is as described above. Z is a synthetically feasible leaving group selected from but not limited to Cl, —$OSO_2CF_3$, and OH. $R^4$ is any one of the groups defined above for $R^4$ where "O" is the atom attached to the phenyl 3-position. Alternatively, in the case where $R^4$ is a group having a "non-O" atom linkage (e.g., "C", "S" or "N"), compound VII is converted to compound IX using an intermediate having the formula

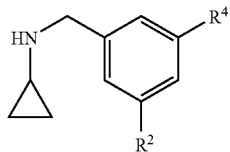

where $R^2$ is as described above and $R^4$ is one of the groups defined for $R^4$ where "C", "S" or "N" is the atom attached to the phenyl 3-position.

Triflate II

| Compound | Structure |
|---|---|
| Triflate 1 | 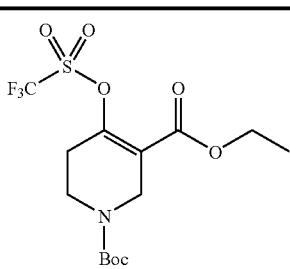 |

Triflate 1

Step 1: 1-tert-Butyl 3-ethyl 4-oxopiperidine-1,3-dicarboxylate

To a solution of ethyl 4-oxopiperidine-3-carboxylate hydrogen chloride (1 eq.) in tert-butyl methyl ether (0.85 M) at 0° C. was added di-tert-butyl dicarbonate (1.5 eq.) and 1N aqueous NaOH (1.5 eq.). The reaction was warmed to rt and stirred for 18 h. The reaction was neutralized with 10% aqueous HCl and extracted with ether. The combined organic extracts were washed with brine, dried over $MgSO_4$, and concentrated in vacuo to afford the title compound as a solid.

Step 2: 1-tert-Butyl-3-ethyl-4-{[(trifluoromethyl)sulfonyl]oxy}-5,6-dihydropyridine-1,3(2H)-dicarboxylate To a solution of 1-tert-butyl 3-ethyl 4-oxopiperidine-1,3-dicarboxylate (1 eq.) from the previous step in THF (0.2 M) at 0° C. was added NaH (1 eq.) portionwise. After stirring for 5 min, 1,1,1-trifluoro-N-phenyl-N-[(trifluoromethyl)sulfonyl]-methanesulfonamide (1.05 eq.) was added and the reaction was stirred for 20 h at rt. The reaction mixture was quenched with saturated aqueous $NH_4Cl$ solution and extracted with ether. The combined organic extracts were washed with brine, dried over $MgSO_4$, and concentrated in vacuo. The crude mixture was purified by flash column chromatography ($SiO_2$, 10%→15% EtOAc in Hex) to afford the title compound as a yellow oil.

Boronic Acid III

| Compound | Structure |
|---|---|
| Boronic acid 1 | 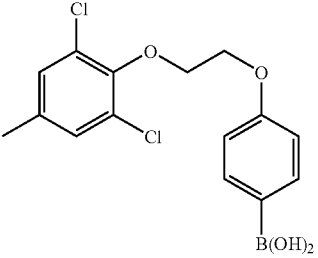 [SMILES: Cc1cc(Cl)c(OCCOc2ccc(B(O)O)cc2)c(Cl)c1] |

Boronic Acid 1

Step 1: 1,3-Dichloro-2-(2-chloroethoxy)-5-methylbenzene

To a solution of 4-bromophenol (1 eq.) in dichloroethane/water (4:1 v/v, 0.38 M) was added 10 N NaOH (5 eq.) and catalytic amount of tetrabutylammonium hydrogen sulfate (2 mol %). The reaction was refluxed for 16 h. The aqueous phase was extracted with dichloroethane. The combined organic extracts were washed with saturated aqueous $NH_4Cl$, dried over $Na_2SO_4$, and concentrated in vacuo. The residue was suspended in heptane and filtered to give the title compound as a white solid.

Step 2: 2-[2-(4-Bromophenoxy)ethoxy]-1,3-dichloro-5-methylbenzene 1,3-Dichloro-2-(2-chloroethoxy)-5-methylbenzene (1.05 eq.) from the previous step and potassium carbonate (1.1 eq.)

were dissolved in DMF (0.5 M) and heated to 100° C. A solution of 2,6-dichloro-4-methylphenol (1 eq.) in DMF was added dropwise over 1 h (final concentration 0.38M). The reaction was stirred at 100° C. for 2 h. After cooling to 40° C., equal volume of water was added to the reaction. The resulting precipitate was filtered and washed extensively with DMF and water. The solids were dried over a steam of air for 3 days to afford the title compound.

Step 3: {4-[2-(2,6-Dichloro-4-methylphenoxy)ethoxy]phenyl}boronic Acid

To a solution of 2-[2-(4-bromophenoxy)ethoxy]-1,3-dichloro-5-methylbenzene (1 eq.) from the previous step in THF (0.2 M) at −78° C. was added nBuLi (1.1 eq.) dropwise (internal temperature kept below −70° C.). After stirring for 30 min, triisopropyl borate (2 eq.) was added dropwise (internal temperature kept below −70° C.) and the reaction was slowly warmed to rt over 1 h. The solvent was concentrated in vacuo, and 1 N NaOH was added carefully. After stirring for 15 min, the aqueous solution was extracted with EtOAc. The combined organic extracts were washed with brine, dried over MgSO$_4$, and concentrated in vacuo. The product was stirred in hot DCM/Hex (1:1 v/v) and filtered to give the title compound boronic acid 1 as a white solid.

Piperidine Acid VII

| Compound | Structure |
| --- | --- |
| Piperidine acid 1 | (structure) |
| Piperidine acid 2 | (structure) |

Piperidine Acid 1

Step 1: 1-tert-Butyl 3-ethyl-4-{4-[2-(2,6-dichloro-4-methylphenoxy)ethoxy]phenyl}-5,6-dihydropyridine-1,3(2H)-dicarboxylate Triflate 1 (1 eq.) and boronic acid 1 (1 eq.) were dissolved in 2 N aqueous Na$_2$CO$_3$/n-propanol (1:4 v/v, 0.2 M). The reaction vessel was degassed and flushed with nitrogen gas. Pd(dppf)Cl$_2$ dichloromethane adduct (5 mol %) was added and the reaction was heated to 80° C. for 5 h. The reaction was cooled to rt and diluted with EtOAc. The resulting precipitate was filtered thru a pad of silica, washing with additional EtOAc. The filtrate was concentrated in vacuo. The crude product was purified by flash column chromatography (SiO$_2$, 12.5% EtOAc/Hex) to give the title compound as a yellow oil.

Step 2: 1-tert-Butyl 3-ethyl 4-{4-[2-(2,6-dichloro-4-methylphenoxy)ethoxy]phenyl}-piperidine-1,3-dicarboxylate To a solution of 1-tert-butyl-3-ethyl-4-{4-[2-(2,6-dichloro-4-methylphenoxy)-ethoxy]phenyl}-5,6-dihydropyridine-1,3(2H)-dicarboxylate (1 eq.) from the previous step in methanol (0.2 M) at rt under nitrogen atmosphere was added magnesium turnings (2 eq.). The reaction was stirred vigorously until a gentle reflux of solvent was achieved. After stirring for 1 hr, more magnesium turnings (1 eq.) were added. After another 1.5 h, more magnesium turnings (0.5 eq.) were added. After another 2 h, reaction was quenched with saturated aqueous NH$_4$Cl solution. The aqueous phase was extracted with ether. The combined organic extracts were washed with brine, dried over anhydrous MgSO$_4$, and concentrated in vacuo to afford a yellow oil that contained 1:1 mixture of cis-and trans-isomers. The mixture of cis-and trans-isomers was dissolved in absolute ethanol under nitrogen atmosphere. A solution of sodium ethoxide in ethanol (prepared by dissolving 1.2 eq. of sodium in absolute ethanol) was added, and the reaction was refluxed for 4 h. After cooling to rt, the reaction was diluted with ether and quenched with saturated aqueous NH$_4$Cl solution. The aqueous phase was extracted with ether. The combined organic extracts were washed with water, brine, dried over MgSO$_4$, and concentrated in vacuo. The crude product was purified by flash column chromatography (SiO$_2$, 12.5% EtOAc/Hex) to afford the title compound as a yellow oil that consisted of only the trans-diastereomer.

Step 3: 1-tert-Butyl 3-ethyl (3R,4S)-4-{4-[2-(2,6-dichloro-4-methylphenoxy)ethoxy]-phenyl}piperidine-1,3-dicarboxylate Racemic trans-1-tert-butyl 3-ethyl 4-{4-[2-(2,6-dichloro-4-methylphenoxy)-ethoxy]phenyl}-piperidine-1,3-dicarboxylate was resolved by a Chiral Pak AD preparative column (15% EtOH in Hex) to afford two enantiomers. 1-tert-Butyl 3-ethyl (3R,4S)-4-{4-[2-(2,6-dichloro-4-methylphenoxy)ethoxy]-phenyl}piperidine-1,3-dicarboxylate was eluted as the slower enantiomer (retention time=26.5 min)

Step 4: (3R,4S)-1-(tert-Butoxycarbonyl)-4-{4-[2-(2,6-dichloro-4-methylphenoxy)-ethoxy]phenyl}piperidine-3-carboxylic Acid To a solution of 1-tert-butyl-3-ethyl-(3R,4S)-4-{4-[2-(2,6-dichloro-4-methyl-phenoxy)ethoxy]-phenyl}piperidine-1,3-dicarboxylate (1 eq.) in ethanol (0.1 M) was added 10 N aqueous NaOH (3 eq.) and refluxed for 18 h. After cooling to rt, the reaction mixture was diluted with EtOAc and quenched with 1 N HCl (until pH<1). The aqueous phase was extracted with EtOAc. The combined organic extracts were washed with brine, dried over anhydrous $MgSO_4$, and concentrated in vacuo to afford the title compound piperidine acid 1 as a white foam.

Piperidine Acid 2

Step 1: 4-{4-[2-(tert-Butyldimethylsilanyloxy)ethoxy]phenyl}-5,6-dihydro-2H-pyridine-1,3-dicarboxylic Acid 1-tert-butyl Ester 3-methyl Ester To a sol. of 4-[2-(tert-butyldimethylsilanyloxy)ethoxy]bromobenzene (WO 03/093267, 7.95 g, 24 mmol) in THF (200 mL) at −78° C. was added BuLi (1.6M in hexane, 17.12 mL, 27.4 mmol). The sol. was stirred at −78° C. for 30 min, then $ZnCl_2$ (1M in THF, 30 mL, 30 mmol) was added. The resulting sol. was allowed to warm to rt, and 4-trifluoromethanesulfonyloxy-5,6-dihydro-2H-pyridine-1,3-dicarboxylic acid 1-tert-butyl ester 3-methyl ester (WO 2004/002957, 7.79 g, 20 mmol) in THF (20 mL) and $Pd(PPh_3)_4$ (0.69 g, 0.60 mmol) were added. The reaction mixture was heated to 50° C. for 1 h, and stirred 16 h at rt. The mixture was cooled to 0° C., and aq. sat. $NH_4Cl$ was added. EtOAc was added, and the org. phase was washed with brine, dried over $MgSO_4$, filtered, and the solvents were removed under reduced pressure. Purification of the residue by FC (EtOAc/heptane 2:8→1:0) yielded the title compound (8.1 g, 82%). LC-MS: $t_R$=1.23 min, ES+: 506.47.

Step 2: 4-{4-[2-(tert-Butyldimethylsilanyloxy)ethoxy]phenyl}piperidine-1,3-dicarboxylic Acid 1-tert-butyl Ester 3-methyl Ester Mg (1.40 g, 58 mmol) was added to a sol. of compound 4-{4-[2-(tert-Butyldimethylsilanyloxy)ethoxy]phenyl}-5,6-dihydro-2H-pyridine-1,3-dicarboxylic acid 1-tert-butyl ester 3-methyl ester (8.10 g, 17 mmol) in MeOH (40 mL) under Ar. The mixture was stirred for 1 h while maintaining the temperature below 30° C. Aq. 1M HCl (115 mL, 115 mmol) was added dropwise and the mixture was stirred for 1 h. The mixture was extracted with EtOAc (2×). The combined org. layers were washed with water, brine, dried over $MgSO_4$, filtered, and the solvents were removed under reduced pressure. Purification of the residue by FC (EtOAc/heptane 2:1) yielded a 2:3 trans/cis mixture of the title compound (7.6 g, 93%). LC-MS: $t_R$=1.23 min, ES+=508.47.

Step 3: 4-[4-(2-Hydroxyethoxy)phenyl]piperidine-1,3-dicarboxylic Acid 1-tert-butyl Ester 3-methyl Ester To a sol. of compound 4-{4-[2-(tert-Butyldimethylsilanyloxy)ethoxy]phenyl}piperidine-1,3-dicarboxylic acid 1-tert-butyl ester 3-methyl ester (7.60 g, 15.4 mmol) in THF (150 mL) at 0° C. and under Ar was added TBAF (4.86 g, 15.4 mmol). After stirring the mixture for 1 h, aq. sat. $NH_4Cl$ (100 mL) was added, and the reaction mixture was extracted with EtOAc (2×). The org. layer was washed with water, brine, dried over $MgSO_4$, filtered, and the solvents were removed under reduced pressure. Purification of the residue by FC (EtOAc/heptane 2:1→1:0) yielded the title compound (5.06 g, 87%). LC-MS: $t_R$=0.91 min, ES+=380.30.

Step 4: 4-{4-[2-(2,6-Dichloro-4-methylphenoxy)ethoxy-1-phenyl}piperidine-1,3-dicarboxylic Acid 1-tert-butyl Ester 3-methyl Ester A mixture of compound 4-[4-(2-Hydroxyethoxy)phenyl]piperidine-1,3-dicarboxylic acid 1-tert-butyl ester 3-methyl ester (5.50 g, 15 mmol), 2,6-dichloro-p-cresol (3.08 g, 18 mmol), azodicarboxylic dipiperidine (7.31 g, 29 mmol) and $PBu_3$ (14 mL, 58 mmol) in toluene (150 mL) was heated to 50° C. for 16 h. The mixture was allowed to cool to rt, filtered, and the precipitate was washed with toluene. The filtrate was diluted with EtOAc, and washed with water (2×) and brine. The org. layer was dried over $MgSO_4$, filtered, and the solvents were removed under reduced pressure. Purification of the crude by FC (EtOAc/heptane 0:1→1:9→2:8) yielded the compound as a colorless oil (7.3 g, 90%). LC-MS: $t_R$=1.18 min, ES+=538.34.

Step 5: (rac.)-(3R*,4S*)-4-{4-[2-(2,6-Dichloro-4-methylphenoxy)ethoxy]phenyl}-piperidine-1,3-dicarboxylic Acid 1-tert-butyl Ester 3-methyl Ester To a sol. of compound 4-{4-[2-(2,6-Dichloro-4-methylphenoxy)ethoxy]phenyl}piperidine-1,3-dicarboxylic acid 1-tert-butyl ester 3-methyl ester (0.21 g, 0.38 mmol) in MeOH (2 mL) under Ar was added NaOMe (6 mg, 0.11 mmol). The mixture was stirred for 3 days at 70° C. Water was added, and the mixture was extracted with EtOAc. The org. phase was washed with brine, dried over $MgSO_4$, filtered, and the solvents were removed under reduced pressure. The title compound (150 mg, 72%) was not further purified. LC-MS: $t_R$=1.18 min, ES+=538.32.

Step 6: (rac.)-(3R*,4S*)-4-{4-[2-(2,6-Dichloro-4-methyl-phenoxy)-ethoxy]-phenyl}-piperidine-1,3-dicarboxylic Acid 1-tert-butyl Ester To a sol. of compound (rac.)-(3R*,4S*)-4-{4-[2-(2,6-Dichloro-4-methylphenoxy)ethoxy]phenyl}-piperidine-1,3-dicarboxylic acid 1-tert-butyl ester 3-methyl ester (0.15 g, 0.27 mmol) in MeOH (1 mL) was added aq. 1M NaOH (1 mL). The mixture was stirred at 70° C. for 2 h. Water was added, and the mixture was extracted with EtOAc. The org. phase was washed with brine, dried over $MgSO_4$, filtered, and the solvents were removed under reduced pressure. The crude residue was purified on a pad of silica gel to yield the title compound (93 mg, 65%). LC-MS: $t_R$=1.12 min, ES+=524.24.

Step 7: (3R,4S)-4-{4-[2-(2,6-Dichloro-4-methyl-phenoxy)-ethoxy]-phenyl}-piperidine-1,3-dicarboxylic Acid 1-tert-butyl Ester Compound (rac.)-(3R*,4S*)-4-{4-[2-(2,6-Dichloro-4-methyl-phenoxy)-ethoxy]-phenyl}-piperidine-1,3-dicarboxylic acid 1-tert-butyl ester (4.46 g, 8.5 mmol) was separated using a preparative HPLC equipped with a chiral column as described herein above. An isocratic eluent was applied, consisting of 97% hexane, 3% ethanol, and 0.1% TFA. The piperidine acid 2 compound was obtained (1.35 g, 30%). Analytical chiral HPLC (same eluent as preparative): $t_R$=29.00 min. Resolution by a Chiral Pak AD preparative column (20% EtOH in Hex plus 0.25% formic acid) to afford two enantiomers. (3R,4S)-1-(tert-Butoxycarbonyl)-4-{6-[2-(2,6-dichloro-4-methylphen-oxy)ethoxy]pyridin-3- yl}piperidine-3-carboxylic acid was eluted as the slower enantiomer (retention time=8.54 min).

Amine VIII

| Compound | Structure |
| --- | --- |
| Amine 1 | (cyclopropyl-HN-CH2-phenyl with OTBS and propyl-OMe substituents) |

Amine 1

Step 1: 3-Bromo-5-hydroxybenzaldehyde

To a toluene solution (1.6 M) of n-butyl lithium (2.5 M hexane solution, 2.1 eq.) was added at −10° C. n-butyl magnesium chloride (2.0 M THF solution, 0.6 eq.). The reaction mixture was stirred at −10° C. for 30 min before a toluene solution (0.7 M) of 3,5-dibromophenol (1 eq.) was added dropwise at −10° C. over a period of 35 min. After stirring at −10° C. for a further 30 min, the reaction mixture was cooled to −40° C. before DMF (20 eq.) was added dropwise over 20 min. The reaction mixture was then slowly warmed to rt and allowed to stir at rt for 1 h. The reaction was carefully quenched at 0° C. with 10% aqueous HCl and extracted with ether. The combined organic extracts were washed with water and brine and dried over $MgSO_4$. Concentration of the filtrate in vacuo afforded a yellow solid. Recrystallization of the crude product in ether/hexane afforded the title compound as a beige powder.

Step 2: 3-Hydroxy-5-[(1E)-3-methoxyprop-1-en-1-yl]benzaldehyde

3-Bromo-5-hydroxybenzaldehyde (1 eq.) from the previous step and 2-[(1E)-3-methoxyprop-1-en-1-yl]-4,4,5,5-tetramethyl-1,3,2-dioxaborolane (1 eq.) were combined in DMF (0.05 M). To this solution was then added palladium acetate (10 mol %), triphenylphosphine (20 mol %), and sodium carbonate (2 M aqueous solution, 4 eq.). The resulting suspension was heated at 80° C. and stirred for 16 h. The reaction mixture was quenched with 10% aqueous HCl and extracted with ether. The combined organic extracts were washed with water, saturated aqueous $NaHCO_3$ solution, brine, dried over $MgSO_4$, and concentrated in vacuo. The crude product was purified by flash column chromatography ($SiO_2$, 20%→33% EtOAc/Hex) to afford the title compound as a yellow oil.

Step 3: 3-{[tert-Butyl(dimethyl)silyl]oxy}-5-[(1E)-3-methoxyprop-1-en-yl]-benzaldehyde 3-Hydroxy-5-[(1E)-3-methoxyprop-1-en-1-yl]benzaldehyde (1 eq.) from the previous step and tert-butylchlorodimethylsilane (1 eq.) were combined in DMF (0.5 M). To this solution was then added imidazole (1.5 eq.), and the reaction mixture was stirred at rt for 16 h. The resulting solution was quenched with water and extracted with ether/hexanes (1:1 v/v). The combined organic extracts were washed with brine, dried over $MgSO_4$, and filtered through a plug of $SiO_2$. Concentration of the filtrate in vacuo afforded the title compound as a pale yellow oil.

Step 4: N-{[3-{[tert-Butyl(dimethyl)silyl]oxy}-5-[(1E)-3-methoxyprop-1-en-1-yl]-benzyl}cyclopropanamine To a solution of 3-{[tert-butyl(dimethyl)silyl]oxy}-5-[(1E)-3-methoxyprop-1-en-1-yl]benzaldehyde (1 eq.) from the previous step in DCM was added cyclopropanamine (2 eq.) and magnesium sulfate (1.5 eq.). The resulting suspension was stirred at rt for 12 h. The insolubles were removed via filtration. Concentration of the filtrate in vacuo afforded the crude imine as a yellow oil. This was then taken up in methanol (0.3 M), and sodium borohydride (1.5 eq.) was added portionwise at 0° C. over 5 min. The reaction mixture was slowly warmed to rt over 1 h and then stirred at rt for 2 h. The reaction was slowly quenched with saturated aqueous $NaHCO_3$ solution, and the resulting mixture was extracted with ether. The combined organic extracts were washed with water, brine, dried over $MgSO_4$, and concentrated in vacuo to afford the title compound as a golden, yellow oil.

Step 5: N-[3-{[tert-Butyl(dimethyl)silyl]oxy}-5-(3-methoxypropyl)benzyl]cyclo-propanamine To a solution of N-{3-{[tert-butyl(dimethyl)silyl]oxy}-5-[(1E)-3-methoxyprop-1-en-1-yl]benzyl}cyclopropanamine from the previous step (1 eq.) in EtOAc (0.04 M) was added 10% palladium on activated carbon (10 mol %). The vessel was evacuated and back filled with hydrogen. The reaction suspension was then stirred under a balloon atmosphere of hydrogen for 1.5 h. The reaction was diluted with DCM and filtered through a bed of celite. The insolubles were further washed with EtOAc and methanol. Concentration of the filtrate in vacuo afforded the title compound amine 1 as a colorless oil.

$R^4$ Appendage XI

All of the $R^4$-Z (Z=OH or leaving group) XI are available through commercial sources unless described below.

| Z—$R^4$ | Structure |
| --- | --- |
| Appendage 1 | (HO-cyclopropyl-C(O)O-ethyl) |
| Appendage 2 | (HO-cyclopropyl-C(O)O-ethyl, diastereomer) |
| Appendage 3 | (Ms-O-CH2-cyclopropyl-CH2-C(O)-O-methyl) |

-continued

| Z—R⁴ | Structure |
|---|---|
| Appendage 4 | [structure: methanesulfonate ester of (1-(cyanomethyl)cyclopropyl)methanol] |
| Appendage 5 | [structure: methyl 2,2-dimethyl-4-[(methylsulfonyl)oxy]butanoate] |

Appendage 1

Step 1: Ethyl (1R,2R)-2-(hydroxymethyl)cyclopropanecarboxylate

To a solution of ethyl 2-formyl-1-cyclopropanecarboxylate (1.5 eq.) in methanol (0.7 M) at 0° C. was added sodium borohydride (1.5 eq.) in portions over 30 min. The mixture was allowed to stir at rt for 1.5 h and then cooled in an ice bath. Saturated aqueous NH₄Cl solution was added dropwise, and the mixture was stirred for 1.5 h. Water was added, and the aqueous layer was extracted with. The combined organic extracts were washed with brine, dried over MgSO₄, and concentrated to afford a racemic mixture of the title compound as a clear oil. Racemic trans 2-(hydroxymethyl)cyclopropanecarboxylate was purified by a Chiral Pak AD preparative column (10% EtOH/Hex) to afford two enantiomers. Ethyl (1R,2R)-2-(hydroxymethyl)cyclopropanecarboxylate was eluted as the faster enantiomer (retention time=12.94 min)

Appendage 2

Step 1: Ethyl (1S,2S)-2-(hydroxymethyl)cyclopropanecarboxylate

Racemic trans 2-(hydroxymethyl)cyclopropanecarboxylate was purified by a Chiral Pak AD preparative column (10% EtOH/Hex) to afford two enantiomers. Ethyl (1S,2S)-2-(hydroxymethyl)cyclopropanecarboxylate was eluted as the slower enantiomer (retention time=16.44 min).

Appendage 3

Step 1: Methyl [1-(hydroxymethyl)cyclopropyl]acetate

To a solution of [1-(hydroxymethyl)cyclopropyl]acetonitrile (1 eq.) (prepared according to the procedure described in WO2005/105749 Example 2/Step 4) in ethanol (0.1 M) was added 8 N aqueous KOH solution (18 eq.). The reaction was heated to 100° C. and stirred for 18 h. After cooling to rt temperature, ethanol was removed in vacuo. The resulting aqueous solution was diluted with EtOAc and cooled in ice water bath. Concentrated HCl was added slowly with stirring over 15 min, keeping the temperature of the reaction below 10° C. After the reaction has reached pH<1, the aqueous layer was extracted by EtOAc. The combined organic extracts were dried over MgSO₄ and filtered. The EtOAc solution was cooled down to 0° C., and a solution of diazomethane in ether was added until a faint yellow color persisted. The reaction was allowed to stir for an additional 10 min before concentrated in vacuo. The crude product was purified on flash column chromatography (SiO₂, 40% EtOAc in Hex) to afford the title compound as a liquid.

Step 2: Methyl(1-{[(methylsulfonyl)oxy]methyl}cyclopropyl)acetate

To a solution of methyl [1-(hydroxymethyl)cyclopropyl]acetate (1 eq.) from the previous step in DCM (0.1 M) at −40° C. was added triethylamine (3 eq.) and then methanesulfonyl chloride (1.5 eq.). The reaction was warmed to 0° C. over 1 h, and it was diluted with DCM and quenched with saturated aqueous NaHCO₃. The aqueous phase was extracted with DCM. The combined organic extracts were dried over MgSO₄ and concentrated in vacuo. The crude product was purified by flash column chromatography (SiO₂, 0%→50% EtOAc in Hex) to afford the title compound appendage 3 as an oil.

Appendage 4

Step 1: [1-(Cyanomethyl)cyclopropyl]methyl methanesulfonate

To a solution of [1-(hydroxymethyl)cyclopropyl]acetonitrile (prepared according to the procedure described in WO2005/105749 Example 2/Step 4) (1 eq.) in DCM at −40° C. was added triethylamine (3 eq.) and then methanesulfonyl chloride (1.5 eq.). The reaction was warmed to −10° C. over 1 h, and it was diluted with DCM and quenched with saturated aqueous NaHCO₃. The aqueous phase was extracted with DCM. The combined organic extracts were dried over MgSO₄ and concentrated in vacuo. The crude product was purified by flash column chromatography (SiO₂, 0%→50% EtOAc in Hex) to afford the title compound appendage 4 as an oil.

Appendage 5

Step 1: Methyl 4-hydroxy-2,2-dimethylbutanoate

To a solution of 3,3-dimethyldihydrofuran-2(3H)-one (1 eq.) in ethanol (1 M) was added 8 N KOH (17 eq.). The mixture was stirred overnight, and the ethanolic solvent was concentrated in vacuo. To the remaining aqueous solution was added ethyl acetate and cooled to −15° C. Concentrated HCl was added dropwise until pH<1, taking care the internal temperature does not exceed 10° C. The aqueous layer was extracted with ethyl acetate three times. The combined organic extracts were dried over anhydrous Na₂SO₄, filtered, and cooled in an ice water bath. A solution of diazomethane in ether was added until a yellow color persisted. The reaction was stirred for an additional 10 min at rt and then concentrated in vacuo. The crude product was purified by flash column chromatography (SiO₂, 10 to 60% EtOAc in Hex) to afford the title compound as an oil.

Step 2: Methyl 2,2-dimethyl-4-[(methylsulfonyl)oxy]butanoate

To a solution of methyl 4-hydroxy-2,2-dimethylbutanoate (1 eq.) from the previous step in DCM (0.1 M) at −40° C. was added methanesulfonyl chloride (1.5 eq.) and triethylamine (3.0 eq.). The reaction was warmed to −20° C. over 30 min and then quenched with saturated aqueous NaHCO₃ solution. The aqueous phase was extracted with DCM. The combined organic extracts were dried over MgSO₄ and concentrated in vacuo. The crude product was used in the next step without further purification.

Compounds of the present invention were prepared according to the following methods.

EXAMPLE 1

Ethyl (1R,2R)-2-{[3-({cyclopropyl[((3R,4S)-4-{4-[2-(2,6-dichloro-4-methylphenoxy)-ethoxy]phenyl}piperidin-3-yl)carbonyl]amino}methyl)-5-(3-methoxypropyl)phen-oxy]methyl}cyclopropanecarboxylate

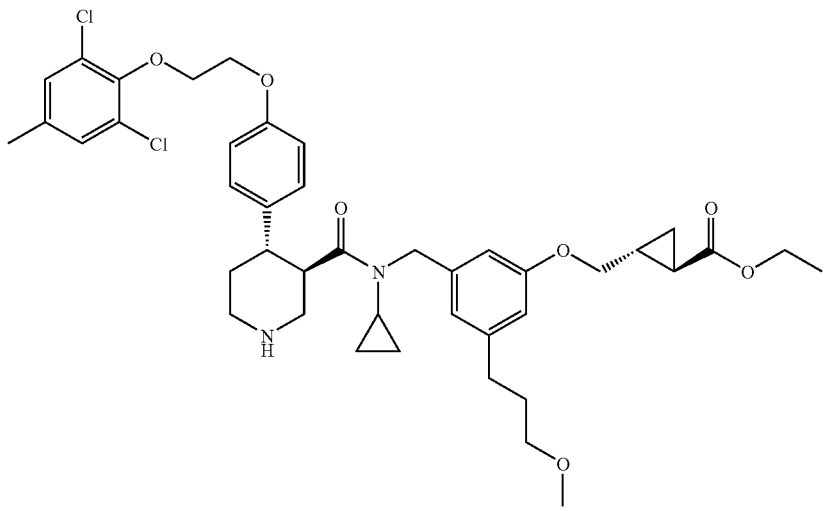 [SMILES: CCOC(=O)[C@@H]1C[C@H]1COc1cc(CCCOC)cc(CN(C(=O)[C@H]2CNCC[C@@H]2c2ccc(OCCOc3c(Cl)cc(C)cc3Cl)cc2)C2CC2)c1]

Step 1: tert-Butyl (3R,4S)-3-{[[3-{[tert-butyl(dimethyl)silyl]oxy}-5-(3-methoxy-propyl)benzyl](cyclopropyl)amino]carbonyl}-4-{4-[2-(2,6-dichloro-4-methyl-phenox)ethoxy]phenyl}piperidine-1-carboxylate To a solution of (3R,4S)-1-(tert-butoxycarbonyl)-4-{4-[2-(2,6-dichloro-4-methylphenoxy)ethoxy]phenyl}piperidine-3-carboxylic acid (piperidine acid 1) (1 eq) and N-[3-{[tert-Butyl(dimethyl)silyl]oxy}-5-(3-methoxypropyl)benzyl]cyclo-propanamine (amine 1) (1.8 eq.) in DCM (0.15 M) was added o-benzotriazol-1-yl-N,N,N',N'-tetramethyluronium hexafluorophosphate (aka. HATU, 1.5 eq.) and Hunig's base (3 eq.). After stirring for 18 hr at rt, the reaction was diluted with ether. The organic extract was washed three times with 1 N aqueous HCl, water, brine, dried over MgSO₄, and concentrated in vacuo. The crude product was purified by flash column chromatography (SiO₂, 20% EtOAc in Hex) to afford the title compound as an oil.

Step 2: tert-Butyl (3R,4S)-3-({cyclopropyl[3-hydroxy-5-(3-methoxypropyl)benzyl]-amino}carbonyl)-4-{4-[2-(2,6-dichloro-4-methylphenoxy)ethoxy]phenyl}piperidine-1-carboxylate To a solution of tert-butyl (3R,4S)-3-{[[3-{[tert-butyl(dimethyl)silyl]oxy}-5-(3-methoxypropyl)benzyl](cyclopropyl)amino]carbonyl}-4-{4-[2-(2,6-dichloro-4-methylphenox)ethoxy]phenyl}piperidine-1-carboxylate (1 eq.) from the previous step in THF (0.1 M) was added a solution of 1 M tetrabutylammonium fluoride in THF (1.3 eq.). The reaction was stirred at rt for 1 h and then concentrated in vacuo. The residue was purified by flash column chromatography (SiO₂, 50% EtOAc in Hex) to afford the title compound as a foam.

Step 3: tert-Butyl (3R,4S)-3-({cyclopropyl[3-{[(1R,2R)-2-(ethoxycarbonyl)cyclo-propyl]methoxy}-5-(3-methoxypropyl)benzyl]amino}carbonyl)-4-{4-[2-(2,6-di-chloro-4-methylphenoxy)ethoxy]phenyl}piperidine-1-carboxylate To a solution of tert-butyl(3R,4S)-3-({cyclopropyl[3-hydroxy-5-(3-methoxy-propyl)benzyl]amino}carbonyl)-4-{4-[2-(2,6-dichloro-4-methylphenoxy)ethoxy]-phenyl}piperidine-1-carboxylate (1 eq.) from the previous step in toluene (0.1 M) was added 1,1'-(azodicarbonyl)dipiperidine (1.2 eq.), ethyl (1R,2R)-2-(hydroxyl-methyl)cyclopropanecarboxylate (appendage 1) (2 eq.), and tri-n-butylphosphine (1.2 eq.). The reaction was heated to 80° C. and stirred for 18 h. While hot, the reaction was diluted with EtOAc/water. The aqueous layer was extracted with EtOAc. The combined organic extracts were washed with brine, dried over MgSO₄, and concentrated in vacuo. The crude product was purified by flash column chromatography (SiO₂, 40% EtOAc in Hex) to afford the title compound as an oil.

Step 4: Ethyl (1R,2R)-2-{[3-({cyclopropyl[((3R,4S)-4-{4-[2-(2,6-dichloro-4-methyl-phenoxy)ethoxy]phenyl}piperidin-3-yl)carbonyl]amino}methyl)-5-(3-methoxy-propyl)phenoxy]methyl}cyclopropanecarboxylate To a solution tert-butyl (3R,4S)-3-({cyclopropyl[3-{[(1R,2R)-2-(ethoxy-carbonyl)cyclopropyl]methoxy}-5-(3-methoxypropyl)benzyl]amino}carbonyl)-4-{4-[2-(2,6-dichloro-4-methylphenoxy)ethoxy]phenyl}piperidine-1-carboxylate (1 eq.) from the previous step in DCM (0.05 M) was added 4 M HCl in dioxane (10 eq.) and stirred at rt for 5 h. The reaction was concentrated in vacuo. The crude product was purified by flash column chromatography (SiO₂, 5% [2 M NH₃ in MeOH] in DCM) to afford the title compound as a colorless oil.

¹H NMR (acetone d-6): δ 7.28 (s, 2H), 7.20 (d, 2H), 6.83 (d, 2H), 6.60 (s, 1H), 6.47 (s, 1H), 6.40 (s, 1H), 4.30-4.42 (m, 5H), 4.27 (d, 1H), 4.05-4.15 (m, 2H), 4.0 (dd, 1H), 3.8 (dd, 1H), 3.55 (dt, 1H), 3.31 (t, 2H), 3.28 (s, 3H), 3.00-3.22 (m, 3H), 2.67-2.85 (m, 2H), 2.55 (t, 2H), 2.30-2.35 (m, 4H), 1.70-1.85 (m, 6H), 1.22 (t, 3H), 0.4-1.2 (m, 6H).

LRMS [M+H]=767.3

EXAMPLE 2

(1R,2R)-2-{[3-({Cyclopropyl[((3R,4S)-4-{4-[2-(2,6-dichloro-4-methylphenoxy)-ethoxy]phenyl}piperidin-3-yl)carbonyl]amino}methyl)-5-(3-methoxypropyl)phen-oxy]methyl}cyclopropanecarboxylic Acid

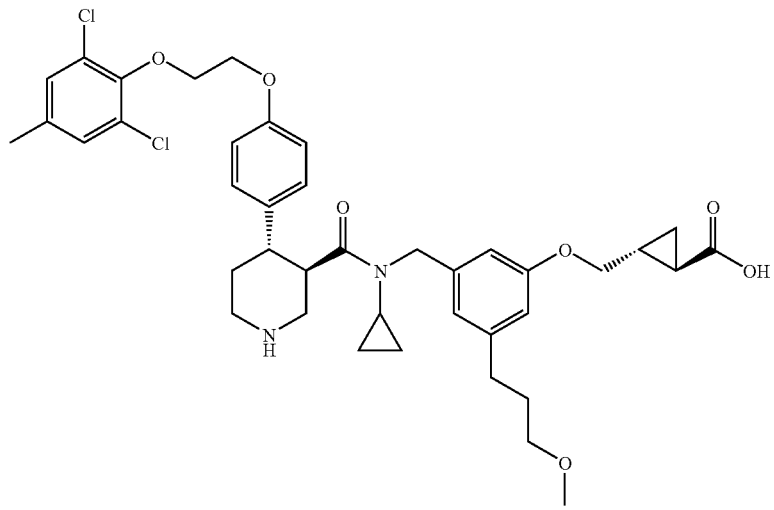 [SMILES: COCCCc1cc(CN(C(=O)[C@H]2CNCC[C@@H]2c2ccc(OCCOc3c(Cl)cc(C)cc3Cl)cc2)C2CC2)cc(OC[C@@H]2C[C@H]2C(=O)O)c1]

Step 1: (1R,2R)-2-{[3-({Cyclopropyl[((3R,4S)-4-{4-[2-(2,6-dichloro-4-methyl-phenoxy)ethoxy]phenyl}piperidin-3-yl)carbonyl]amino}methyl)-5-(3-methoxy-propyl)phenoxy]methyl}cyclopropanecarboxylic Acid To a solution of ethyl (1R,2R)-2-{[3-({cyclopropyl[((3R,4S)-4-{4-[2-(2,6-dichloro-4-methylphenoxy)ethoxy]phenyl}piperidin-3-yl)carbonyl]amino}methyl)-5-(3-methoxypropyl)phenoxy]methyl}cyclopropanecarboxylate (1 eq.) from Example 1 in ethanol was added 1 N aqueous NaOH (1.3 eq.). The reaction was heated to 75° C. for 18 h. After cooling to rt, the reaction was concentrated in vacuo to afford the sodium salt of the title compound as a foam.

$^1$H NMR (DMSO): δ 7.33 (s, 2H), 7.12 (d, 2H), 6.80 (d, 2H), 6.52 (s, 1H), 6.40 (s, 1H), 6.15 (s, 1H), 4.20-4.35 (m, 6H), 3.60-3.80 (m, 2H), 2.25-3.5 (m, 17H), 1.60-1.73 (m, 4H), 1.10-1.42 (m, 2H), 0.3-0.8 (m, 6H).

LRMS [M+H]=739.2 (for free acid)

EXAMPLE 3

Methyl (1R,2R)-2-{[3-({cyclopropyl[((3R,4S)-4-{4-[2-(2,6-dichloro-4-methyl-phenoxy)ethoxy]phenyl}piperidin-3-yl)carbonyl]amino}methyl)-5-(3-methoxy-propyl)phenoxy]methyl}cyclopropanecarboxylate

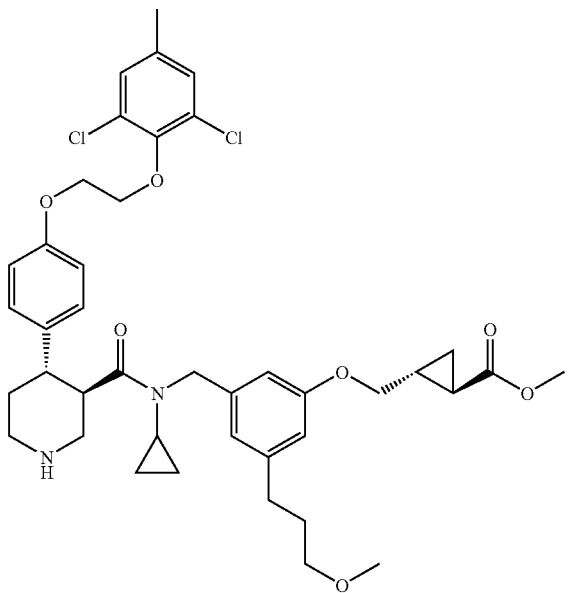 [SMILES: COCCCc1cc(CN(C(=O)[C@H]2CNCC[C@@H]2c2ccc(OCCOc3c(Cl)cc(C)cc3Cl)cc2)C2CC2)cc(OC[C@@H]2C[C@H]2C(=O)OC)c1]

To a solution of (1R,2R)-2-{[3-({cyclopropyl[((3R,4S)-4-{4-[2-(2,6-dichloro-4-methylphenoxy)ethoxy]phenyl}piperidin-3-yl)carbonyl]amino}methyl)-5-(3-methoxypropyl)phenoxy]methyl}cyclopropanecarboxylic acid (1 eq., neutral form) from Example 2 was added a solution of diazomethane in ether until a faint yellow color persisted. The solvent was evaporated by a stream of nitrogen gas. The residue was purified by flash column chromatography (SiO$_2$, 10% MeOH in DCM plus 1% aqueous NH$_4$OH) afford the title compound as a colorless oil.

$^1$H NMR (acetone d-6): 7.28 (s, 2H), 7.20 (d, 2H), 6.84 (d, 2H), 6.60 (s, 1H), 6.46 (s, 1H), 6.40 (s, 1H), 4.25-4.45 (m, 6H), 4.00 (dd, 1H), 3.80 (dd, 1H), 3.65 (s, 3H), 3.55 (dt, 1H), 3.33 (t, 2H), 3.28 (s, 3H), 3.00-3.25 (m, 3H), 2.69-2.85 (m, 2H), 2.55 (t, 2H), 2.30-2.40 (m, 4H), 1.70-1.90 (m, 6H), 1.00-1.21 (m, 2H), 0.45-0.90 (m, 4H).

LRMS [M+H]=753.2

EXAMPLE 4

2-(Dimethylamino)-2-oxoethyl(1R,2R)-2-{[3-({cyclopropyl[((3R,4S)-4-{4-[2-(2,6-dichloro-4-methylphenoxy)ethoxy]phenyl}piperidin-3-yl)carbonyl]amino}methyl)-5-(3-methoxypropyl)phenoxy]methyl}cyclopropanecarboxylate

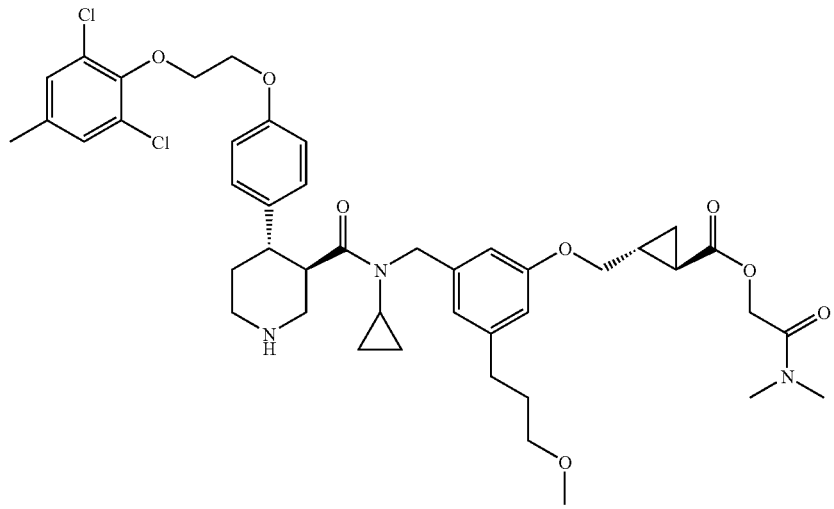

Step 1: (1R,2R)-2-{[3-{[[((3R,4S)-1-(tert-Butoxycarbonyl)-4-{4-[2-(2,6-dichloro-4-methylphenoxy)ethoxy]phenyl}piperidin-3-yl)carbonyl](cyclopropyl)amino]methyl}-5-(3-methoxypropyl)phenoxy]methyl}cyclopropanecarboxylic Acid To a solution of tert-butyl (3R,4S)-3-({cyclopropyl[3-{[(1R,2R)-2-(ethoxy-carbonyl)cyclopropyl]methoxy}-5-(3-methoxypropyl)benzyl]amino}carbonyl)-4-{4-[2-(2,6-dichloro-4-methylphenoxy)ethoxy]phenyl}piperidine-1-carboxylate (1 eq.) from Example 1/Step 3 in ethanol (0.1 M) was added 1 M aqueous NaOH (3 eq.). The reaction was heated at 100° C. in a microwave (Biotage) for 5 min. The reaction was cooled to rt and concentrated in vacuo. The residue was suspended in 1 N aqueous HCl and EtOAc. The aqueous layer was extracted several times with EtOAc. The combined organic extracts were washed with brine, dried over MgSO$_4$, and concentrated in vacuo to afford the title compound as a foam.

Step 2: tert-Butyl (3R,4S)-3-({cyclopropyl[3-[((1R,2R)-2-{[2-(dimethylamino)-2-oxo-ethoxy]carbonyl}cyclopropyl)methoxy]-5-(3-methoxypropyl)benzyl]amino}-carbonyl)-4-{4-[2-(2,6-dichloro-4-methylphenoxy)ethoxy]phenyl}piperidine-1-carboxylate To a solution of (1R,2R)-2-{[3-{[[((3R,4S)-1-(tert-butoxycarbonyl)-4-{4-[2-(2,6-dichloro-4-methylphenoxy)ethoxy]phenyl}piperidin-3-yl)carbonyl](cyclopropyl)amino]methyl}-5-(3-methoxypropyl)phenoxy]methyl}cyclopropanecarboxylic acid (1 eq.) from the previous step in DMF (0.1 M) was added cesium carbonate (2 eq.) and 2-chloro-N,N-dimethylacetamide (1.8 eq.). The reaction was heated to 80° C. for 2 h. After cooling to rt, the reaction was diluted with ether. The organic extract was washed with water, brine, dried over MgSO$_4$, and concentrated in vacuo. The crude product was purified was flash column chromatography (SiO$_2$, 90% EtOAc in Hex) to afford the title compound as an oil.

Step 3: 2-(Dimethylamino)-2-oxoethyl(1R,2R)-2-{[3-({cyclopropyl[((3R,4S)-4-{4-[2-(2,6-dichloro-4-methylphenoxy)ethoxy]phenyl}piperidin-3-yl)carbonyl]-amino}methyl)-5-(3-methoxypropyl)phenoxy]methyl}cyclopropanecarboxylate Prepared according to the procedure described in Example 1/Step 4 but using instead tert-butyl (3R,4S)-3-({cyclopropyl[3-[((1R,2R)-2-{[2-(dimethylamino)-2-oxo-ethoxy]carbonyl}cyclopropyl)methoxy]-5-(3-methoxypropyl)benzyl]amino}-carbonyl)-4-{4-[2-(2,6-dichloro-4-methylphenoxy)ethoxy]phenyl}piperidine-1-carboxylate from the previous step as the starting material. The title compound was a colorless oil.

$^1$H NMR (acetone d-6): δ 7.28 (s, 2H), 7.20 (d, 2H), 6.84 (d, 2H), 6.61 (s, 1H), 6.49 (s, 1H), 6.40 (s, 1H), 4.79 (q, 2H), 4.28-4.43 (m, 6H), 3.98 (dd, 1H), 3.85 (dd, 1H), 3.55 (dt, 1H), 2.69-3.38 (m, 16H), 2.53 (t, 2H), 2.30-2.38 (m, 4H), 1.70-1.95 (m, 6H), 0.45-1.3 (m, 6H).

LRMS [M+H]=824.5

EXAMPLE 5

2,3-Dihydro-1H-inden-5-yl(1R,2R)-2-{[3-({cyclopropyl[((3R,4S)-4-{4-[2-(2,6-di-chloro-4-methylphenoxy)ethoxy]phenyl}piperidin-3-yl)carbonyl]amino}methyl)-5-(3-methoxypropyl)phenoxy]methyl}cyclopropanecarboxylate

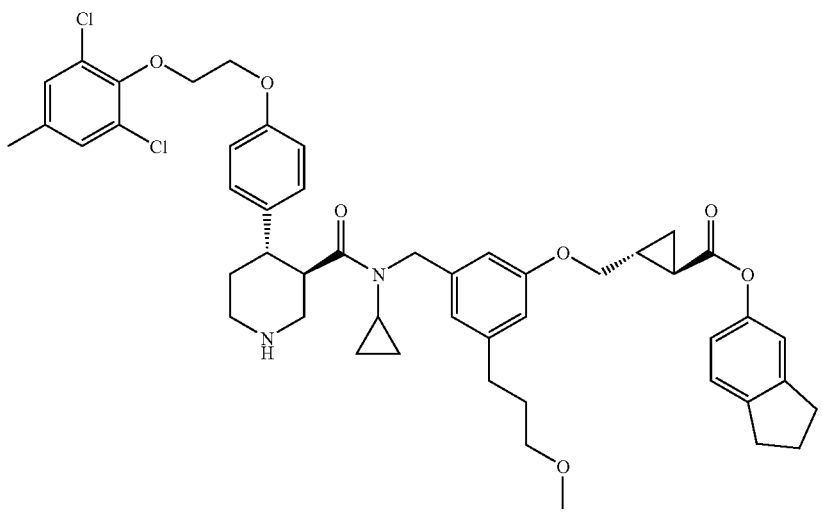 [SMILES: COCCCc1cc(CN(C(=O)[C@H]2CNCC[C@@H]2c2ccc(OCCOc3c(Cl)cc(C)cc3Cl)cc2)C2CC2)cc(OC[C@@H]2C[C@H]2C(=O)Oc2ccc3c(c2)CCC3)c1]

Step 1: Tert-Butyl (3R,4S)-3-({cyclopropyl[3-({(1R,2R)-2-[(2,3-dihydro-1H-inden-5-yloxy)-carbonyl]cyclopropyl}methoxy)-5-(3-methoxypropyl)benzyl]amino}-carbonyl)-4-{4-[2-(2,6-dichloro-4-methylphenoxy)ethoxy]phenyl}piperidine-1-carboxylate To a solution of (1R,2R)-2-{[3-{[[((3R,4S)-1-(tert-butoxycarbonyl)-4-{4-[2-(2,6-dichloro-4-methylphenoxy)ethoxy]phenyl}piperidin-3-yl)carbonyl](cyclopropyl)-amino]methyl}-5-(3-methoxypropyl)phenoxy]methyl}cyclopropanecarboxylic acid (1 eq.) from Example 4/Step 1 in DCM (0.1 M) at −20° C. was added N-methylmorpholine (1.3 eq.) and isobutylchloroformate (1.3 eq.). The reaction was stirred at −20° C. for 45 min. Meanwhile, a solution of indan-5-ol (2 eq) in THF (0.2) at 0° C. was added sodium hydride (60% dispersion in mineral oil, 1 eq.), stirred for 30 min at rt, and added to the reaction at −15° C. The reaction was stirred at rt for 18 h and then quenched with saturated aqueous NaHCO₃ solution. The aqueous layer was extracted with EtOAc. The combined organic extracts were washed with brine, dried over MgSO₄, and concentrated in vacuo. The crude product was purified by flash column chromatography (SiO₂, 35% EtOAc in Hex) to afford the title compound as an oil.

Step 2: 2,3-Dihydro-1H-inden-5-yl(1R,2R)-2-{[3-({cyclopropyl[((3R,4S)-4-{4-[2-(2,6-dichloro-4-methylphenoxy)ethoxy]phenyl}piperidin-3-yl)carbonyl]-amino}methyl)-5-(3-methoxypropyl)phenoxy]methyl}cyclopropanecarboxylate Prepared according to the procedure described in Example 1/Step 4 but using instead tert-butyl (3R,4S)-3-({cyclopropyl [3-({(1R,2R)-2-[(2,3-dihydro-1H-inden-5-yloxy)carbonyl] cyclopropyl}methoxy)-5-(3-methoxypropyl)benzyl]amino}-carbonyl)-4-{4-[2-(2,6-dichloro-4-methylphenoxy) ethoxy]phenyl}piperidine-1-carboxylate from the previous step as the starting material. The title compound was a colorless oil.

¹H NMR (acetone d-6): δ 7.28 (s, 2H), 7.19-7.22 (m, 3H), 6.96 (s, 1H), 6.80-6.87 (m, 3H), 6.62 (s, 1H), 6.50 (s, 1H), 6.40 (s, 1H), 4.23-4.45 (m, 6H), 4.05 (dd, 1H), 3.90 (dd, 1H), 3.55 (dt, 1H), 3.40-3.50 (m, 4H), 3.28 (s, 3H), 3.00-3.24 (m, 3H), 2.69-2.95 (m, 6H), 2.55 (t, 2H), 2.30-2.40 (m, 4H), 1.70-2.00 (m, 6H), 1.19-1.35 (m, 2H), 0.45-0.90 (m, 4H).

LRMS [M+H]=855.2

EXAMPLE 6

(5R)-5,6-Bis(nitrooxy)hexyl-(1R,2R)-2-{[3-({cyclopropyl[((3R,4S)-4-{4-[2-(2,6-dichloro-4-methylphenoxy)ethoxy]phenyl}piperidin-3-yl)carbonyl]amino}methyl)-5-(3-methoxypropyl)phenoxy]methyl}cyclopropanecarboxylate

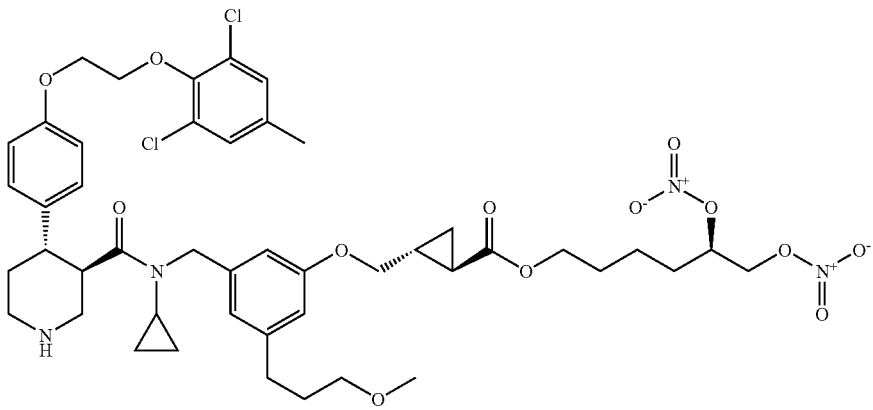 [SMILES: COCCCc1cc(CN(C(=O)[C@H]2CNCC[C@@H]2c2ccc(OCCOc3c(Cl)cc(C)cc3Cl)cc2)C2CC2)cc(OC[C@@H]2C[C@H]2C(=O)OCCCC[C@H](CO[N+](=O)[O-])O[N+](=O)[O-])c1]

Step 1: Tert-Butyl(3R,4S)-3-{[[3-{[(1R,2R)-2-({[(5R)-5,6-bis(nitrooxy)hexyl]oxy}-carbonyl)cyclopropyl]methoxy}-5-(3-methoxypropyl)benzyl](cyclopropyl)amino]-carbonyl}-4-{4-[2-(2,6-dichloro-4-methylphenoxy)ethoxy]phenyl}piperidine-1-carboxylate To a solution of (1R,2R)-2-{[3-{[[((3R,4S)-1-(tert-butoxycarbonyl)-4-{4-[2-(2,6-dichloro-4-methylphenoxy)ethoxy]phenyl}piperidin-3-yl)carbonyl](cyclopropyl)amino]methyl}-5-(3-methoxypropyl)phenoxy]methyl}cyclopropanecarboxylic acid (1 eq.) from Example 4/Step 1 in DCM (0.17 M) was added (2R)-6-hydroxyhexane-1,2-diyl dinitrate (1.5 eq., prepared according to the procedure described in WO2005070868/Example 2, incorporated by reference), 1-(3-dimethylaminopropyl)-3-ethylcarbodiimide hydrochloride (1.5 eq.), and 4-dimethylaminopyridine (1.5 eq.). The reaction was stirred at rt for 18 h and then concentrated in vacuo. The residue was purified by flash column chromatography (SiO$_2$, 40% EtOAc in Hex) to afford the title compound as an oil.

Step 2: (5R)-5,6-Bis(nitrooxy)hexyl-(1R,2R)-2-{[3-({cyclopropyl[((3R,4S)-4-{4-[2-(2,6-dichloro-4-methylphenoxy)ethoxy]phenyl}piperidin-3-yl)carbonyl]amino}-methyl)-5-(3-methoxypropyl)phenoxy]methyl}cyclopropanecarboxylate Prepared according to the procedure described in Example 1/Step 4 but using instead tert-butyl (3R,4S)-3-{[[3-{[(1R,2R)-2-({[(5R)-5,6-bis(nitrooxy)hexyl]oxy}-carbonyl)cyclopropyl]methoxy}-5-(3-methoxypropyl)benzyl](cyclopropyl)amino]-carbonyl}-4-{4-[2-(2,6-dichloro-4-methylphenoxy)ethoxy]phenyl}piperidine-1-carboxylate from the previous step as the starting material. The title compound was a colorless oil.

$^1$H NMR (acetone d-6): δ (1 eq.) 7.29 (s, 2H), 7.20 (d, 2H), 6.82 (d, 2H), 6.60 (s, 1H), 6.49 (s, 1H), 6.40 (s, 1H), 5.52 (m, 1H), 5.03 (d, 1H), 4.75 (dd, 1H), 4.30-4.45 (m, 5H), 4.28 (d, 1H), 4.10 (t, 2H), 4.00 (dd, 1H), 3.80 (dd, 1H), 3.58 (dt, 1H), 3.02-3.35 (m, 8H), 2.70-2.90 (m, 2H), 2.53 (t, 2H), 2.30-2.35 (m, 4H), 1.55-1.95 (m, 12H), 1.02-1.20 (m, 2H), 0.45-0.9 (m, 4H).

LRMS [M+H]=945

EXAMPLE 7

Ethyl (1S,2S)-2-{[3-({cyclopropyl[((3R,4S)-4-{4-[2-(2,6-dichloro-4-methylphenoxy)-ethoxy]phenyl}piperidin-3-yl)carbonyl]amino}methyl)-5-(3-methoxypropyl)phen-oxy]methyl}cyclopropanecarboxylate

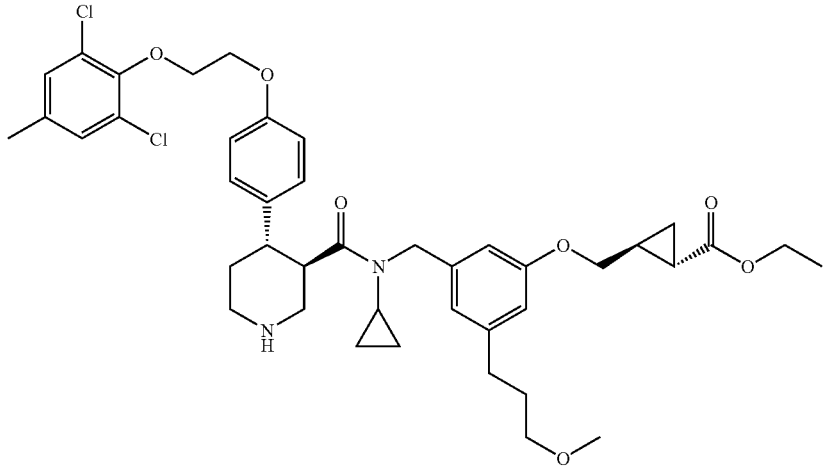 [SMILES: CCOC(=O)[C@H]1C[C@@H]1COc1cc(CCCOC)cc(CN(C(=O)[C@H]2CNCC[C@@H]2c2ccc(OCCOc3c(Cl)cc(C)cc3Cl)cc2)C2CC2)c1]

Prepared according to the procedure described in Example 1 but using instead ethyl (1S,2S)-2-(hydroxymethyl)cyclopropanecarboxylate (appendage 2) as the starting material in Step 3. The title compound was a colorless oil.

$^1$H NMR (acetone d-6): δ 7.28 (s, 2H), 7.20 (d, 2H), 6.83 (d, 2H), 6.60 (s, 1H), 6.47 (s, 1H), 6.40 (s, 1H), 4.30-4.42 (m, 5H), 4.27 (d, 1H), 4.05-4.15 (m, 2H), 4.0 (dd, 1H), 3.8 (dd, 1H), 3.55 (dt, 1H), 3.31 (t, 2H), 3.28 (s, 3H), 3.00-3.22 (m, 3H), 2.67-2.77 (m, 2H), 2.53 (t, 2H), 2.29-2.35 (m, 4H), 1.70-1.85 (m, 6H), 1.22 (t, 3H), 0.4-1.2 (m, 6H).

LRMS [M+H]=767.1

EXAMPLE 8

(1S,2S)-2-{[3-({Cyclopropyl[((3R,4S)-4-{4-[2-(2,6-dichloro-4-methylphenoxy)-ethoxy]phenyl}piperidin-3-yl)carbonyl]amino}methyl)-5-(3-methoxypropyl)phen-oxy]methyl}cyclopropanecarboxylic Acid

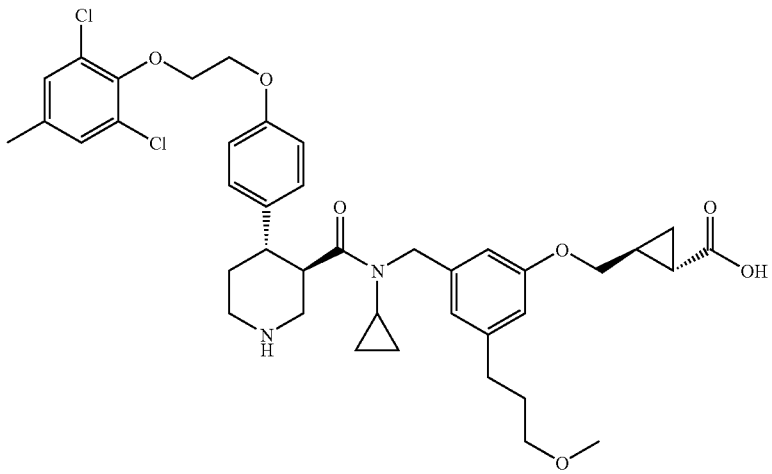 [SMILES: COCCCc1cc(CN(C(=O)[C@H]2CNCC[C@@H]2c2ccc(OCCOc3c(Cl)cc(C)cc3Cl)cc2)C2CC2)cc(OC[C@H]2C[C@@H]2C(=O)O)c1]

Prepared according to the procedure described in Example 2 but using instead ethyl (1S,2S)-2-{[3-({cyclopropyl[((3R,4S)-4-{4-[2-(2,6-dichloro-4-methylphenoxy)-ethoxy]phenyl}piperidin-3-yl)carbonyl]amino}methyl)-5-(3-methoxypropyl)phen-oxy]methyl}cyclopropanecarboxylate (Example 7) as the starting material. The sodium salt of the title compound was a foam.

$^1$H NMR (DMSO): δ 7.33 (s, 2H), 7.11 (d, 2H), 6.80 (d, 2H), 6.55 (s, 1H), 6.38 (s, 1H), 6.15 (s, 1H), 4.10-4.40 (m, 6H), 3.65-3.75 (m, 2H), 2.20-3.50 (m, 17H), 1.60-1.75 (m, 4H), 1.10-1.40 (m, 2H), 0.3-0.8 (m, 6H).

LRMS [M+H]=739.3 (for free acid)

EXAMPLE 9

Ethyl (1S,2S)-2-{[3-({cyclopropyl[((3R,4S)-4-{6-[2-(2,6-dichloro-4-methylphen-oxy)ethoxy]pyridin-3-yl}piperidin-3-yl)carbonyl]amino}methyl)-5-(3-methoxy-propyl)phenoxy]methyl}cyclopropanecarboxylate

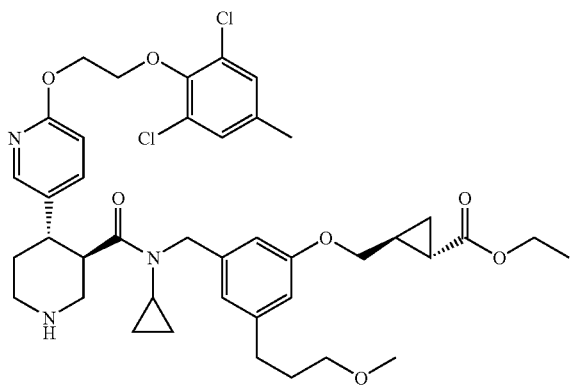 [SMILES: CCOC(=O)[C@H]1C[C@@H]1COc1cc(CCCOC)cc(CN(C(=O)[C@H]2CNCC[C@@H]2c2ccc(OCCOc3c(Cl)cc(C)cc3Cl)nc2)C2CC2)c1]

Prepared according to the procedure described in Example 1 but using instead (3R,4S)-1-(tert-butoxycarbonyl)-4-{6-[2-(2,6-dichloro-4-methylphenoxy)ethoxy]-pyridin-3-yl}piperidine-3-carboxylic acid (piperidine acid 2) as the starting material in Step 1 and ethyl (1S,2S)-2-(hydroxylmethyl)cyclopropanecarboxylate (appendage 2) as the starting material in Step 3. The title compound was a colorless oil.

$^1$H NMR (acetone d-6): δ 8.00 (s, 1H), 7.61 (d, 1H), 7.28 (s, 2H), 6.69 (d, 1H), 6.60 (s, 1H), 6.45 (s, 1H), 6.40 (s, 1H), 4.65 (t, 2H), 4.35-4.45 (m, 3H), 4.30 (d, 1H), 4.08-4.15 (m, 2H), 4.00 (dd, 1H), 3.80 (dd, 1H), 3.63 (dt, 1H), 3.05-3.35 (m, 8H), 2.70-2.90 (m, 2H), 2.52 (t, 2H), 2.40 (m, 1H), 2.31 (s, 3H), 1.70-1.90 (m, 6H), 1.24 (t, 3H), 1.02-1.20 (m, 2H), 0.45-0.91 (m, 4H).

LRMS [M+H]=768

EXAMPLE 10

(1S,2S)-2-{[3-({Cyclopropyl[((3R,4S)-4-{6-[2-(2,6-dichloro-4-methylphenoxy)-ethoxy]pyridin-3-yl}piperidin-3-yl)carbonyl]amino}methyl)-5-(3-methoxypropyl)-phenoxy]methyl}cyclopropanecarboxylic Acid

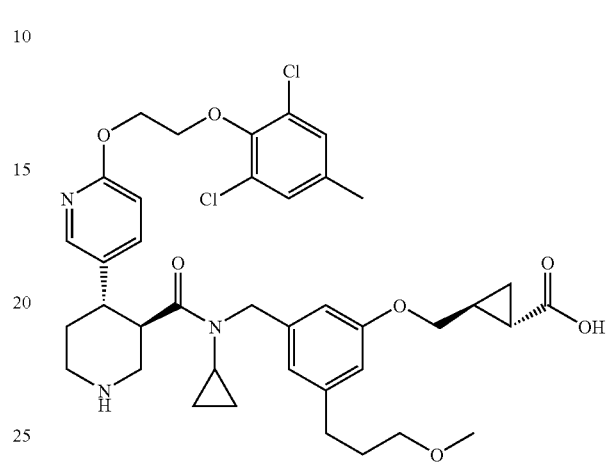

Prepared according to the procedure described in Example 2 but using instead ethyl (1S,2S)-2-{[3-({cyclopropyl[((3R,4S)-4-{6-[2-(2,6-dichloro-4-methylphen-oxy)ethoxy]pyridin-3-yl}piperidin-3-yl)carbonyl]amino}methyl)-5-(3-methoxy-propyl)phenoxy]methyl}cyclopropanecarboxylate (Example 9) as the starting material. The sodium salt of the title compound was a foam.

$^1$H NMR (acetone d-6): δ 8.02 (s, 1H), 7.6 (d, 1H), 7.2 (s, 2H), 6.67 (d, 1H), 6.45-6.55 (m, 2H), 6.30 (s, 1H), 4.60-4.67 (m, 2H), 4.05 (d, 1H), 4.30-4.40 (m, 2H), 3.90-4.05 (m, 2H), 2.25-3.70 (m, 18H), 1.50-1.90 (m, 6H), 0.3-0.9 (m, 6H).

LRMS [M+H]=740 (for free acid)

EXAMPLE 11

Methyl (1-{[3-({cyclopropyl[((3R,4S)-4-{4-[2-(2,6-dichloro-4-methylphenoxy)-ethoxy]phenyl}piperidin-3-yl)carbonyl]amino}methyl)-5-(3-methoxypropyl)phen-oxy]methyl}cyclopropyl)acetate

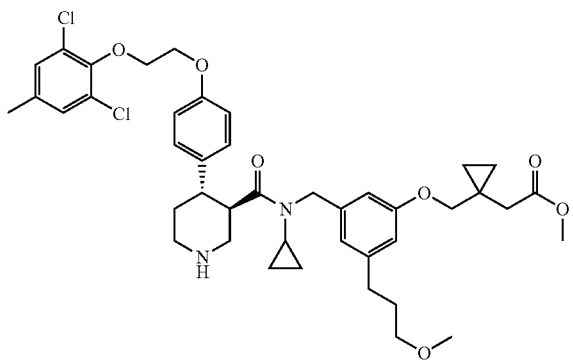

Step 1: tert-Butyl (3R,4S)-3-({cyclopropyl[3-{[1-(2-methoxy-2-oxoethyl)cyclo-propyl]methoxy}-5-(3-methoxypropyl)benzyl]amino}carbonyl)-4-{4-[2-(2,6-di-chloro-4-methylphenoxy)ethoxy]phenyl}piperidine-1-carboxylate To a solution of tert-butyl (3R,4S)-3-({cyclopropyl[3-hydroxy-5-(3-methoxy-propyl)benzyl]amino}carbonyl)-4-{4-[2-(2,6-dichloro-4-methylphenoxy)ethoxy]-phenyl}piperidine-1-carboxylate (1 eq.) from Example 1/Step 2 in DMF (0.1 M) was added methyl (1-{[(methylsulfonyl)oxy]methyl}cyclopropyl)acetate (appendage 3) (2 eq.) and cesium carbonate (2 eq.). The reaction was heated to 80° C. and stirred for 18 h. After cooling to rt, the reaction was diluted with ether. The organic extract was washed with water, brine, dried over MgSO$_4$, and concentrated in vacuo. The crude product was purified by flash column chromatography (SiO$_2$, 20% EtOAc in toluene) to afford the title compound as an oil.

Step 2: Methyl (1-{[3-({cyclopropyl[((3R,4S)-4-{4-[2-(2,6-dichloro-4-methyl-phenoxy)ethoxy]phenyl}piperidin-3-yl)carbonyl]amino}methyl)-5-(3-methoxy-propyl)phenoxy]methyl}cyclopropyl)acetate Prepared according to the procedure described in Example 1/Step 4 but using instead tert-butyl (3R,4S)-3-({cyclopropyl[3-{[1-(2-methoxy-2-oxoethyl)cyclo-propyl]methoxy}-5-(3-methoxypropyl)benzyl]amino}carbonyl)-4-{4-[2-(2,6-di-chloro-4-methylphenoxy)ethoxy]phenyl}piperidine-1-carboxylate from the previous step as the starting material. The title compound was a colorless oil.

$^1$H NMR (acetone d-6): δ 7.28 (s, 2H), 7.20 (d, 2H), 6.82 (d, 2H), 6.60 (s, 1H), 6.50 (s, 1H), 6.35 (s, 1H), 4.30-4.45 (m 6H), 3.85 (s, 2H), 3.61 (s, 3H), 3.51 (dt, 1H), 3.30 (t, 2H), 3.28 (s, 3H), 3.00-3.25 (m, 3H), 2.67-2.85 (m 2H), 2.49-2.56 (m, 4H), 2.25-2.35 (m, 4H), 1.70-1.83 m 4H), 0.4-0.85 (m, 8H).

LRMS [M+H]=767.1

EXAMPLE 12

(1-{[3-({Cyclopropyl[((3R,4S)-4-{4-[2-(2,6-dichloro-4-methylphenoxy)ethoxy]-phenyl}piperidin-3-yl)carbonyl]amino}methyl)-5-(3-methoxypropyl)phenoxy]-methyl}cyclopropyl)acetic Acid

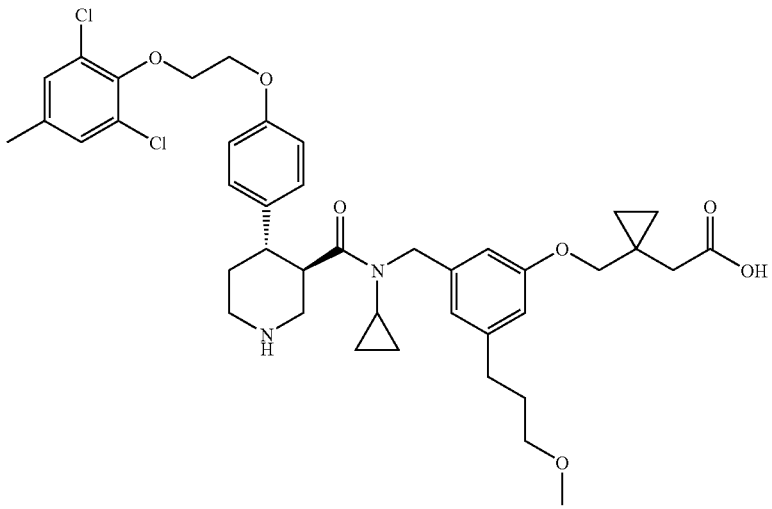 [SMILES: COCCCc1cc(CN(C(=O)[C@H]2CNCC[C@@H]2c2ccc(OCCOc3c(Cl)cc(C)cc3Cl)cc2)C2CC2)cc(OCC2(CC(=O)O)CC2)c1]

Prepared according to the procedure described in Example 2 but using instead methyl (1-{[3-({cyclopropyl[((3R,4S)-4-{4-[2-(2,6-dichloro-4-methylphenoxy)-ethoxy]phenyl}piperidin-3-yl)carbonyl]amino}methyl)-5-(3-methoxypropyl)phen-oxy]methyl}cyclopropyl)acetate (Example 11) as the starting material. The sodium salt of the title compound was a foam.

$^1$H NMR (acetone d-6): δ 7.27 (s, 2H), 7.20 (d, 2H), 6.84 (d, 2H), 6.55-6.66 (m, 2H), 6.38 (s, 1H), 4.59 (d, 1H), 4.30-4.41 (m, 5H), 3.90-4.10 (m, 2H), 3.50-3.60 (m, 1H), 2.20-3.35 (m, 18H), 1.65-1.81 (m, 4H), 0.3-0.8 (m, 8H).

LRMS [M+H]=753.2 (for free acid)

EXAMPLE 13

Benzyl (1-{[3-({cyclopropyl[((3R,4S)-4-{4-[2-(2,6-dichloro-4-methylphenoxy)-ethoxy]phenyl}piperidin-3-yl)carbonyl]amino}methyl)-5-(3-methoxypropyl)phen-oxy]methyl}cyclopropyl) acetate

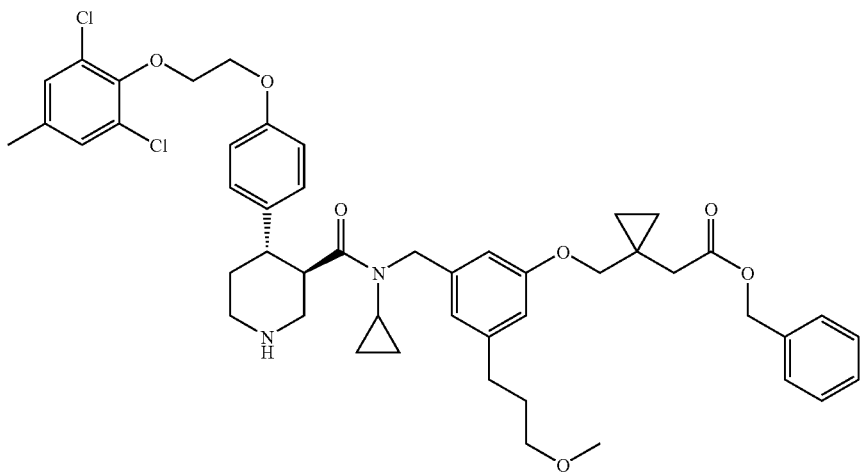 [SMILES: COCCCc1cc(CN(C(=O)[C@H]2CNCC[C@@H]2c2ccc(OCCOc3c(Cl)cc(C)cc3Cl)cc2)C2CC2)cc(OCC2(CC(=O)OCc3ccccc3)CC2)c1]

Step 1: (1-{[3-{[[((3R,4S)-1-(tert-Butoxycarbonyl)-4-{4-[2-(2,6-dichloro-4-methyl-phenoxy)ethoxy]phenyl}piperidin-3-yl)carbonyl](cyclopropyl)amino]methyl}-5-(3-methoxypropyl)phenoxy]methyl}cyclopropyl)acetic Acid To a solution of tert-butyl (3R,4S)-3-({cyclopropyl[3-{[1-(2-methoxy-2-oxoethyl)cyclopropyl]methoxy}-5-(3-methoxypropyl)benzyl]amino}carbonyl)-4-{4-[2-(2,6-dichloro-4-methylphenoxy)ethoxy]phenyl}piperidine-1-carboxylate (1 eq.) from Example 11/Step Step 1 in ethanol (0.1 M) was added 1 M aqueous NaOH (3 eq.). The reaction was heated at 100° C. in a microwave (Biotage) for 5 min. The reaction was cooled to rt and concentrated in vacuo. The residue was suspended in 1 N aqueous HCl and EtOAc. The aqueous layer was extracted several times with EtOAc. The combined organic extracts were washed with brine, dried over MgSO$_4$, and concentrated in vacuo to afford the title compound as a foam.

Step 2: tert-Butyl (3R,4S)-3-{[[3-({1-[2-(benzyloxy)-2-oxoethyl]cyclopropyl}-methoxy)-5-(3-methoxypropyl)benzyl](cyclopropyl)amino]carbonyl}-4-{4-[2-(2,6-dichloro-4-methylphenoxy)ethoxy]phenyl}piperidine-1-carboxylate To a solution of (1-{[3-{[[(3R,4S)-1-(tert-butoxycarbonyl)-4-{4-[2-(2,6-dichloro-4-methyl-phenoxy)ethoxy]phenyl}piperidin-3-yl)carbonyl](cyclopropyl)-amino]methyl}-5-(3-methoxypropyl)phenoxy]methyl}cyclopropyl)acetic acid (1 eq.) from the previous step in DMF (0.04 M) was added benzylbromide (1.2 eq.) and cesium carbonate (1.2 eq.). The reaction was stirred at rt for 18 h and then diluted with ether. The organic extract was washed with water, brine, dried over MgSO$_4$, and concentrated in vacuo. The crude product was purified by flash column chromatography (SiO$_2$, 30% EtOAc in Hex) to afford the title compound as an oil.

Step 3: Benzyl (1-{[3-({cyclopropyl[((3R,4S)-4-{4-[2-(2,6-dichloro-4-methyl-1-phenoxy)ethoxy]phenyl}piperidin-3-yl)carbonyl]amino}methyl)-5-(3-methoxy-propyl)phen-oxy]methyl}cyclopropyl) acetate Prepared according to the procedure described in Example 1/Step 4 but using instead tert-butyl (3R,4S)-3-{[[3-({1-[2-(benzyloxy)-2-oxoethyl]cyclopropyl}-methoxy)-5-(3-methoxypropyl)benzyl](cyclopropyl)amino]carbonyl}-4-{4-[2-(2,6-dichloro-4-methylphenoxy)ethoxy]phenyl}piperidine-1-carboxylate from the previous step as the starting material. The title compound was a colorless oil.

$^1$H NMR (acetone d-6): δ 7.30-7.40 (m, 5H), 7.28 (s, 2H) 7.20 (d, 2H), 6.82 (d, 2H), 6.59 (s, 1H), 6.50 (s, 1H), 6.35 (s, 1H), 5.11 (s, 2H), 4.30-4.43 (m, 6H), 3.85 (s, 2H), 3.52 (dt, 1H), 3.00-3.31 (m, 8H), 2.69-2.85 (m, 2H), 2.49-2.60 (m, 4H), 2.25-2.35 (m, 4H), 1.69-1.80 (m, 4H), 0.4-0.8 (m, 8H).

LRMS [M+H]=843.4

EXAMPLE 14

(3R,4S)—N-Cyclopropyl-4-{4-[2-(2,6-dichloro-4-methylphenoxy)ethoxy]phenyl}-N-(3-(3-methoxypropyl)-5-{[1-(2H-tetrazol-5-ylmethyl)cyclopropyl]methoxy}benzyl)-piperidine-3-carboxamide

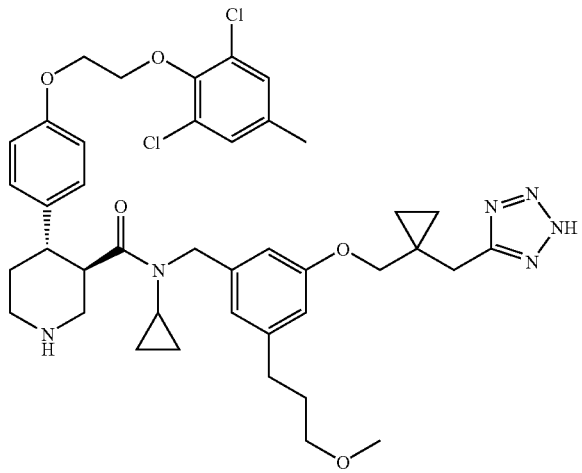 [SMILES: COCCCc1cc(CN(C(=O)[C@H]2CNCC[C@@H]2c2ccc(OCCOc3c(Cl)cc(C)cc3Cl)cc2)C2CC2)cc(OCC2(Cc3nn[nH]n3)CC2)c1]

Step 1: tert-Butyl (3R,4S)-3-{[[3-{[1-(cyanomethyl)cyclopropyl]methoxy}-5-(3-methoxypropyl)benzyl](cyclopropyl)amino]carbonyl}-4-{4-[2-(2,6-dichloro-4-methylphenoxy)ethoxy]phenyl}piperidine-1-carboxylate To a solution of tert-butyl (3R,4S)-3-({cyclopropyl[3-hydroxy-5-(3-methoxy-propyl)benzyl]amino}carbonyl)-4-{4-[2-(2,6-dichloro-4-methylphenoxy)ethoxy]-phenyl}piperidine-1-carboxylate (1 eq.) from Example 1/Step 2 in DMF (0.1 M) was added [1-(cyanomethyl)cyclopropyl]methyl methanesulfonate (appendage 4) (2 eq.) and cesium carbonate (2 eq.). The reaction was heated to 80° C. and stirred for 18 h. After cooling to rt, the reaction was diluted with ether. The organic extract was washed with water, brine, dried over MgSO$_4$, and concentrated in vacuo. The crude product was purified by flash column chromatography (SiO$_2$, 0%→50% EtOAc in toluene) to afford the title compound as an oil.

Step 2: ten-Butyl (3R,4S)-3-{[cyclopropyl(3-(3-methoxypropyl)-5-{[1-(2H-tetrazol-5-ylmethyl)cyclopropyl]methoxy}benzyl)amino]carbonyl}-4-{4-[2-(2,6-dichloro-4-methylphenoxy)ethoxy]phenyl}piperidine-1-carboxylate To a solution of tert-butyl (3R,4S)-3-{[[3-{[1-(cyanomethyl)cyclopropyl]-methoxy}-5-(3-methoxypropyl)benzyl](cyclopropyl)amino]carbonyl}-4-{4-[2-(2,6-dichloro-4-methylphenoxy)ethoxy]phenyl}piperidine-1-carboxylate (1 eq.) from the previous step in dioxane (0.17 M) was added tri-n-butyltin azide (3 eq.). The reaction was heated to 150° C. in a sealed tube for 18 h. After cooling down to rt, the reaction was diluted with EtOAc. The organic extract was washed with saturated aqueous NH$_4$Cl solution, brine, dried over MgSO$_4$, and concentrated in vacuo. The crude product was purified by flash column chromatography (SiO$_2$, first 50% EtOAc in Hex to 100% EtOAc, then 5% MeOH in DCM) to afford the title compound as an oil.

Step 3: (3R,4S)—N-Cyclopropyl-4-{4-[2-(2,6-dichloro-4-methylphenoxy)ethoxy]-phenyl}-N-(3-(3-methoxypropyl)-5-{[1-(2H-tetrazol-5-ylmethyl)cyclopropyl]-methoxy}benzyl)-piperidine-3-carboxamide Prepared according to the procedure described in Example 1/Step 4 but using instead tert-butyl (3R,4S)-3-{[cyclopropyl(3-(3-methoxypropyl)-5-{[1-(2H-tetrazol-5-ylmethyl)cyclopropyl]methoxy}benzyl)amino]carbonyl}-4-{4-[2-(2,6-dichloro-4-methylphenoxy)ethoxy]phenyl}piperidine-1-carboxylate from the previous step as the starting material. The crude product was purified by flash column chromatography (SiO$_2$, NH$_4$OH/MeOH/EtOAc 1:4:16) to afford the title compound as a colorless oil.

$^1$H NMR (acetone d-6): δ 7.27 (s, 2H), 7.19 (d, 2H), 6.88 (d, 2H), 6.77 (s, 1H), 6.75 (s, 1H), 6.57 (s, 1H), 5.3 (d, 1H), 4.39 (m, 4H), 4.0 (d, 1H), 3.68-3.55 (m, 3H), 3.4-3.32 (m, 4H), 3.29 (s, 3H), 3.09 (d, 1H), 2.95 (m, 1H), 2.65 (t, 2H), 2.40 (d, 1H), 2.32 (s, 3H), 2.30 (m, 2H), 1.85 (m, 4H), 1.12 (m, 1H), 0.95-0.55 (m, 8H).

LRMS [M+H]=777.1

EXAMPLE 15

Ethyl 4-[3-({cyclopropy[((3R,4S)-4-{4-[2-(2,6-dichloro-4-methylphenoxy)ethoxy]-phenyl}piperidin-3-yl)carbonyl]amino}methyl)-5-(3-methoxypropyl)phenoxy]-butanoate

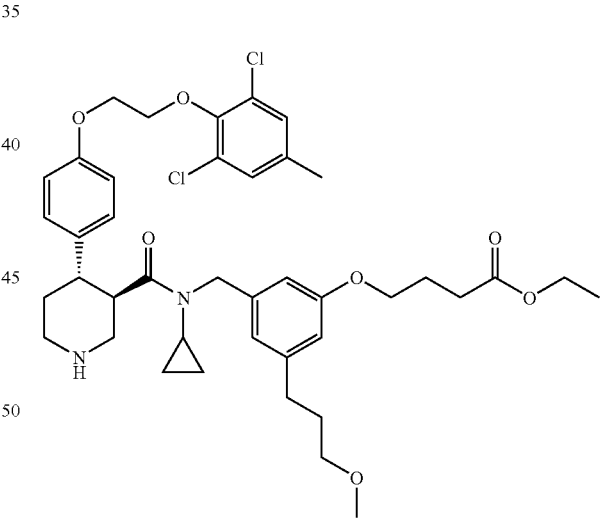

Step 1: tert-Butyl (3R,4S)-3-({cyclopropyl[3-(4-ethoxy-4-oxobutoxy)-5-(3-methoxy-propyl)benzyl]amino}carbonyl)-4-{4-[2-(2,6-dichloro-4-methylphenoxy)ethoxy]-phenyl}piperidine-1-carboxylate To a solution of tert-butyl (3R,4S)-3-({cyclopropyl[3-hydroxy-5-(3-methoxy-propyl)benzyl]amino}carbonyl)-4-{4-[2-(2,6-dichloro-4-methylphenoxy)ethoxy]-phenyl}piperidine-1-carboxylate (1 eq.) from Example 1/Step 2 in DMF (0.2 M) was added ethyl 4-bromobutanoate (1.6 eq.) and cesium carbonate (1.3 eq.). The reaction was heated to 80° C. for 3 h. After cooling down to rt, the reaction was diluted with EtOAc. The organic extract was washed with water, brine, dried over MgSO$_4$, and concentrated in vacuo. The crude product was purified by flash column chromatography (SiO$_2$, 50% EtOAc in Hex) to afford the title compound as an oil.

Step 2: Ethyl 4-[3-({cyclopropyl[3R,4S)-4-{4-[2-(2,6-dichloro-4-methylphenoxy)-ethoxy]phenyl}piperidin-3-yl)carbonyl]amino}methyl)-5-(3-methoxypropyl)phen-oxy]-butanoate Prepared according to the procedure described in Example 1/Step 4 but using instead tert-butyl (3R,4S)-3-({cyclopropyl[3-(4-ethoxy-4-oxobutoxy)-5-(3-methoxy-propyl)benzyl]amino}carbonyl)-4-{4-[2-(2,6-dichloro-4-methylphenoxy)ethoxy]-phenyl}piperidine-1-carboxylate from the previous step as the starting material. The title compound was a colorless oil.

$^1$H NMR (acetone d-6): δ 7.27 (s, 2H), 7.19 (d, 2H), 6.83 (d, 2H), 6.6 (s, 1H), 6.47 (s, 1H), 6.39 (s, 1H), 4.45-4.25 (m, 6H), 4.11 (q, 2H), 3.96 (t, 2H), 3.57 (m, 1H), 3.32 (t, 2H), 3.27 (s, 3H), 3.21 (m, 1H), 3.13 (m, 1H), 3.07 (m, 1H), 2.75 (m, 4H), 2.52 (m, 4H), 2.34 (m, 1H), 2.33 (s, 3H), 1.8 (m, 4H), 1.22 (t, 3H), 0.75 (m, 3H), 0.47 (m, 1H).
LRMS [M+H]=755.2

EXAMPLE 16

4-[3-({Cyclopropyl[((3R,4S)-4-{4-[2-(2,6-dichloro-4-methylphenoxy)ethoxy]phenyl}piperidin-3-yl)carbonyl]amino}methyl)-5-(3-methoxypropyl)phenoxy]butanoic Acid

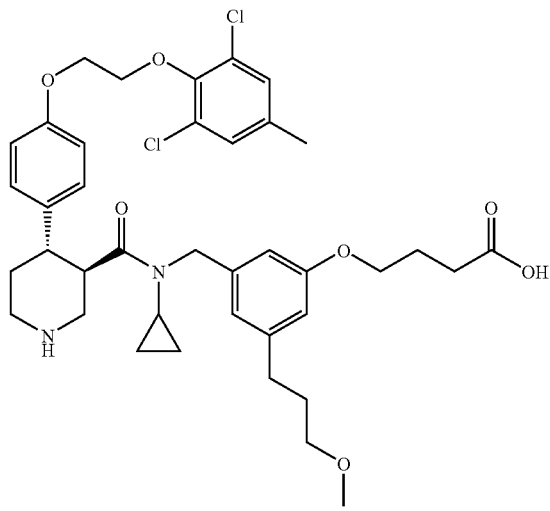 [SMILES: COCCCc1cc(CN(C(=O)[C@H]2CNCC[C@@H]2c2ccc(OCCOc3c(Cl)cc(C)cc3Cl)cc2)C2CC2)cc(OCCCC(=O)O)c1]

Prepared according to the procedure described in Example 2 but using instead ethyl 4-[3-({cyclopropyl[((3R,4S)-4-{4-[2-(2,6-dichloro-4-methylphenoxy)ethoxy]-phenyl}piperidin-3-yl)carbonyl]amino}methyl)-5-(3-methoxypropyl)phenoxy]-butanoate (Example 15) as the starting material. The sodium salt of the title compound was a foam.

$^1$H NMR (DMSO): δ 7.33 (s, 2H), 7.11 (d, 2H), 6.81 (d, 2H), 6.53 (s, 1H), 6.37 (s, 1H), 6.17 (s, 1H), 4.27 (m, 6H), 3.84 (t, 2H), 3.45-3.37 (m, 4H), 3.25 (t, 2H), 3.20 (s, 3H), 2.94 (m, 1H) 2.56 (m, 2H), 2.42 (t, 2H), 2.31 (m, 1H), 2.30 (s, 3H), 1.96 (t, 2H), 1.83-1.79 (m, 2H), 1.71-1.67 (m, 2H), 1.62 (d, 1H), 0.73 (m, 2H), 0.65 (m, 1H), 0.35 (m, 1H).
LRMS [M+H]=727.2 (for free acid)

EXAMPLE 17

(3R,4S)—N-Cyclopropyl-4-{4-[2-(2,6-dichloro-4-methylphenoxy)ethoxy]phenyl}-N-{3-(3-methoxypropyl)-5-[3-(2H-tetrazol-5-yl)propoxy]benzyl}piperidine-3-carboxamide

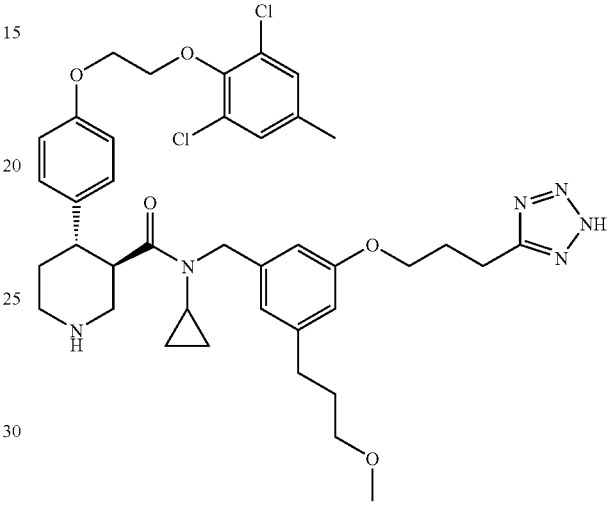

Step 1: tert-Butyl (3R,4S)-3-{[[3-(3-cyanopropoxy)-5-(3-methoxypropyl)benzyl]-(cyclopropyl)amino]carbonyl}-4-{4-[2-(2,6-dichloro-4-methylphenoxy)ethoxy]-phenyl}piperidine-1-carboxylate To a solution of tert-butyl (3R,4S)-3-({cyclopropyl[3-hydroxy-5-(3-methoxy-propyl)benzyl]amino}carbonyl)-4-{4-[2-(2,6-dichloro-4-methylphenoxy)ethoxy]-phenyl}piperidine-1-carboxylate (1 eq.) from Example 1/Step 2 in DMF (0.2 M) was added 4-bromobutanenitrile (1.2 eq.) and cesium carbonate (1.3 eq.). The reaction was stirred at rt for 18 h, then heated to 65° C. for 4 h. After cooling to rt, the reaction was diluted with EtOAc. The aqueous layer was extracted with EtOAc. The combined organic extracts were washed with saturated aqueous NH$_4$Cl solution, 5% aqueous HCl, saturated aqueous NaHCO$_3$ solution, and brine. The organic solution was dried over MgSO$_4$ and concentrated in vacuo to afford the title compound as an oil.

Step 2: tert-Butyl (3R,4S)-3-[(cyclopropyl {3-(3-methoxypropyl)-5-[3-(2H-tetrazol-5-yl)propoxy]benzyl}amino)carbonyl]-4-{4-[2-(2,6-dichloro-4-methylphenoxy)-ethoxy]phenyl}piperidine-1-carboxylate To a solution of tert-butyl (3R,4S)-3-{[[3-(3-cyanopropoxy)-5-(3-methoxy-propyl)benzyl](cyclopropyl)amino]carbonyl}-4-{4-[2-(2,6-dichloro-4-methylphen-oxy)ethoxy]-phenyl}piperidine-1-carboxylate (1 eq.) from previous step in dioxane (0.17 M) was added tri-n-butyltin azide (3 eq.). The reaction was heated to 150° C. in a sealed tube for 18 h. After cooling down to rt, the reaction was diluted with EtOAc. The organic extract was washed with saturated aqueous NH₄Cl solution, brine, dried over MgSO₄, and concentrated in vacuo. The crude product was purified by flash column chromatography (SiO₂, first 50% EtOAc in Hex to 100% EtOAc, then 5% MeOH in DCM) to afford the title compound as an oil.

Step 3: (3R,4S)—N-Cyclopropyl-4-{4-[2-(2,6-dichloro-4-methylphenoxy)ethoxy]-phenyl}-N-{3-(3-methoxypropyl)-5-[3-(2H-tetrazol-5-yl)propoxy]benzyl}piperidine-3-carbox-amide Prepared according to the procedure described in Example 1/Step 4 but using instead tert-butyl (3R,4S)-3-[cyclopropyl{3-(3-methoxypropyl)-5-[3-(2H-tetrazol-5-yl)propoxy]benzyl}amino)carbonyl]-4-{4-[2-(2,6-dichloro-4-methylphenoxy)-ethoxy]phenyl}piperidine-1-carboxylate from the previous step as the starting material. The crude product was purified by flash column chromatography (SiO₂, NH₄OH/MeOH/EtOAc 1:4:16) to afford the title compound as a colorless oil.
¹H NMR (acetone d-6): 7.28 (s, 2H), 7.19 (d, 2H), 6.88 (d, 2H), 6.70 (s, 2H), 6.53 (s, 1H), 5.29 (d, 1H), 4.40 (m, 4H), 3.85 (m, 1H), 3.76 (m, 1H), 3.64 (m, 2H), 3.42 (d, 1H), 3.36-3.31 (m, 4H), 3.28 (s, 3H), 3.18 (m, 1H), 3.08 (m, 1H); 2.95 (m, 1H), 2.62 (t, 2H), 2.43 (m, 2H), 2.35 (s, 3H), 2.15 (m, 1H), 1.92-1.82 (m, 4H), 1.08 (m, 1H), 0.75 (m, 3H), 0.55 (m, 1H).
LRMS [M+H]=751.2

EXAMPLE 18

Methyl 4-{[3-({cyclopropyl[((3R,4S)-4-{4-[2-(2,6-dichloro-4-methylphenoxy)-ethoxy]phenyl}piperidin-3-yl)carbonyl]amino}methyl)-5-(3-methoxypropyl)phen-oxy]methyl}benzoate

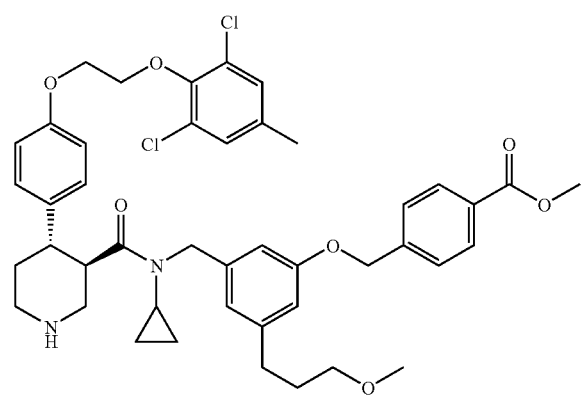 [SMILES: COCCCc1cc(CN(C(=O)[C@H]2CNCC[C@@H]2c2ccc(OCCOc3c(Cl)cc(C)cc3Cl)cc2)C2CC2)cc(OCc2ccc(C(=O)OC)cc2)c1]

Step 1: tert-Butyl (3R,4S)-3-({cyclopropyl[3-{[4-(methoxycarbonyl)benzyl]oxy}-5-(3-methoxypropyl)benzyl]amino}carbonyl)-4-{4-[2-(2,6-dichloro-4-methyl-phenoxy)ethoxy]phenyl}piperidine-1-carboxylate To a solution of tert-butyl (3R,4S)-3-({cyclopropyl[3-hydroxy-5-(3-methoxy-propyl)benzyl]amino}carbonyl)-4-{4-[2-(2,6-dichloro-4-methylphenoxy)ethoxy]-phenyl}piperidine-1-carboxylate (1 eq.) from Example 1/Step 2 in DMF (0.05 M) was added methyl 4-(bromomethyl)benzoate (1.6 eq.) and cesium carbonate (1.3 eq.). The reaction was heated to 80° C. and stirred for 12 h. After cooling to rt, the reaction was diluted with ether and quenched with water. The aqueous layer was extracted with ether. The combined organic extracts were washed with water, brine, dried over MgSO₄, and concentrated in vacuo. The crude product was purified by flash column chromatography (SiO₂, 5% EtOAc in Hex→100% EtOAc) to afford the title compound as a foam.

Step 2: Methyl 4-{[3-({cyclopropy[((3R,4S)-4-{4-[2-(2,6-dichloro-4-methyl-phenoxy)ethoxy]phenyl}piperidin-3-yl)carbonyl]amino}methyl)-5-(3-methoxy-propyl)phenoxy]methyl}benzoate Prepared according to the procedure described in Example 1/Step 4 but using instead tert-butyl (3R,4S)-3-({cyclopropyl[3-{[4-(methoxycarbonyl)benzyl]oxy}-5-(3-methoxypropyl)benzyl]amino}carbonyl)-4-{4-[2-(2,6-dichloro-4-methyl-phenoxy)ethoxy]phenyl-}piperidine-1-carboxylate from the previous step as the starting material. The title compound was a colorless oil.
¹H NMR (CDCl₃): δ 8.20 (d, 2H), 7.35 (d, 2H), 7.33 (d, 2H), 6.89 (d, 2H), 6.80 (s, 2H), 6.99 (s, 1H), 6.75 (s, 1H), 6.66 (s, 1H), 4.81 (s, 2H), 4.51 (d, 1H), 4.41 (d, 1H), 4.20 (t, 2H), 4.12-4.02 (m, 2H), 3.63-3.50 (m, 4H), 3.42 (td, 1H), 3.29 (t, 2H), 3.21 (s, 3H), 3.08 (t, 1H), 3.01 (d, 1H), 2.88-2.62 (m, 3H), 2.09-2.04 (m, 1H), 2.02 (s, 2H), 1.96-1.87 (m, 2H), 1.84 (td, 1H), 1.76 (s, 3H), 0.52-0.43 (m, 2H), 0.44-0.33 (m, 2H).
LRMS [M+H]=790.2

EXAMPLE 19

4-{[3-({Cyclopropyl[((3R,4S)-4-{4-[2-(2,6-dichloro-4-methylphenoxy)ethoxy]-phenyl}piperidin-3-yl)carbonyl]amino}methyl)-5-(3-methoxypropyl)phenoxy]-methyl}benzoic acid

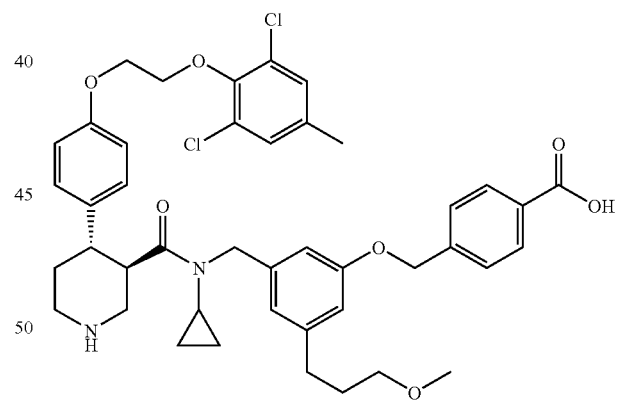

To a solution of methyl 4-{[3-({cyclopropyl[((3R,4S)-4-{4-[2-(2,6-dichloro-4-methylphenoxy)ethoxy]phenyl}piperidin-3-yl)carbonyl]amino}methyl)-5-(3-methoxypropyl)phenoxy]methyl}benzoate (1 eq.) from Example 18 in methanol (0.03) was added 1 N aqueous NaOH (2.2 eq.). The reaction was heated to reflux and stirred for 18 h. The volatiles were removed in vacuo and the resulting solid residue was triturated with ether. The resulting residue was then taken up in EtOAc and the insolubles were removed via filtration. To the filtrate was then slowly added ether to precipitate out the sodium salt of the title compound as a white solid.
¹H NMR (DMSO): δ 7.81 (d, 2H), 7.32 (s, 2H), 7.26 (d, 2H), 7.11 (d, 2H), 6.79 (d, 2H), 6.64 (s, 1H), 6.45 (s, 1H), 6.20

(s, 1H), 4.98 (s, 2H), 4.30-4.18 (m, 6H), 3.46-3.40 (m, 1H), 3.25 (t, 2H), 3.20 (s, 3H), 3.09-2.91 (m, 4H), 2.54-2.50 (m, 1H), 2.44 (t, 2H), 2.28 (s, 3H), 1.71-1.65 (m, 5H), 0.80-0.60 (m, 3H), 0.39-0.31 (m, 1H).
LRMS [M+H]=775.4

EXAMPLE 20

(3R,4S)—N-Cyclopropyl-4-{4-[2-(2,6-dichloro-4-methylphenoxy)ethoxy]phenyl}-N-(3-(3-methoxypropyl)-5-{[4-(1H-tetrazol-5-yl)benzyl]oxy}benzyl)piperidine-3-carboxamide

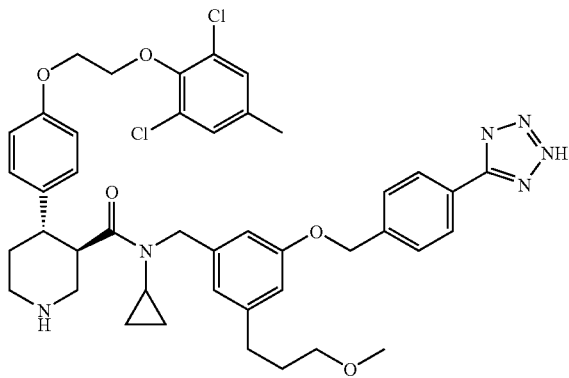 [SMILES: COCCCc1cc(CN(C(=O)[C@H]2CNCC[C@@H]2c2ccc(OCCOc3c(Cl)cc(C)cc3Cl)cc2)C2CC2)cc(OCc2ccc(-c3nnn[nH]3)cc2)c1]

Step 1: tert-Butyl (3R,4S)-3-([[3-[(4-cyanobenzyl)oxy]-5-(3-methoxypropyl)benzyl]-(cyclopropyl)amino]carbonyl}-4-{4-[2-(2,6-dichloro-4-methylphenoxy)ethoxy]-phenyl}piperidine-1-carboxylate To a solution of tert-butyl (3R,4 S)-3-({cyclopropyl[3-hydroxy-5-(3-methoxy-propyl)benzyl]amino}carbonyl)-4-{4-[2-(2,6-dichloro-4-methylphenoxy)ethoxy]-phenyl}piperidine-1-carboxylate (1 eq.) from Example 1/Step 2 in DMF (0.05 M) was added methyl 4-(bromomethyl)benzonitrile (1.6 eq.) and cesium carbonate (1.3 eq.). The reaction was heated to 80° C. and stirred for 16 h. After cooling to rt, the reaction was diluted with ether and quenched with water. The aqueous layer was extracted with ether. The combined organic extracts were washed with water, brine, dried over $MgSO_4$, and concentrated in vacuo. The crude product was purified by flash column chromatography ($SiO_2$, 5% EtOQc in Hex→100% EtOAc) to afford the title compound as a oil.

Step 2: tert-Butyl (3R,4S)-3-{[cyclopropyl(3-(3-methoxypropyl)-5-{[4-(1H-tetrazol-5-yl)benzyl]oxy}benzyl)amino]carbonyl}-4-{4-[2-(2,6-dichloro-4-methylphenoxy)-ethoxy]phenyl}piperidine-1-carboxylate To a solution of tert-butyl (3R,4S)-3-([[3-[(4-cyanobenzyl)oxy]-5-(3-methoxy-propyl)benzyl](cyclopropyl)amino]carbonyl}-4-{4-[2-(2,6-dichloro-4-methylphen-oxy)ethoxy]phenyl}piperidine-1-carboxylate (1 eq.) from the previous step in toluene (0.04 M) was added azido(trimethyl)silane (3 eq.) and dibutyltin oxide (0.25 eq.). The reaction was heated to 105° C. and stirred for 16 h. The volatiles were removed in vacuo and the crude product was purified by flash column chromatography ($SiO_2$, 95.9:3.9:0.2 (v/v/v) DCM/MeOH/AcOH) to afford the title compound as an oil.

Step 3: (3R,4S)—N-Cyclopropyl-4-{4-[2-(2,6-dichloro-4-methylphenoxy)ethoxy]-phenyl}-N-(3-(3-methoxypropyl)-5-{[4-(1H-tetrazol-5-yl)benzyl]oxy}benzyl)-piperidine-3-carboxamide Prepared according to the procedure described in Example 1/Step 4 but using instead tert-butyl (3R,4S)-3-{[cyclopropyl(3-(3-methoxypropyl)-5-{[4-(1H-tetrazol-5-yl)benzyl]oxy}benzyl)amino]carbonyl}-4-{4-[2-(2,6-dichloro-4-methylphenoxy)-ethoxy]phenyl}piperidine-1-carboxylate from the previous step as the starting material. The title compound was a colorless oil.
$^1$H NMR ($CD_3OD$): δ 8.03 (d, 2H), 7.51 (d, 2H), 7.20 (s, 2H), 7.04 (d, 2H), 6.76 (s, 1H), 6.73 (d, 2H), 6.45 (s, 1H), 6.44 (s, 1H), 5.16 (s, 2H), 4.50, (d, 1H), 4.32-4.13 (m, 4H), 4.06 (d, 1H), 3.80 (dt, 1H), 3.55 (d, 1H), 3.43-3.28 (m, 7H), 3.22-3.10 (m, 2H), 3.05 (dt, 1H), 2.59 (t, 2H), 2.30 (s, 3H), 2.18-2.06 (m, 1H), 1.85-1.78 (m, 3H), 0.86-0.79 (m, 1H), 0.68-0.53 (m, 2H), 0.48-0.41 (m, 1H).
LRMS [M+H]=799.1

EXAMPLE 21

Methyl 4-[3-({cyclopropyl[((3R,4S)-4-{4-[2-(2,6-dichloro-4-methylphenoxy)ethoxy]phenyl}piperidin-3-yl)carbonyl]amino}methyl)-5-(3-methoxypropyl)phenoxy]-2,2-dimethylbutanoate

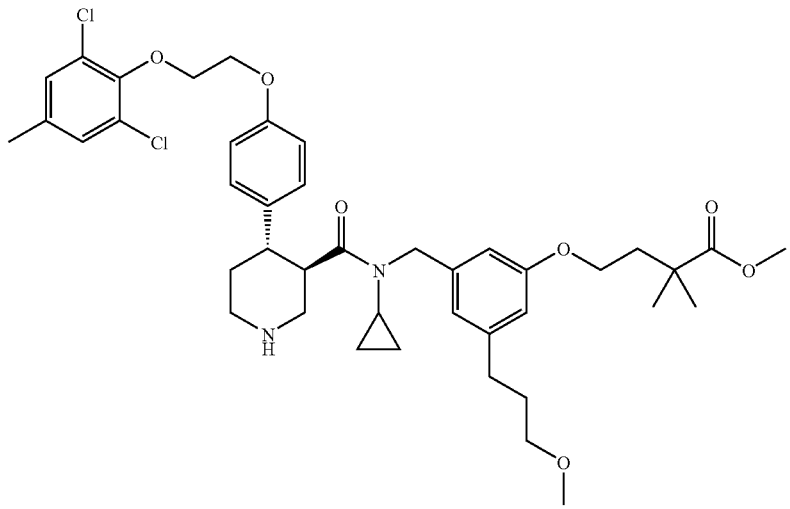

Step 1: tert-Butyl (3R,4S)-3-({cyclopropyl[3-(4-methoxy-3,3-dimethyl-4-oxobutoxy)-5-(3-methoxypropyl)benzyl]amino}carbonyl)-4-{4-[2-(2,6-dichloro-4-methylphenoxy)ethoxy]-phenyl}piperidine-1-carboxylate To a solution of tert-butyl (3R,4S)-3-({cyclopropyl[3-hydroxy-5-(3-methoxy-propyl)benzyl]amino}carbonyl)-4-{4-[2-(2,6-dichloro-4-methylphenoxy)ethoxy]-phenyl}piperidine-1-carboxylate (1 eq.) from Example 1/Step 2 in DMF (0.1 M) was added methyl 4-hydroxy-2,2-dimethylbutanoate (appendage 5) (2 eq.) and cesium carbonate (2 eq.). The reaction was heated to 80° C. and stirred for 18 h. After cooling to rt, the reaction was diluted with ether. The organic extract was washed with water, brine, dried over MgSO$_4$, and concentrated in vacuo. The crude product was purified by flash column chromatography (SiO$_2$, 20% EtOAc in toluene) to afford the title compound as an oil.

Step 2: Methyl 4-[3-({cyclopropyl[((3R,4S)-4-{4-[2-(2,6-dichloro-4-methylphenoxy)ethoxy]phenyl}-piperidin-3-yl)carbonyl]amino}methyl)-5-(3-methoxypropyl)phenoxy]-2,2-dimethylbutanoate Prepared according to the procedure described in Example 1/Step 4 but using instead tert-butyl (3R,4S)-3-({cyclopropyl[3-(4-methoxy-3,3-dimethyl-4-oxobutoxy)-5-(3-methoxypropyl)-benzyl]amino}carbonyl)-4-{4-[2-(2,6-dichloro-4-methylphenoxy)ethoxy]phenyl}piperidine-1-carboxylate from the previous step as the starting material. The title compound was a colorless oil.

$^1$H NMR (acetone d-6): δ 7.29 (s, 2H), 7.20 (s, 2H), 6.85 (d, 2H), 6.59 (s, 1H), 6.48 (s, 1H), 6.39 (s, 1H), 4.3-4.45 (m, 7H), 3.97 (t, 2H), 3.67 (s, 3H), 3.55 (t, 1H), 3.33 (t, 2H), 3.30 (s, 3H), 3.04-3.25 (m, 3H), 2.7-2.9 (m, 3H), 2.55 (t, 2H), 2.3-2.4 (m, 4H), 1.7-1.85 (m, 4H), 1.25 (s, 6H), 0.4-0.9 (m, 4H).
LRMS [M+H]=769.2

EXAMPLE 22

4-[3-({Cyclopropyl[((3R,4S)-4-{4-[2-(2,6-dichloro-4-methylphenoxy)ethoxy]phenyl}piperidin-3-yl)carbonyl]amino}methyl)-5-(3-methoxypropyl)phenoxy]-2,2-dimethylbutanoic Acid

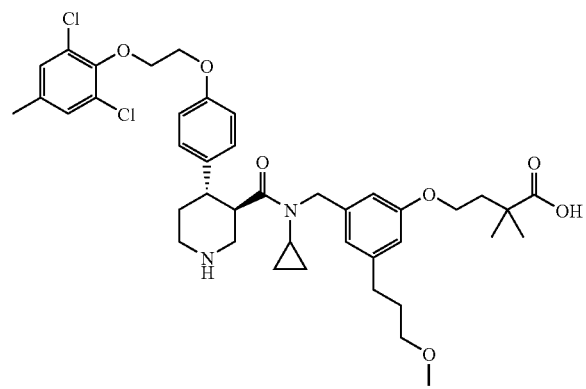 [SMILES: COCCCc1cc(CN(C(=O)[C@H]2CNCC[C@@H]2c2ccc(OCCOc3c(Cl)cc(C)cc3Cl)cc2)C2CC2)cc(OCCC(C)(C)C(=O)O)c1]

Step 1: 4-[3-{[[((3R,4S)-1-(tert-Butoxycarbonyl)-4-{4-[2-(2,6-dichloro-4-methylphenoxy)ethoxy]phenyl}piperidin-3-yl)carbonyl](cyclopropyl)amino]methyl}-5-(3-methoxypropyl)phenoxy]-2,2-dimethylbutanoic acid To a solution of tert-Butyl (3R,4S)-3-({cyclopropyl[3-(4-methoxy-3,3-dimethyl-4-oxobutoxy)-5-(3-methoxypropyl)-benzyl]amino}carbonyl)-4-{4-[2-(2,6-dichloro-4-methylphenoxy)ethoxy]phenyl}-piperidine-1-carboxylate (1 eq.) from Example 21/Step 2 in ethanol was added 1 N aqueous NaOH (3 eq.). The reaction was heated to 100° C. for 10 min in a microwave reactor (Biotage). After cooling to rt, the reaction was concentrated in vacuo to removed the ethanol solvent. The resulting solution was acidified with 1 N HCl and extracted with ethyl acetate. The combined organic extracted were dried over anhydrous Na$_2$SO$_4$ and concentrated in vacuo. The crude product was used in the next step without further purification.

Step 2: 4-[3-({Cyclopropyl[((3R,4S)-4-{4-[2-(2,6-dichloro-4-methylphenoxy)ethoxy]phenyl}piperidin-3-yl)carbonyl]amino}methyl)-5-(3-methoxypropyl)phenoxy]-2,2-dimethylbutanoic Acid Prepared according to the procedure described in Example 1/Step 4 but using instead 4-[3-{[[((3R,4S)-1-(tert-butoxycarbonyl)-4-{4-[2-(2,6-dichloro-4-methylphenoxy)ethoxy]phenyl}piperidin-3-yl)carbonyl](cyclopropyl)amino]methyl}-5-(3-methoxypropyl)phenoxy]-2,2-dimethylbutanoic acid from the previous step as the starting material. The crude product was purified by flash column chromatography (SiO$_2$, 15-20% MeOH in DCM) to afford the title compound as a foam.

$^1$H NMR (acetone d-6): δ 7.27-7.30 (m, 4H), 6.94 (d, 2H), 6.60 (s, 1H), 6.55 (s, 1H), 6.24 (s, 1H), 5.13 (d, 1H), 4.39-4.42 (m, 4H), 4.20 (t, 1H), 3.90-3.95 (m, 2H), 3.60 (d, 1H), 3.25-3.50 (m, 8H), 3.10 (t, 1H), 2.90 (t, 1H), 2.56 (t, 2H), 2.32 (s, 3H), 2.08-2.30 (m, 3H), 1.7-2.0 (m, 4H), 1.30 (d, 6H), 0.2-0.9 (m, 4H).

LRMS [M+H]=755.2 (for free acid)

Biological Activities

| Compound | Structure | Renin buffer (nM) | Renin plasma (nM) |
|---|---|---|---|
| Example 1 | 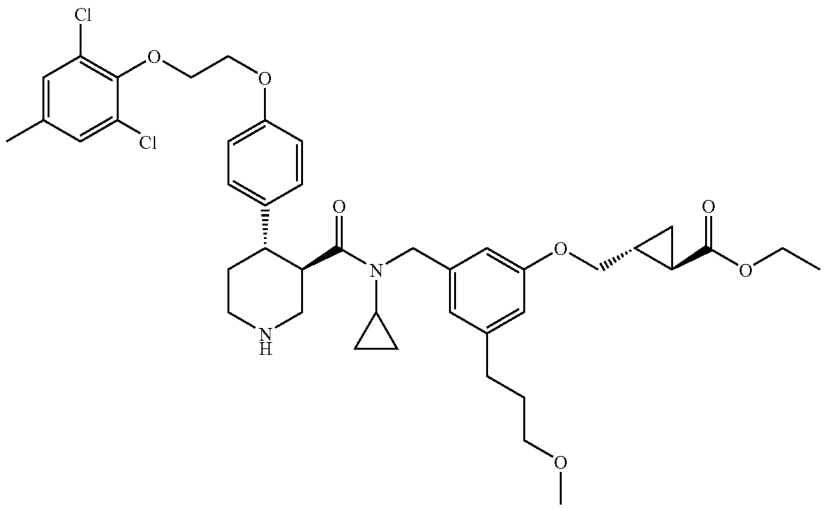 [SMILES: CCOC(=O)[C@@H]1C[C@H]1COc1cc(CCCOC)cc(CN(C(=O)[C@H]2CNCC[C@@H]2c2ccc(OCCOc3c(Cl)cc(C)cc3Cl)cc2)C2CC2)c1] | 0.064 | 11 |
| Example 2 | 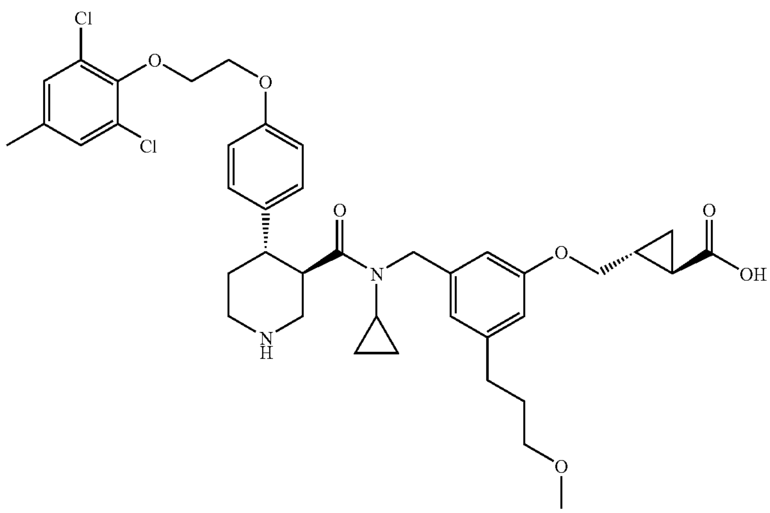 [SMILES: COCCCc1cc(CN(C(=O)[C@H]2CNCC[C@@H]2c2ccc(OCCOc3c(Cl)cc(C)cc3Cl)cc2)C2CC2)cc(OC[C@@H]2C[C@H]2C(=O)O)c1] | 0.027 | 1.1 |
| Example 12 | 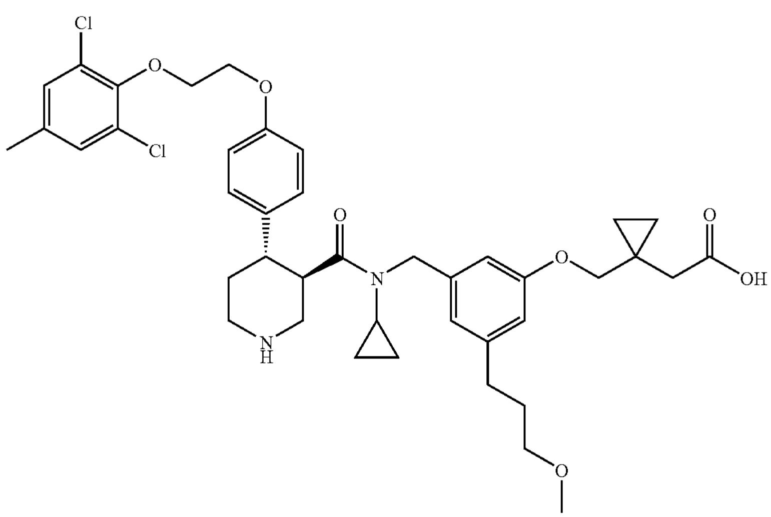 [SMILES: COCCCc1cc(CN(C(=O)[C@H]2CNCC[C@@H]2c2ccc(OCCOc3c(Cl)cc(C)cc3Cl)cc2)C2CC2)cc(OCC2(CC(=O)O)CC2)c1] | 0.036 | 5.6 |

-continued
| Compound | Structure | Renin buffer (nM) | Renin plasma (nM) |
|---|---|---|---|
| Example 16 | 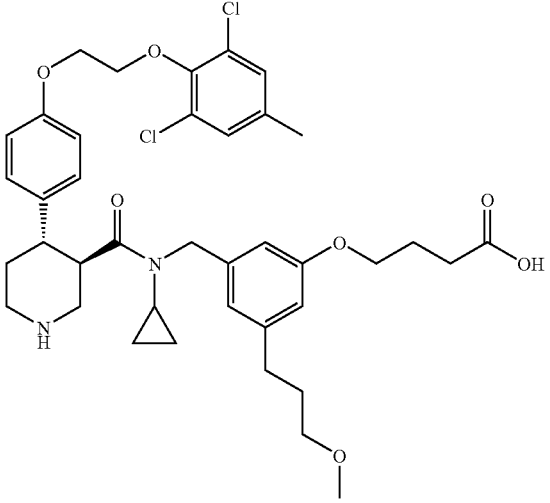 [SMILES: COCCCc1cc(CN(C(=O)[C@H]2CNCC[C@@H]2c2ccc(OCCOc3c(Cl)cc(C)cc3Cl)cc2)C2CC2)cc(OCCCC(=O)O)c1] | 0.014 | 1.5 |
| Example 19 | 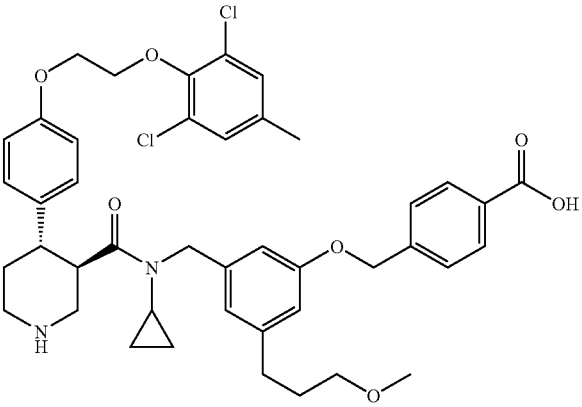 [SMILES: COCCCc1cc(CN(C(=O)[C@H]2CNCC[C@@H]2c2ccc(OCCOc3c(Cl)cc(C)cc3Cl)cc2)C2CC2)cc(OCc2ccc(C(=O)O)cc2)c1] | 0.052 | 9.4 |
| Example 14 | 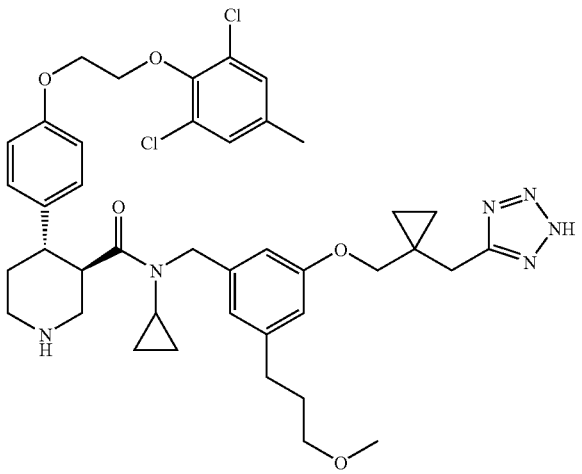 [SMILES: COCCCc1cc(CN(C(=O)[C@H]2CNCC[C@@H]2c2ccc(OCCOc3c(Cl)cc(C)cc3Cl)cc2)C2CC2)cc(OCC2(Cc3nn[nH]n3)CC2)c1] | 0.030 | 2.3 |

What is claimed is:

1. A compound of formula I, or a pharmaceutically acceptable salt thereof, or an optical isomer thereof, having the formula I

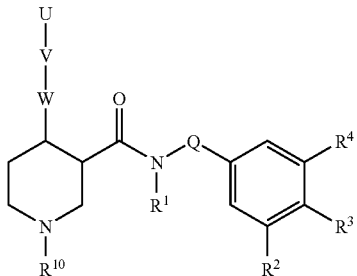

wherein
$R^1$ is $C_1$-$C_6$ alkyl or $C_3$-$C_7$ cycloalkyl;
$R^2$ is —O(CH$_2$)$_{1-3}$OCH$_3$ or —(CH$_2$)$_{1-3}$OCH$_3$;
$R^3$ is selected from the group consisting of:
  hydrogen,

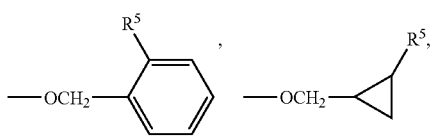

and
  —O(CH$_2$)$_2$C(CH$_3$)$_2$R$^5$;
$R^4$ is selected from the group consisting of:
  hydrogen,
  —C(O)OCH$_3$,
  —C(O)NH—C$_1$-C$_6$ alkyl,
  —COOH,

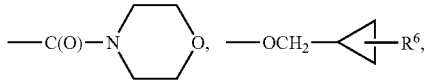

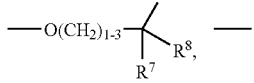

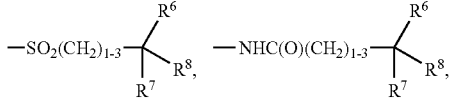

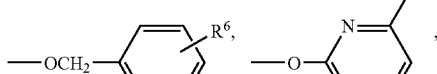

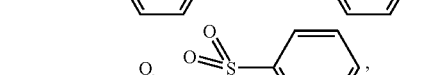

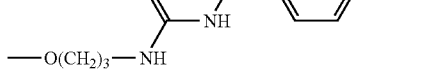

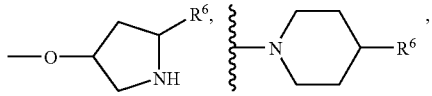

-continued

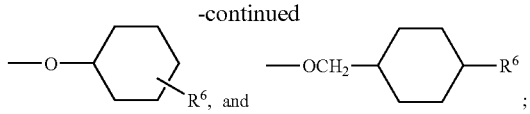

$R^5$ is selected from the group consisting of —COOH, —COOC$_1$-C$_6$ alkyl;
$R^6$ is selected from the group consisting of:
  —COOR$^9$,
  —CH$_2$COOR$^9$,
  —CON(CH$_3$)SO$_2$CH$_3$,
  —CONHSO$_2$CH$_3$,
  —C(O)NH$_2$
  —CH(CH$_2$CH$_3$)COOH,
  —CONHSO$_2$CH$_3$,
  —NH$_2$,

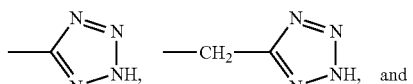

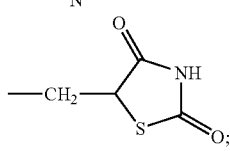

$R^7$ and $R^8$ are independently selected from the group consisting of:
  hydrogen,
  —C$_{1-6}$ alkyl,
  —OH,
  —OCH$_3$,
  —COOH,
  —NH$_2$, and

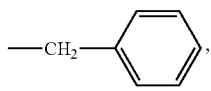

or $R^7$ and $R^8$, together with the atom to which they are attached, form a C$_{3-8}$ cycloalkyl ring;
$R^9$ is selected from the group consisting of:
  hydrogen,
  —C$_1$-C$_6$alkyl,
  —(CH$_2$)$_{2-4}$CH(ONO$_2$)CH$_2$ONO$_2$,
  —CH$_2$C(O)N(CH$_3$)$_2$,
  —CH$_2$OCOC(CH$_3$)$_3$,
  —CH$_2$OCH$_2$OCOCH$_3$,
  —CH(CH$_3$)OCOCH(CH$_3$)$_2$,
  —CH(CH$_3$)COOCH$_2$CH$_3$,
  —CH$_2$CH$_2$N(CH$_3$)$_2$,
  —CH(CH$_3$)OCOOCH$_2$CH$_3$,
  —CH(CH$_3$)OCOOCH(CH$_3$)$_2$,

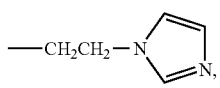

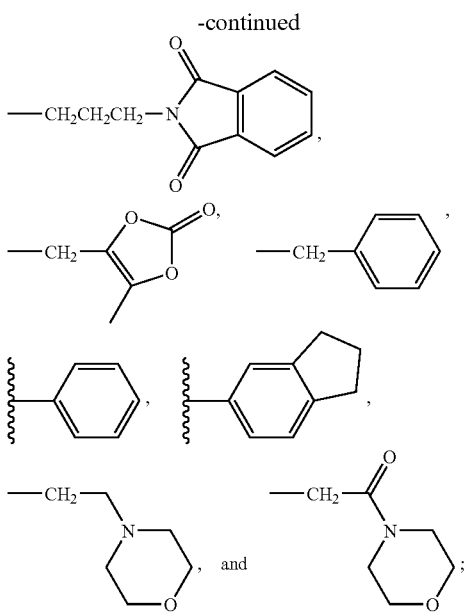

$R^{10}$ is selected from the group consisting of:
hydrogen,
—COOCH$_3$,
—COOCH(CH$_3$)OCOCH$_3$,

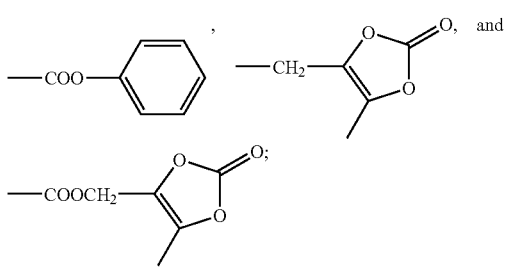

W is a phenyl ring or a six-membered, aromatic ring containing one to four nitrogen atoms, wherein said rings are substituted by V in para position;

V is a bond; —(CH$_2$)$_r$—; -A-(CH$_2$)$_s$—; —CH$_2$-A-(CH$_2$)$_t$—; —(CH$_2$)$_s$-A-; —(CH$_2$)$_2$-A-(CH$_2$)$_u$—; -A-(CH$_2$)$_v$—B—; —CH$_2$—CH$_2$—CH$_2$-A-CH$_2$—; -A-CH$_2$—CH$_2$—B—CH$_2$—; —CH$_2$-A-CH$_2$—CH$_2$—B—; —CH$_2$—CH$_2$—CH$_2$-A-CH$_2$—; -A-CH$_2$—CH$_2$—B—CH$_2$—CH$_2$—; —CH$_2$-A-CH$_2$—CH$_2$—B—CH$_2$—; —CH$_2$-A-CH$_2$—CH$_2$—CH$_2$—B—; —CH$_2$—CH$_2$-A-CH$_2$—CH$_2$—B—; —O—CH$_2$—CH(OCH$_3$)—CH$_2$—O—; —O—CH$_2$—CH(CH$_3$)—CH$_2$—O—; —O—CH$_2$—CH(CF$_3$)—CH$_2$—O—; —O—CH$_2$—C(CH$_3$)$_2$—CH$_2$—O—; —O—CH$_2$—C(CH$_3$)$_2$—O—; —O—C(CH$_3$)$_2$—CH$_2$—O—; —O—CH$_2$—CH(CH$_3$)—O—; —O—CH(CH$_3$)—CH$_2$—O—; —O—CH$_2$—C(CH$_2$CH$_3$)—O—; or —O—C(CH$_2$CH$_3$)—CH$_2$—O—;

A and B are independently selected from the group consisting of —O—, —S—, —S(O)— and —S(O)$_2$—;

U is unsubstituted aryl; mono-, di-, tri- or tetra-substituted aryl wherein the substituents are independently selected from the group consisting of halogen, alkyl, alkoxy, and —CF$_3$; or mono-, di-, or tri-substituted heteroaryl wherein the substituents are independently selected from the group consisting of halogen, alkyl, alkoxy, and —CF$_3$;

Q is methylene or ethylene;

n is the integer 0 or 1;

r is the integer 3, 4, 5, or 6;

s is the integer 2, 3, 4, or 5;

t is the integer 1, 2, 3, or 4;

u is the integer 1, 2, or 3; and v is the integer 2, 3, or 4.

2. A compound of claim 1, or a pharmaceutically acceptable salt thereof, wherein Q is methylene.

3. A compound of claim 1, or a pharmaceutically acceptable salt thereof, wherein $R^1$ is cyclopropyl.

4. A compound of claim 1, or a pharmaceutically acceptable salt thereof, wherein W is phenyl substituted by V in the para position.

5. A compound of claim 1, or a pharmaceutically acceptable salt thereof, wherein V is —CH$_2$CH$_2$O—, —CH$_2$CH$_2$CH$_2$O—, or —OCH$_2$CH$_2$O—, wherein the bivalent radical is linked to the group U of formula (I) via an oxygen atom.

6. A compound of claim 5, or a pharmaceutically acceptable salt thereof, wherein V is —OCH$_2$CH$_2$O—.

7. A compound of claim 1, or a pharmaceutically acceptable salt thereof, wherein U is a mono-, di-, or tri-substituted phenyl wherein the substituents are independently selected from the group consisting of halogen, C$_1$-C$_6$ alkyl, C$_1$-C$_6$ alkoxy, and —CF$_3$.

8. A compound of claim 7, or a pharmaceutically acceptable salt thereof, wherein U is 2,6-dichloro-4-methyl-phenyl.

9. A compound of claim 1, or a pharmaceutically acceptable salt thereof, wherein $R^2$ is —O(CH$_2$)$_2$OCH$_3$ or —(CH$_2$)$_3$OCH$_3$.

10. A compound of claim 1, or a pharmaceutically acceptable salt thereof, wherein $R^3$ is selected from the group consisting of:
hydrogen,

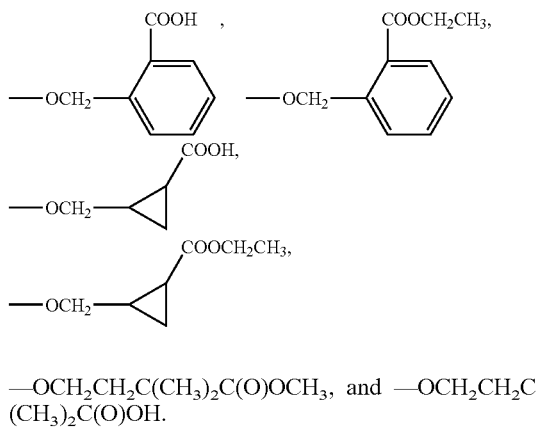

—OCH$_2$CH$_2$C(CH$_3$)$_2$C(O)OCH$_3$, and —OCH$_2$CH$_2$C(CH$_3$)$_2$C(O)OH.

11. A compound of claim 1, or a pharmaceutically acceptable salt thereof, wherein $R^7$ and $R^8$ are independently selected from the group consisting of:
hydrogen,
—CH$_3$,
—CH$_2$CH$_3$,
—OH, —OCH₃,
—COOH,
—NH₂, and

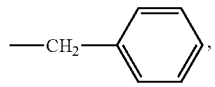

or R⁷ and R⁸, together with the atom to which they are attached, form a cycloalkyl ring selected from the group consisting of cyclopropyl, cyclobutyl, cyclopentyl, and cyclohexyl.

12. A compound of claim 1, or a pharmaceutically acceptable salt thereof, wherein R⁴ is selected from the group consisting of:

hydrogen,
—C(O)OCH₃,
—COOH,

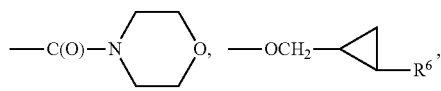

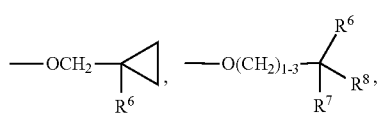

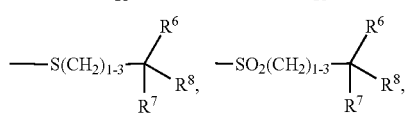

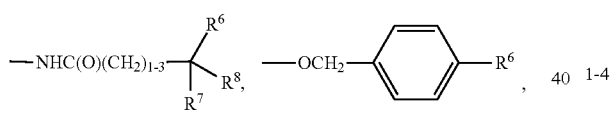

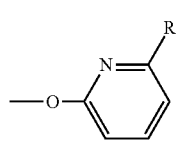

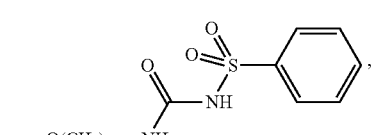

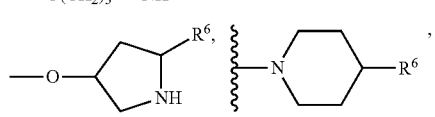

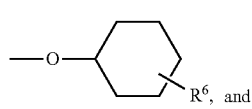

13. A compound of claim 1, or a pharmaceutically acceptable salt thereof, selected from the group consisting of compounds listed in the following tables:

TABLE 1

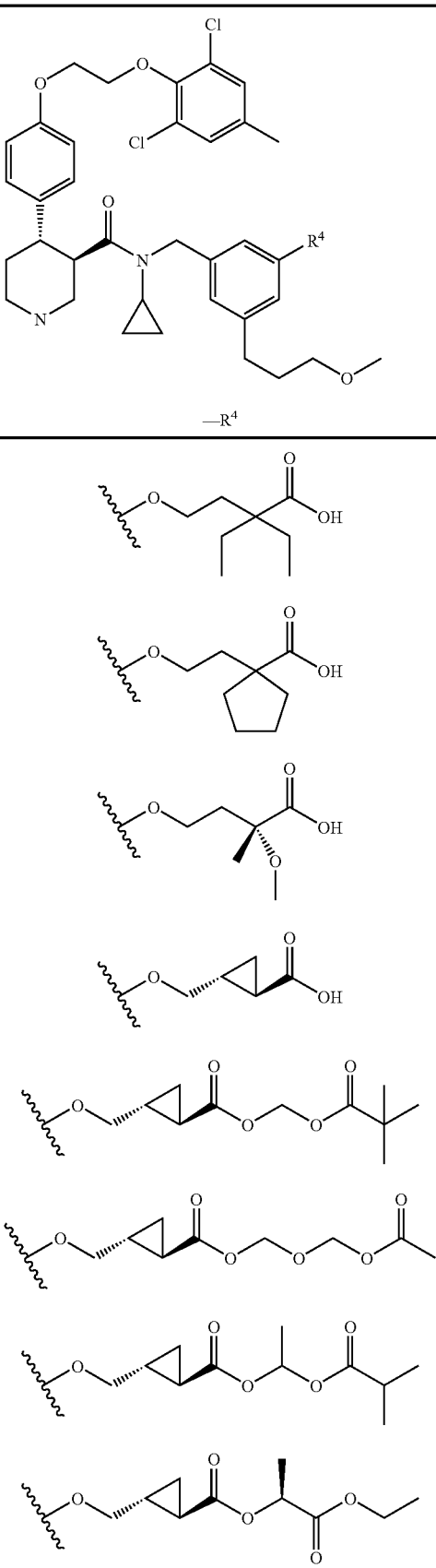

TABLE 1-continued

| | —R⁴ |
|---|---|
| 1-9 | (4-benzyl group with thiazolidine-2,4-dione) |
| 1-10 | (4-benzyloxymethyl phenylacetic acid) |
| 1-11 | (pyridine-2-carboxylic acid, 6-oxy linked) |
| 1-12 | (O-propyl chain with 2-benzyl carboxylic acid) |
| 1-13 | (OCH₂-cyclopropane-C(O)O-CH₂CH₂-N(CH₃)₂) |
| 1-14 | (OCH₂-cyclopropane-C(O)O-CH₂CH₂-imidazole) |
| 1-15 | (OCH₂-cyclopropane-C(O)O-propyl-phthalimide) |

TABLE 1-continued

| | —R⁴ |
|---|---|
| 1-16 | (O-CH₂-C(CH₃)₂-COOH) |
| 1-17 | (O-CH₂-C(CH₃)₂-C(O)OCH₃) |
| 1-18 | (OCH₂-cyclopropane-C(O)-N(CH₃)-SO₂CH₃) |
| 1-19 | (O-propyl-NH-C(O)-NH-SO₂-phenyl) |
| 1-20 | (O-propyl-C(CH₃)₂-C(O)OCH₃) |
| 1-21 | (O-propyl-C(CH₃)₂-COOH) |
| 1-22 | (OCH₂-cyclopropane-C(O)-NH-SO₂CH₃) |
| 1-23 | (O-CH₂CH₂-C(CH₃)(OH)-COOH) |

TABLE 1-continued
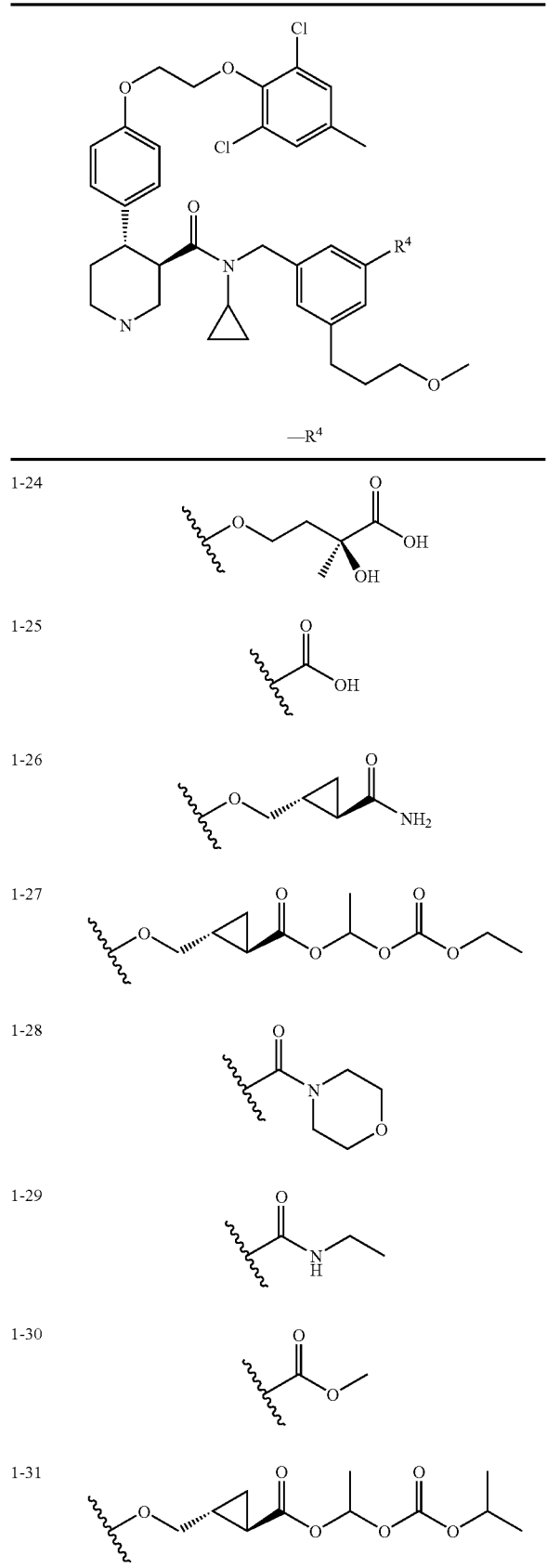
TABLE 1-continued
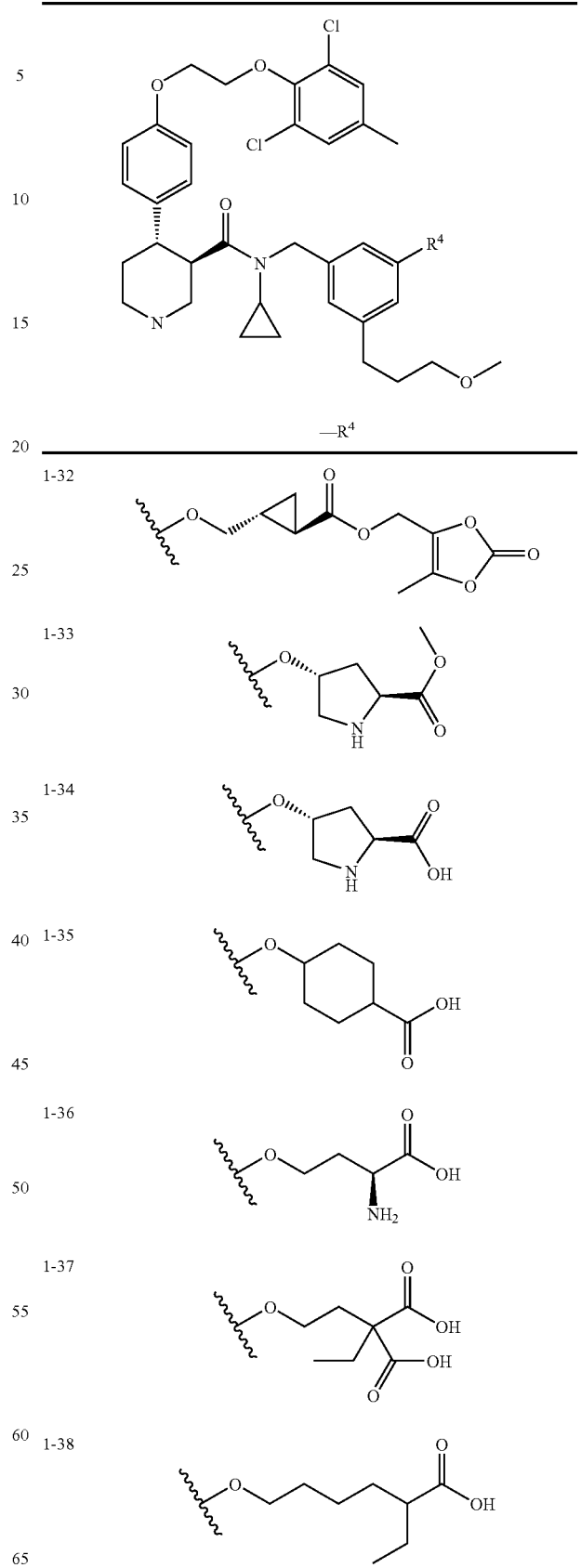

TABLE 1-continued
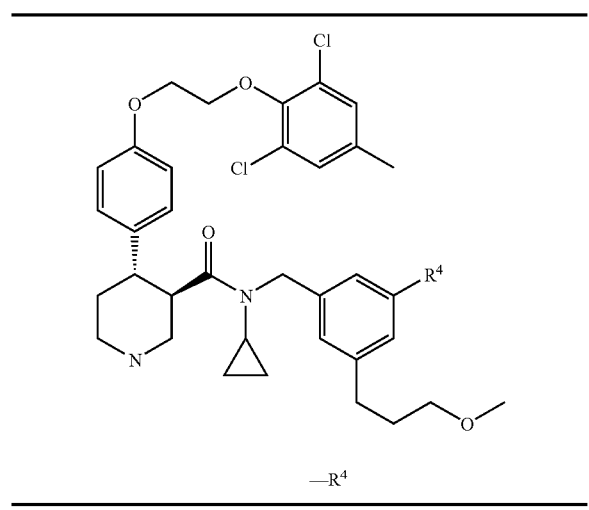
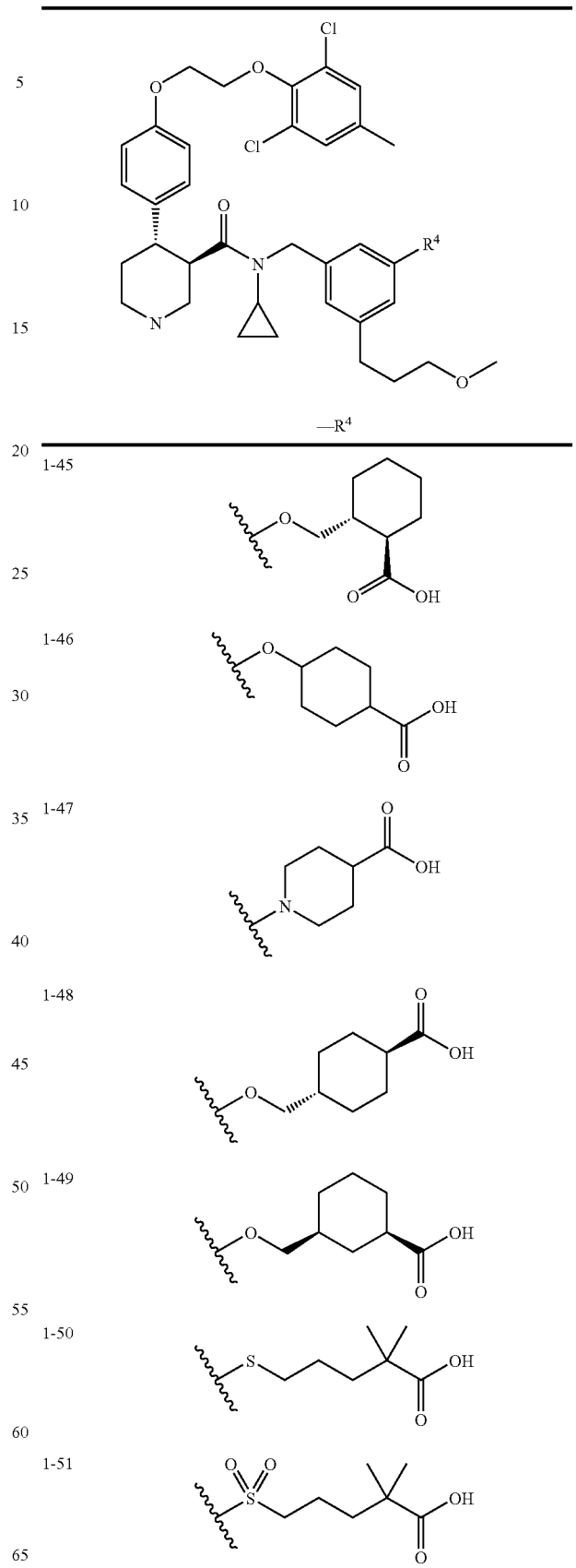

TABLE 1-continued
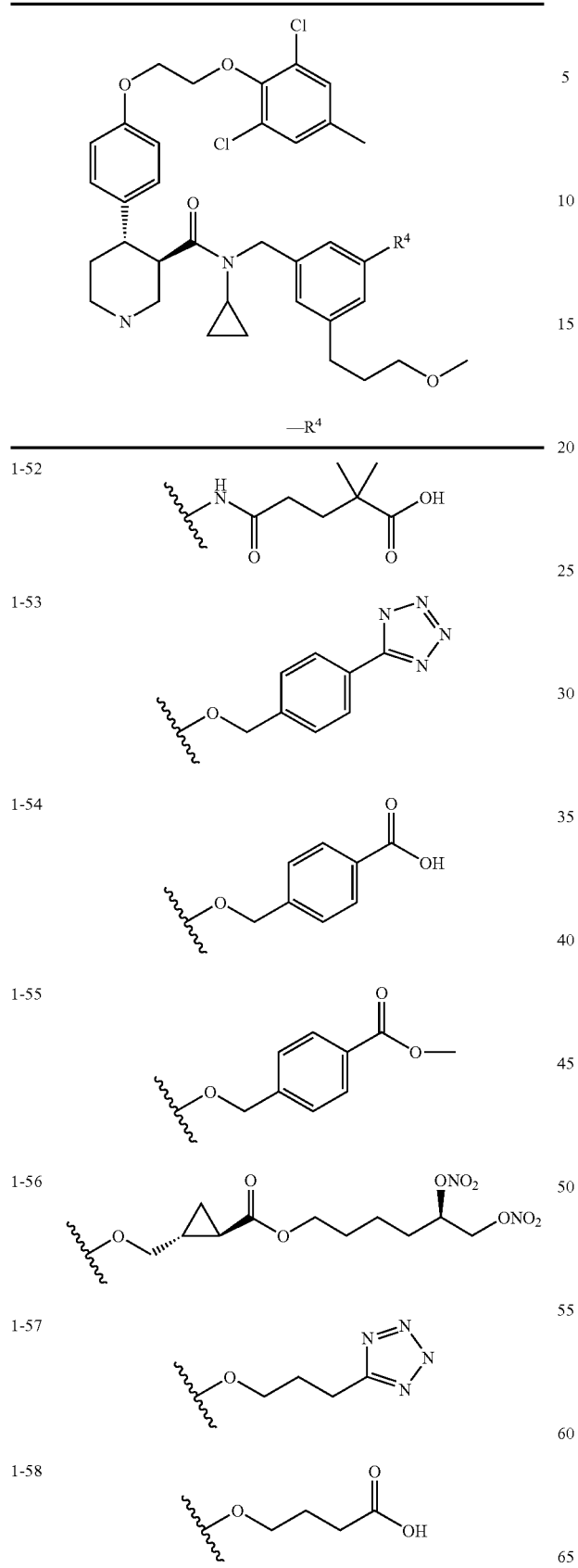
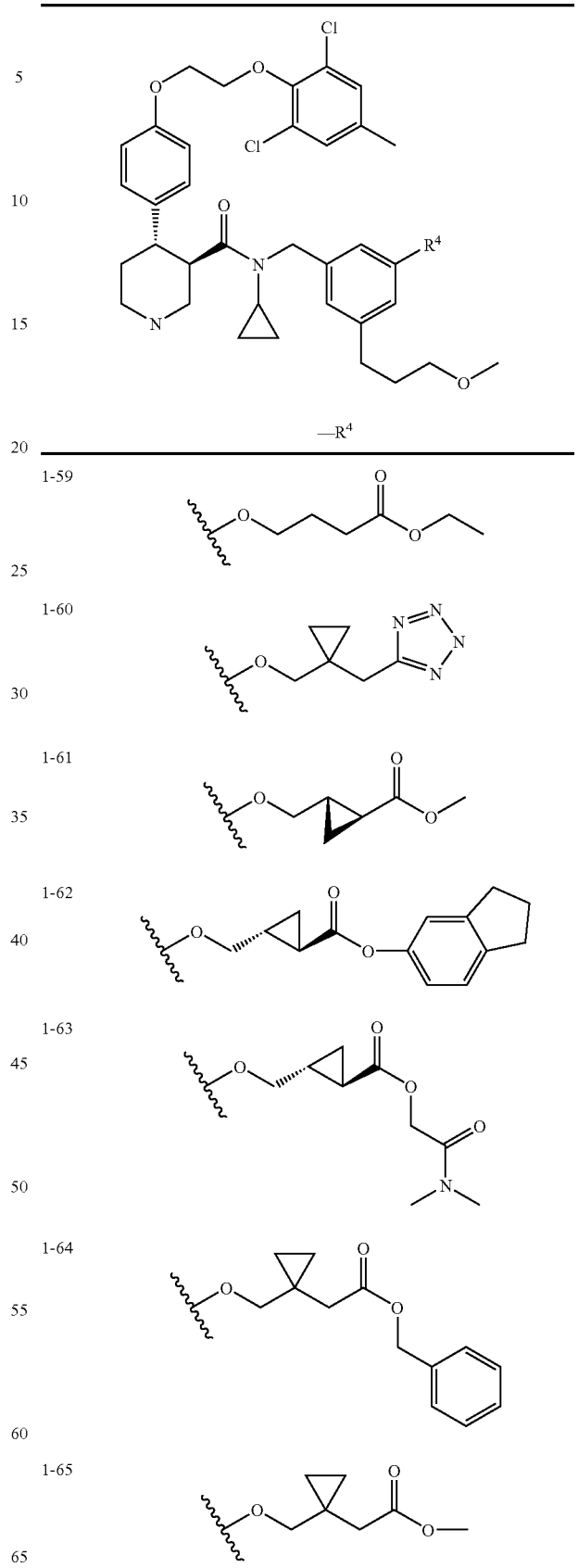

TABLE 1-continued
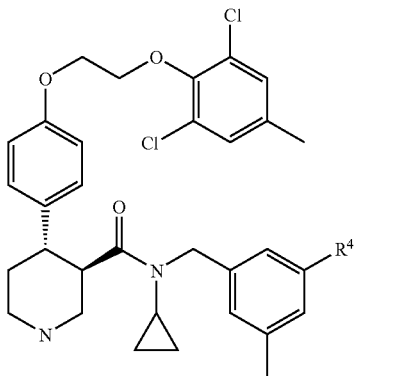
—R⁴
| 1-66 | 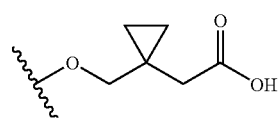 [SMILES: *OCC1(CC(=O)O)CC1] |
TABLE 2
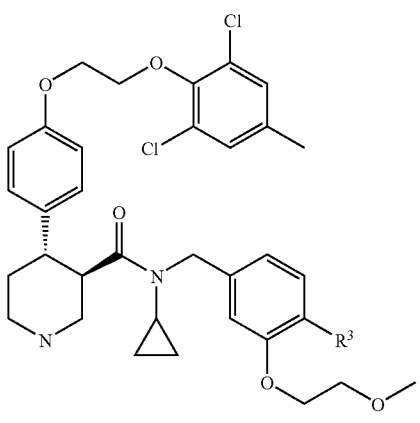
—R³
| 2-1 | 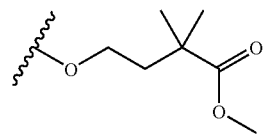 [SMILES: *OCCC(C)(C)C(=O)OC] |
| 2-2 | 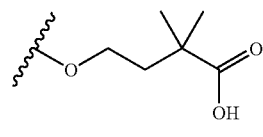 [SMILES: *OCCC(C)(C)C(=O)O] |
| 2-3 | 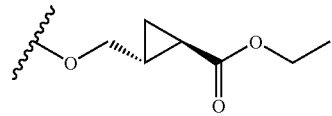 [SMILES: *OC[C@@H]1C[C@H]1C(=O)OCC] |
TABLE 2-continued
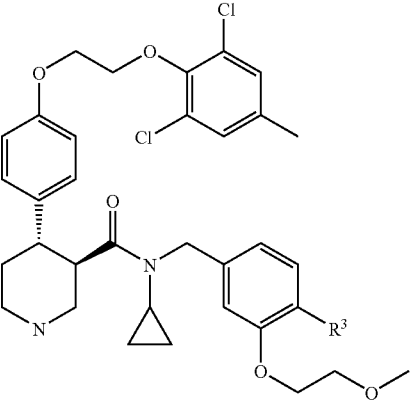
—R³
| 2-4 | 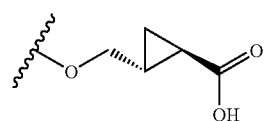 [SMILES: *OC[C@@H]1C[C@H]1C(=O)O] |
| 2-5 | 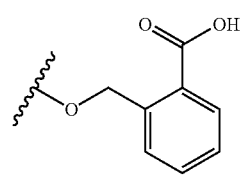 [SMILES: *OCc1ccccc1C(=O)O] |
| 2-6 | 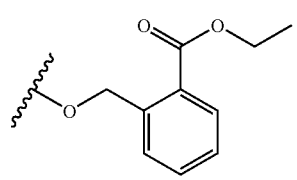 [SMILES: *OCc1ccccc1C(=O)OCC] |
| 2-7 | 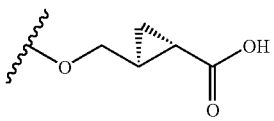 [SMILES: *OC[C@H]1C[C@@H]1C(=O)O] |
| 2-8 | 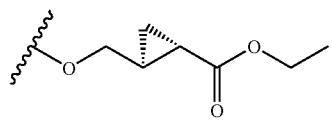 [SMILES: *OC[C@H]1C[C@@H]1C(=O)OCC] |

TABLE 3
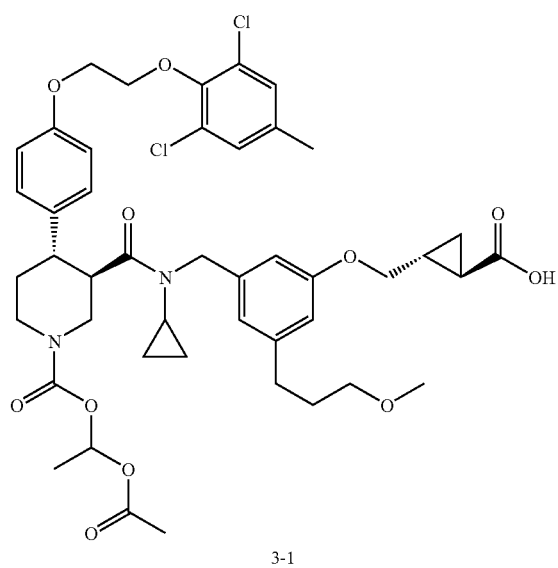
3-1
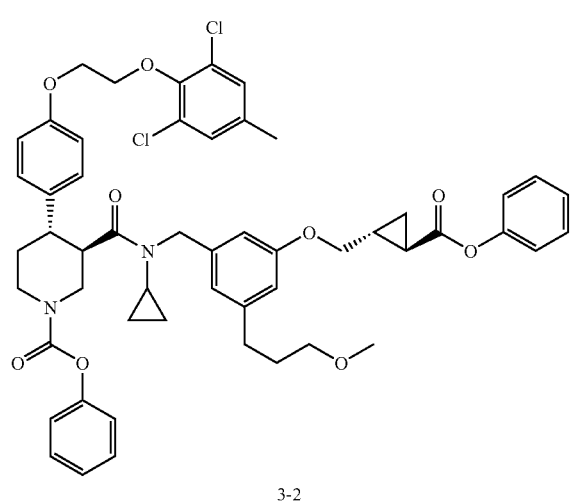
3-2
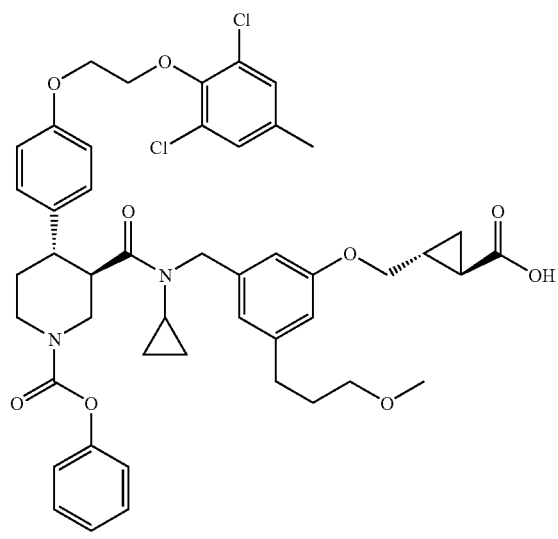 [SMILES: COCCCc1cc(CN(C(=O)[C@H]2CN(C(=O)Oc3ccccc3)CC[C@@H]2c2ccc(OCCOc3c(Cl)cc(C)cc3Cl)cc2)C2CC2)cc(OC[C@@H]2C[C@H]2C(=O)O)c1]
3-3
TABLE 3-continued
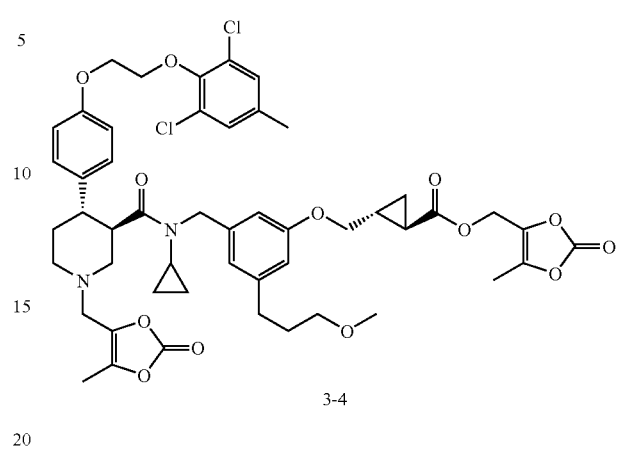
3-4
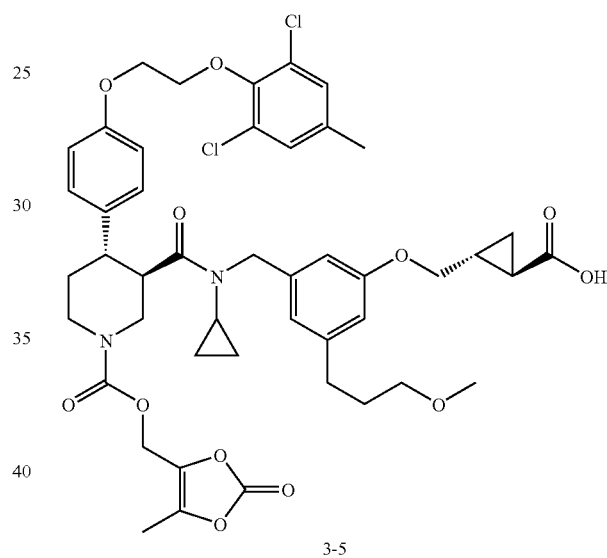
3-5
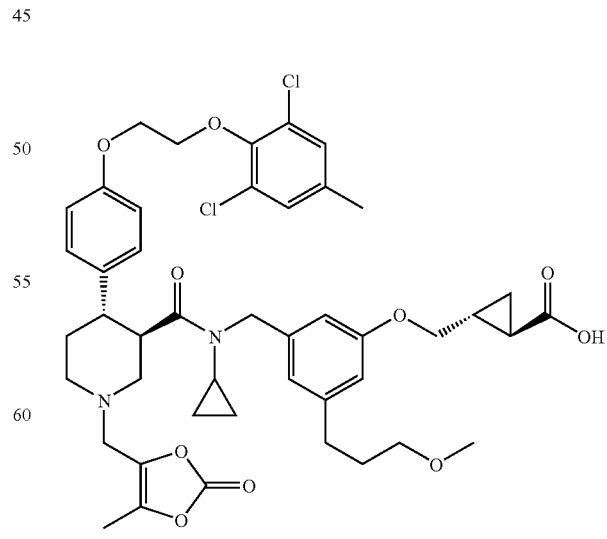
3-6

TABLE 3-continued

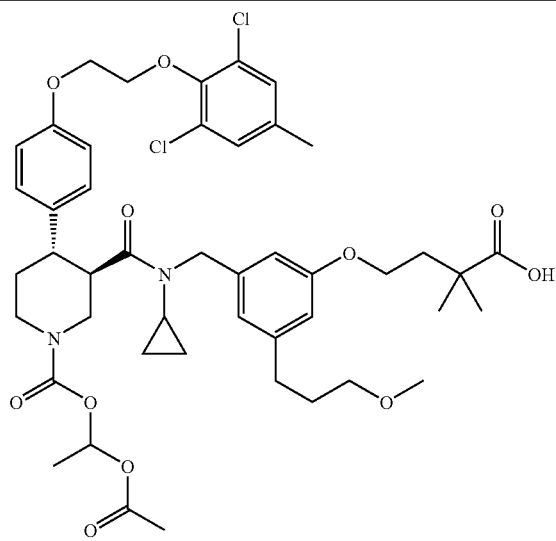

3-7

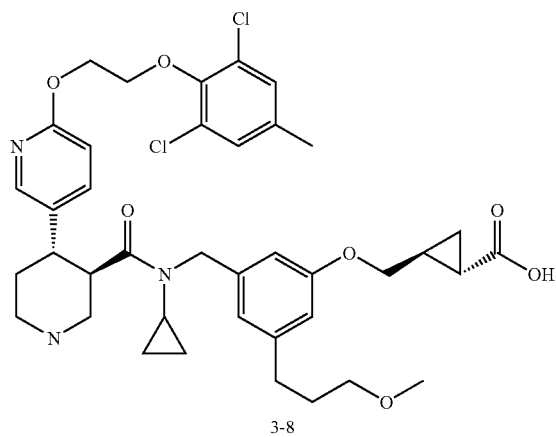

3-8

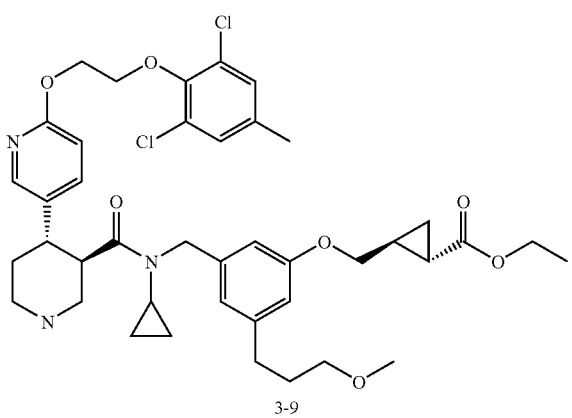

3-9

TABLE 3-continued

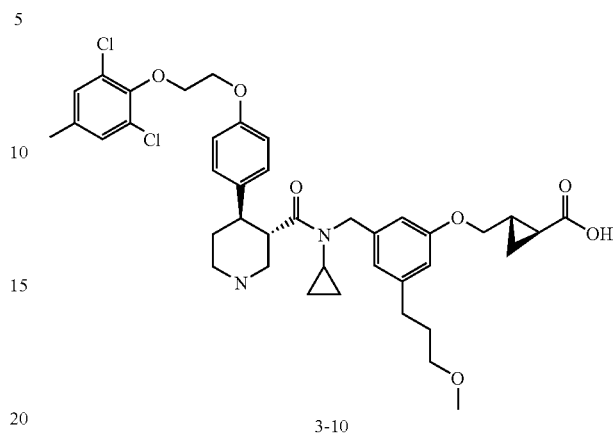

3-10

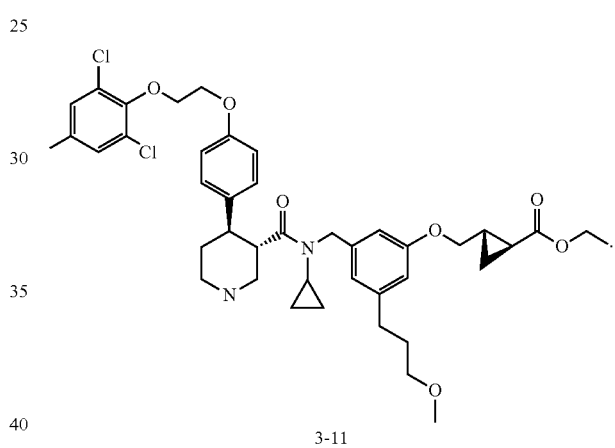

3-11

14. A pharmaceutical composition comprising an effective amount of a compound according to claim 1, or a pharmaceutically acceptable salt thereof, and a pharmaceutically acceptable carrier.

15. A method for the treatment of hypertension, comprising the administration to a patient of a pharmaceutically active amount of a compound according to claim 1.

* * * * *